US008372588B1

(12) United States Patent
Ryan

(10) Patent No.: US 8,372,588 B1
(45) **Date of Patent: *Feb. 12, 2013**

(54) ISOLATED 3'-NONCODING GENOMIC HUMAN RESISTIN POLYNUCLEOTIDE FRAGMENTS

(75) Inventor: James Ryan, Augusta, GA (US)

(73) Assignee: Ryogen LLC, Suffern, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/225,418

(22) Filed: Sep. 3, 2011

Related U.S. Application Data

(62) Division of application No. 12/276,467, filed on Nov. 24, 2008, now Pat. No. 8,012,687, which is a division of application No. 11/483,373, filed on Jul. 7, 2006, now Pat. No. 7,470,522.

(60) Provisional application No. 60/697,815, filed on Jul. 9, 2005.

(51) Int. Cl.
*C12Q 1/68* (2006.01)
*C07H 21/02* (2006.01)

(52) U.S. Cl. ...................................... 435/6.11; 536/23.1

(58) Field of Classification Search ................. 435/6.11; 536/23.1
See application file for complete search history.

(56) References Cited

U.S. PATENT DOCUMENTS 7,470,522 B1 12/2008 Ryan
8,012,687 B1 * 9/2011 Ryan ............................ 435/6.17

OTHER PUBLICATIONS

U.S. Appl. No. 11/483,373 Jan. 16, 2008 Non-Final Rejection.
U.S. Appl. No. 11/483,373 Apr. 30, 2008 Examiner Interview Summary Record.
U.S. Appl. No. 11/483,373 Aug. 5, 2008 Notice of Allowance.
U.S. Appl. No. 11/483,373 Aug. 5, 2008 Notice of Allowability / Examiner's Amendment.
U.S. Appl. No. 12/276,467 Dec. 21, 2010 Non-Final Rejection.
U.S. Appl. No. 12/276,467 Apr. 27, 2011 Notice of Allowance.
U.S. Appl. No. 12/276,467 Apr. 27, 2011 Notice of Allowability.
U.S. Appl. No. 12/276,550 Jul. 6, 2011 Notice of Allowance.
U.S. Appl. No. 12/276,550 Jul. 6, 2011 Notice of Allowability.
Altschul et al., 1997, "Gapped BLAST and PSI-BLAST: a new generation of protein database search programs", Nucleic. Acids Res. 25:3389-3402.
Burge et al., 1997, "Prediction of Complete Genome Structures in Human Genomic DNA", 268:78-94.
Darnell et al. Molecular Cell Biology. p. 373. Scientific American Books. New York 1986.
Katagiri et al., 1995, "A Novel Isoform of Syntaxin-binding Protein Homologous to Yeast Sect Expressed Ubiquitously in Mammalian Cells", J. Biol. Chem. 270:4963-4966.
McTernan et al. "Increased resistin gene and protein expression in human abdominal adipose tissue." J. Clin. Endocrinol. Metab. 87: 2407-2410. 2002.
PUBMED Accession No. AC008763, submitted Aug. 3, 1999, bases 1 to 177062. "*Homo sapiens* chromosome 19 clone CTD-3214H19", *Homo sapiens* chromosome 19 clone CITB-E1_3214H19, * Sequencing in Progress *, 21 unordered pieces. Reference: DOE Joint Genome Institute (direct submission).
PUBMED Accession No. ACO21153 "*Homo sapiens* chromosome 19 clone RP11-492L14", submitted Jan. 14, 2000, bases 1 to 155645. Reference: Waterston, R. H. (direct submission).
PUBMED Accession No. AF205952, "*Homo sapiens* cysteine-rich secreted protein (FIZZ3) mRNA, complete cds.", submitted Aug. 28, 2000, bases 1 to 457. Reference: Holcomb et al. (direct submission).
PUBMED Accession No. AF352730, "C/EBP regulation of XCP/FIZZ/resistin genes" submitted Feb. 23, 2001, bases 1-4922. Reference: Chumakov et al. (direct submission).
PUBMED Accession No. NM_006949, bases 1 to1815 "*Homo sapiens* syntaxin binding protein 2 (STXBP2), mRNA", (multiple submissions—earliest submission 1995) Reference: Ziegler et al., 1996, "Molecular Characterization of a Nonneuronal Human UNC18 Homolog", Genomics 37:19-23.
Steppan et al., 2001, "The hormone resistin links obesity to diabetes", Nature 409:307-312.
Ziegler et al., 1996, "Molecular Characterization of a Nonneuronal Human UNC18 Homolog", Genomics 37:19-23.
U.S. Appl. No. 13/244,497, Non-final Office Action dated Feb. 7, 2012.

* cited by examiner

*Primary Examiner* — Karen Cochrane Carlson
(74) *Attorney, Agent, or Firm* — Cheryl H Agris

(57) ABSTRACT

The invention is directed to isolated genomic polynucleotide fragments that encode human resistin and human syntaxin binding protein 2, vectors and hosts containing these fragments and fragments hybridizing to noncoding regions as well as antisense oligonucleotides to these fragments. The invention is further directed to methods of using these fragments to obtain human resistin and human syntaxin binding protein 2 and to diagnose, treat, prevent and/or ameliorate a pathological disorder.

18 Claims, No Drawings

ISOLATED 3'-NONCODING GENOMIC HUMAN RESISTIN POLYNUCLEOTIDE FRAGMENTS

PRIORITY CLAIM

This application claims priority to application Ser. No. 60/697,815, filed Jul. 9, 2005 under 35 USC 119(e), the contents of which are herein incorporated by reference. This application is a divisional application of application Ser. No. 12/276,467, filed Nov. 24, 2008, which is a divisional application of U.S. Pat. No. 7,470,522 filed Jul. 7, 2006 and issued Dec. 30, 2008, the contents of which are also herein incorporated by reference.

FIELD OF THE INVENTION

The invention is directed to isolated genomic polynucleotide fragments that encode human resistin and human syntaxin binding protein 2, vectors and hosts containing these fragments and fragments hybridizing to noncoding regions as well as antisense oligonucleotides to these fragments. The invention is further directed to methods of using these fragments to obtain human resistin and human syntaxin binding protein and to diagnose, treat, prevent and/or ameliorate a pathological disorder.

BACKGROUND OF THE INVENTION

Chromosome 19p13.3-p13.2 contains genes encoding, for example, zinc-finger protein 14, oncogene VAV1, tartrate-resistant acid phosphatase, bone marrow stromal cell antigen, calponin 1 and syntaxin binding protein 2; the last of which is discussed in detail below. The gene that encodes resistin, is known to be disposed on chromosome 19.

Human Resistin

Human resistin is a protein that interferes with the actions of insulin on liver and muscle. It is disposed largely in white adipose tissue and in crypt epithelium of the intestine. Given its disposition in fatty tissue and its inhibition of insulin effects, resistin is believed to link obesity to type 2 diabetes (Steppan et al., Nature 409: 307-312, 2001). Consistent with this view, antibodies to resistin improve blood sugar levels and insulin actions in mice with diet-induced obesity. Conversely, administration of recombinant resistin impairs glucose tolerance and insulin actions. The resistin cDNA is identical to the cDNAs for entities called FIZZ3, accession number AF205952, and C/EBP-epsilon regulated myeloid-specific secreted cysteine-rich protein precursor, accession number AF352730. The latter sequence contains the intron sequences and some 5'- and 3'-sequences.

Human Syntaxin Binding Protein 2

Human syntaxin binding protein, a member of the STXBP/unc-18/Sec1 protein family, is disposed largely in placenta, lung, liver, kidney, peripheral lymphocytes and pancreas. It is believed to play a role in vesicular transport between the golgi apparatus and the cell membrane in non-neuronal tissues. Mouse syntaxin binding protein 2=binds to syntaxins 1A, 2 and 3 but not to syntaxin 4 (Katagiri et al., J. Biol. Chem. 270: 4963-6, 1995). The human gene is upregulated in interleukin-2 activated natural killer cells (Ziegler et al., Genomics 37: 19-23, 1996). The cDNA has been determined (see accession number NM_006949).

OBJECTS OF THE INVENTION

Although cDNAs encoding the above-disclosed proteins have been isolated, their locations on chromosome 19 have not been determined. Furthermore, genomic nucleic acids encoding these polypeptides have not been isolated. Noncoding sequences play a significant role in regulating the expression of polypeptides as well as the processing of RNA encoding these polypeptides.

There is clearly a need for obtaining genomic polynucleotide sequences encoding these polypeptides. Therefore, it is an object of the invention to isolate such genomic polynucleotide sequences.

SUMMARY OF THE INVENTION

The invention is directed to isolated genomic nucleic acid molecules or polynucleotides, said polynucleotides obtainable from human chromosome 19 comprising a naturally occurring polynucleotide sequence at least 95% identical to a sequence selected from the group consisting of:

(a) a forward or reverse strand of a nucleic acid molecule encoding a polypeptide selected from the group consisting of human resistin depicted in SEQ ID NO:1 and/or human syntaxin binding protein 2 depicted in SEQ ID NO:2 or variant of SEQ ID NO:1 or SEQ ID NO:2;

(b) a forward or reverse strand of a nucleic acid molecule containing SEQ ID NO:3 which encodes human resistin depicted in SEQ ID NO:1 and/or SEQ ID NO:4 which encodes human syntaxin binding protein 2 depicted in SEQ ID NO:2 or variant of SEQ ID NO:3 and/or SEQ ID NO:4;

(c) a forward or reverse strand of a nucleic acid molecule at least 20 nucleotides in length unique to a noncoding region(s) of SEQ ID NO: 3 or 4, preferably about 20-35,000 in length;

(d) a forward or reverse strand of a nucleic acid molecule at least 60 nucleotides in length unique to a contiguous coding and noncoding nucleic acid sequence(s) of SEQ ID NO:3 or 4, preferably about 60-35,000 nucleotides in length;

(e) a nucleic acid molecule or its reverse strand that extends from the 5'-end of SEQ ID NO:3 through the 3'-end of SEQ ID NO:4 as depicted in SEQ ID NO:5;

(f) a nucleic acid molecule which hybridizes to any one of the nucleic acid molecules specified in (a)-(b) and as well as nucleic acid constructs, expression vectors and host cells containing these polynucleotide sequences.

The polynucleotides of the present invention may be used for the manufacture of a gene therapy for the prevention, treatment or amelioration of a medical condition by adding an amount of a composition comprising said polynucleotide effective to prevent, treat or ameliorate said medical condition.

The invention is further directed to obtaining these polypeptides by:

(a) culturing host cells comprising these sequences under conditions that provide for the expression of said polypeptide and (b) recovering said expressed polypeptide.

The polypeptides obtained may be used to produce antibodies by (a) optionally conjugating said polypeptide to a carrier protein;

(b) immunizing a host animal with said polypeptide or peptide-carrier protein conjugate of step (b) with an adjuvant and (c) obtaining antibody from said immunized host animal.

The nucleic acid molecules of the present invention may be used for the manufacture of a medicament for prevention, treatment or amelioration of a medical condition. In a specific embodiment, the noncoding regions are transcription regulatory regions. The transcription regulatory regions may be used to produce a heterologous peptide by expressing in a host cell, said transcription regulatory region operably linked to a polynucleotide encoding the heterologous polypeptide and recovering the expressed heterologous polypeptide.

The polynucleotides of the present invention may be used to diagnose a pathological condition in a subject comprising (a) determining the presence or absence of a mutation in the polynucleotides of the present invention and (b) diagnosing a pathological condition or a susceptibility to a pathological condition based on the presence or absence of said mutation.

The invention is further directed to kits and/or microarrays comprising the nucleic acids of the present invention. The kits may comprise microarrays. Furthermore, the kits of the present invention may comprise other sequences, e.g., cDNA sequences.

DEFINITIONS

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL Press, 1986, "Immobilized Cells And Enzymes"; Perbal, 1984, "A Practical Guide To Molecular Cloning."

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," and the include plural references unless the context clearly dictates otherwise. The terms "polynucleotide(s)", "nucleic acid molecule(s)" and "nucleic acids" will be used interchangeably.

Furthermore, the following terms shall have the definitions set out below.

As defined herein "isolated" refers to material removed from its original environment and is thus altered "by the hand of man" from its natural state.

The amino acid residues described herein are preferred to be in the "L" isomeric form. However, residues in the "D" isomeric form can be substituted for any L-amino acid residue, as long as the desired functional is retained by the polypeptide. NH, refers to the free amino group present at the amino terminus of a polypeptide. COOH refers to the free carboxy group present at the carboxy terminus of a polypeptide.

"Nucleic acid construct" is defined herein, is a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term "expression cassette" when the nucleic acid construct contains all the control sequences required for expression of a coding sequence of the present invention.

The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) of the first open reading frame at the 5'-end of the mRNA and a transcription terminator sequence located just downstream of the open reading frame at the 3'-end of the mRNA. A coding sequence can include, but is not limited to, DNA, cDNA, and recombinant nucleic acid sequences.

A "heterologous" region of a recombinant cell is an identifiable segment of nucleic acid within a larger nucleic acid molecule that is not found in association with the larger molecule in nature.

An "expression vector" may be any vector (e.g., a plasmid or virus) which can be conveniently subjected to recombinant DNA procedures and can bring about the expression of the nucleic acid sequence.

An "origin of replication" refers to those DNA sequences that participate in DNA synthesis.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence. Transcriptional and translational control sequences are DNA regulatory sequences, such as promoters, enhancers, polyadenylation signals, terminators, and the like, that provide for the expression of a coding sequence in a host cell.

A "signal sequence" can be included before the coding sequence of the mature polypeptide. This sequence encodes a signal peptide, N-terminal to the mature polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

It should be appreciated that also within the scope of the present invention are nucleic acid sequences encoding the polypeptide(s) of the present invention, which code for a polypeptide having the same amino acid sequence as the sequences disclosed herein, but which are degenerate to the nucleic acids disclosed herein. By "degenerate to" is meant that a different three-letter codon is used to specify a particular amino acid.

The term "polypeptide" refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

A nucleic acid molecule is "operatively linked" to an expression control sequence when the expression control sequence controls and regulates the transcription and translation of nucleic acid sequence. The term "operatively linked" includes having an appropriate start signal (e.g., ATG) in front of the nucleic acid sequence to be expressed and maintaining the correct reading frame to permit expression of the nucleic acid sequence under the control of the expression control sequence and production of the desired product encoded by the nucleic acid sequence. If a gene that one desires to insert into a recombinant DNA molecule does not contain an appropriate start signal, such a start signal can be inserted in front of the gene.

The term "stringent hybridization conditions" are known to those skilled in the art and can be found in Current Protocols in Molecular Biology, John Wiley & Sons, N.Y. (1989), 6.3.1-6.3.6. A preferred, non-limiting example of stringent hybridization conditions is hybridization in 6× sodium chloride/sodium citrate (SSC) at about 45° C., followed by one or more washes in 0.2.X SSC, 0.1% SDS at 50° C., preferably at 55° C., and more preferably at 60° C. or 65° C.

As used herein, "Arrays" or "Microarrays" refers to an array of distinct polynucleotides or oligonucleotides deposited on a substrate, such as paper, nylon or other type of membrane, filter, chip, glass slide, or any other suitable solid support. In one embodiment, the microarray is prepared and used according to the methods described in U.S. Pat. No. 5,837,832, PCT application WO95/11995, Lockhart et al. (1996; Nat. Biotech. 14: 1675-1680) and Schena et al. (1996; Proc. Natl. Acad. Sci. 93: 10614-10619). In other embodiments, such arrays are produced by the methods described by Brown et al., U.S. Pat. No. 5,807,522.

As defined herein, a "gene" is the segment of DNA involved in producing a polypeptide chain; it includes regions preceding and following the coding region, as well as intervening sequences (introns) between individual coding segments (exons).

As defined herein, "unique to" means a sequence that only occurs once in a genome.

DETAILED DESCRIPTION OF THE INVENTION

The invention is directed to isolated genomic polynucleotide fragments that encode human resistin and human syntaxin binding protein 2, which in a specific embodiment are the human resistin and human syntaxin binding protein 2 genes, as well as vectors and hosts containing these fragments and polynucleotide fragments hybridizing to noncoding regions, as well as antisense oligonucleotides to these fragments. The genomic polynucleotide fragments of the present invention may contain both sequences encoding resistin and syntaxin binding protein 2 and specifically may contain SEQ ID NO:3 and/or 4 or portions of SEQ ID NO:3 and/or 4.

The polynucleotides of the present invention may be in the form of RNA or in the form of DNA, which DNA includes genomic DNA and synthetic DNA. The DNA may be double-stranded or single-stranded and if single stranded may be the coding strand or non-coding strand. The genes encoding human resistin and human syntaxin binding protein 2 are disposed in the chromosome 19 genomic clones of accession numbers AC008763, gi 13699420, last contig (nucleotides 141174-194036), and AC021153, gi 8570240, reverse complement of contig 17 (nucleotides 77433-94571). A composite of these two contigs, corrected for overlapping sequence, is prepared to yield a 64,700 base pair sequence. In the latter composite, the resistin gene is disposed in nucleotides 1-38587 (SEQ ID NO:3). The syntaxin binding protein 2 gene is disposed in the last 30943 nucleotides (SEQ ID NO:4).

The polynucleotides of the invention are naturally occurring polynucleotide sequences having at least a 95% identity and may have a 96%, 97%, 98%, 99%, 99.5% or 99.9% identity to the polynucleotides depicted in SEQ ID NOS:3, 4 or 5 as well as the polynucleotides in reverse sense orientation, or the polynucleotide sequences encoding the human resistin and human syntaxin binding protein 2 polypeptides depicted in SEQ ID NOS:1 or 2 respectively.

The comparison of sequences and determination of percent identity and similarity between two sequences can be accomplished using a mathematical algorithm (Lesk, A. M., ed., 1988, Computational Molecular Biology, Oxford University Press, New York; Smith, D. W., ed., 1993, Biocomputing: Informatics and Genome Projects, Academic Press, New York; Griffin, A. M., and Griffin, H. G., eds, 1994, Computer Analysis of Sequence Data, Part 1, Humana Press, New Jersey; von Heinje, G., 1987, Sequence Analysis in Molecular Biology, Academic Press; and Gribskov, M. and Devereux, J., eds., 1991, Sequence Analysis Primer, M Stockton Press, New York). In a preferred embodiment, the percent identity between two amino acid sequences is determined using the Needleman and Wunsch (1970, J. Mol. Biol. 48:444-453) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux et al., 1984, Nucleic Acids Res. 12:387), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of Myers and Miller (1989, CABIOS, 4:11-17) which has been incorporated into the ALIGN program (version 2.0), using a PAM120 weight residue table, a gap length penalty of 12 and a gap penalty of 4.

The nucleic acid sequences of the present invention can further be used as a "query sequence" to perform a search against sequence databases to, for example, identify other family members or related sequences. Such searches can be performed using the BLASTN and BLASTX programs (version 2.0) of Altschul, et al. (1990, J. Mol. Biol. 215:403-410). BLAST nucleotide searches can be performed with the BLASTN program, score=100, wordlength=12 to obtain nucleotide sequences homologous to the nucleic acid molecules of the invention. BLASTN protein searches can be performed with the BLASTX program, score=50, wordlength=3 to obtain amino acid sequences homologous to the proteins of the invention. To obtain gapped alignments for comparison purposes, Gapped BLASTN can be utilized as described in Altschul et al. (1997, Nucleic Acids Res.

25:3389-3402). When utilizing BLAST and gapped BLAST programs, the default parameters of the respective programs (e.g., BLASTX and BLASTN) can be used.

The invention also encompasses polynucleotides that hybridize to the polynucleotides depicted in SEQ ID NOS: 3, 4 and/or 5. This polynucleotide may have a maximum length of SEQ ID NOS: 3, 4 and/or 5. A polynucleotide "hybridizes" to another polynucleotide, when a single-stranded form of the polynucleotide can anneal to the other polynucleotide under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a temperature of 42° C., can be used, e.g., 5×SSC, 0.1% SDS, 0.25% milk, and no formamide; or 40% formamide, 5×SSC, 0.5% SDS). "Stringent hybridization conditions" can be found in Current Protocols in Molecular Biology, John Wiley & Sons, N.Y. (1989), 6.3.1-6.3.6. A preferred, non-limiting example of stringent hybridization conditions is hybridization in 6× sodium chloride/sodium citrate (SSC) at about 45° C., followed by one or more washes in 0.2.X SSC, 0.1% SDS at 50° C., preferably at 55° C., and more preferably at 60° C. or 65° C.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or complementarity between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA.

The invention is further directed to a nucleic acid construct comprising the nucleic acid molecules of the present invention. The nucleic acid sequence encoding the desired polypeptide, whether in fused or mature form, and whether or not containing a signal sequence to permit secretion, may be ligated into expression vectors suitable for any convenient host. The vector includes a plasmid, single or double stranded phage, a single or double stranded RNA or DNA viral vector, or artificial chromosome, such as a BAC, PAC, YAC, or MAC.

Polynucleotide and Polypeptide Variants

The invention is directed to both polynucleotide and polypeptide variants. A "variant" refers to a polynucleotide or polypeptide differing from the polynucleotide or polypeptide of the present invention, but retaining essential properties thereof. Generally, variants are overall closely similar and in many regions, identical to the polynucleotide or polypeptide of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5 or 1-2 amino acids are substituted, deleted, or added in any combination are also preferred.

The invention also encompasses allelic variants of said polynucleotides. An allelic variant denotes any of two or more alternative forms of a gene occupying the same chromosomal locus. Allelic variation arises naturally through mutation, and may result in polymorphism within populations and is thought to frequently occur. Gene mutations can be silent (no change in the encoded polypeptide) or may encode polypeptides having altered amino acid sequences. An allelic variant has a high homology to the original gene sequence. An allelic variant of a polypeptide is a polypeptide encoded by an allelic variant of a gene.

The amino acid sequences of the variant polypeptides may differ from the amino acid sequences depicted in SEQ ID NOS:1 or 2 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine) Amino acid substitutions which do not generally alter the specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, as well as these in reverse.

Noncoding Regions

The invention is further directed to polynucleotide fragments containing or hybridizing to noncoding regions of the human resistin and human syntaxin binding protein 2 genes. These include but are not limited to an intron, a 5'-non-coding region, a 3'-non-coding region (see Tables 1-2), as well as transcription factor binding sites (see Table 3).

The invention is further directed to polynucleotide fragments or nucleic acid molecules containing or hybridizing to contiguous exon/intron and intron/exon sequences of human resistin or human syntaxin binding protein 2 genes. These sequences encompass each splice site, where the intron is removed, the exon-intron junction and additionally includes the consensus sequence spanning the exon and intron sequences immediately adjacent to the splice site: The fragments are at least 20 nucleotides in length and in one embodiment contain at least 10 nucleotides of intron sequences. Thus, the invention would encompass a nucleic acid molecule that contains or hybridizes to a polynucleotide fragment that combines contiguous coding and noncoding nucleic acid sequences of SEQ ID NO:3 or 4. Further, the polynucleotide fragments of the present invention may contain more than one exon-intron and/or intron-exon regions.

The polynucleotide fragment may be a short polynucleotide fragment which is between about 8 nucleotides to about 20 or 40 nucleotides in length. Such shorter fragments may be useful for diagnostic purposes. Such short polynucleotide fragments are also preferred with respect to polynucleotides or nucleic acid molecules containing or hybridizing to polynucleotides or nucleic acid molecules containing noncoding regions including but not limited to 5' and 3' noncoding region, intron regions, contiguous exon-intron and intron-exon regions. Alternatively larger fragments, e.g., of about 50, 60, 100, 150, 200, 300, 400, 500, 600, 750, 800, 900, 1000, 1,500, 2000, 3000, 4000, 5000 or about 10000 nucleotides in length may be used.

TABLE 1

Exon/Intron Organization of the Resistin Gene in Genomic SEQ ID NO: 3 (Reverse Strand Coding).

| EXON | Nucleotide No. | Amino Acid No. |
|---|---|---|
| Stop Codon | 19611-19613 | |
| 3 | 19614-19742 | 108-66 |
| 2 | 20063-20140 | 65-40 |
| 1 | 20517-20633 | 39-1 |

TABLE 2

Exon/Intron Organization of the Syntaxin Binding Protein 2 Gene in Genomic SEQ ID NO: 4 (Reverse Strand Coding).

| Exon | Nucleotide No. | Amino Acid No. |
|---|---|---|
| Stop Codon | 8391-8393 | |
| 19 | 8394-8477 | 593-566 |
| 18 | 8691-8849 | 565-513 |
| 17 | 8956-9039 | 512-485 |
| 16 | 9857-9952 | 484-453 |
| 15 | 10895-11005 | 452-416 |
| 14 | 11450-11590 | 415-369 |
| 13 | 12959-13036 | 368-343 |
| 12 | 13153-13221 | 342-320 |
| 11 | 13378-13434 | 319-301 |
| 10 | 13667-13774 | 300-265 |
| 9 | 13870-13998 | 264-222 |
| 8 | 14083-14166 | 221-194 |
| 7 | 14347-14502 | 193-142 |
| 6 | 15204-15302 | 141-109 |
| 5 | 15393-15470 | 108-83 |
| 4 | 16394-16471 | 82-57 |
| 3 | 17102-17182 | 56-30 |
| 2 | 17426-17476 | 29-13 |
| 1 | 19016-19051 | 12-1 |

TABLE 3

NUMBERS OF TRANSCRIPTION FACTOR BINDING SITES ON GENES THAT ENCODE RESISTIN AND SYNTAXIN BINDING PROTEIN 2 (STXBP2).

| BINDING SITES | RESISTIN | STXBP2 |
|---|---|---|
| AP1_C | 6 | 2 |
| AP4_Q5 | 3 | 4 |
| AP4_Q6 | 3 | 4 |
| CAAT_01 | 7 | 4 |
| CREBP1CJUN_01 | 3 | |
| CREB_01 | 2 | |
| DELTAEF1_01 | 12 | 7 |
| GATA_C | | 2 |
| GC_01 | | 2 |
| GKLF_01 | 2 | 2 |
| HFH3_01 | 2 | |
| IK2_01 | 3 | |
| LMO2COM_01 | 5 | 7 |
| LMO2COM_02 | 3 | 4 |
| LYF1_01 | 36 | 14 |
| MYOD_Q6 | 17 | 11 |
| MZF1_01 | 51 | 50 |
| NFAT_Q6 | 3 | |
| NKX25_01 | 30 | 14 |
| NMYC_01 | | 3 |
| PADS_C | 2 | |
| S8_01 | | 2 |
| SOX5_01 | 5 | 6 |
| SP1_Q6 | | 3 |

TABLE 3-continued

NUMBERS OF TRANSCRIPTION FACTOR BINDING SITES ON GENES THAT ENCODE RESISTIN AND SYNTAXIN BINDING PROTEIN 2 (STXBP2).

| BINDING SITES | RESISTIN | STXBP2 |
|---|---|---|
| SREBP1_01 | 2 | |
| TCF11_01 | 17 | 7 |
| USF_01 | 14 | 14 |
| USF_C | 18 | 14 |

In a specific embodiment, such noncoding sequences are expression control sequences. In a more specific embodiment of the invention, the expression control sequences may be operatively linked to a polynucleotide encoding a heterologous polypeptide. Such expression control sequences may be about 50-200 nucleotides in length and specifically about 50, 100, 200, 500, 600, 1000 or 2000 nucleotides in length. The invention is further directed to antisense oligonucleotides and mimetics to these polynucleotide sequences. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature polypeptides of the present invention, is used to design an antisense RNA oligonucleotide of from about 10 to 40 base pairs in length. A DNA oligonucleotide is designed to be complementary to a region of the gene involved in transcription or RNA processing (triple helix (see Lee et al., Nucl. Acids Res., 6:3073 (1979); Cooney et al, Science, 241:456 (1988); and Dervan et al., Science, 251: 1360 (1991)), thereby preventing transcription and the production of said polypeptides.

Expression of Polypeptides

Isolated Polynucleotide Sequences

The human chromosome 19 genomic clones of accession numbers AC008763, gi 13699420, last contig (nucleotides 141174-194036) and AC021153, gi 8570249, reverse complement of contig 17 (nucleotides 77433-94571) have been discovered to contain the human resistin and human syntaxin binding protein 2 genes by Genscan analysis (Burge et al., 1997, J. Mol. Biol. 268:78-94), BLAST2 and TBLASTN analysis (Altschul et al., 1997, Nucl. Acids Res. 25:3389-3402). The sequences of AC008763, gi 13699420, and AC021153, gi 8570249 are compared to the human resistin and syntaxin cDNA sequences, accession numbers AF352730 (resistin) and AF205952. It has been found that resistin is disposed immediately adjacent to the syntaxin binding protein 2 gene. A composite of these two contigs, corrected for overlapping sequence, is prepared to yield a 64,700 base pair sequence (SEQ ID NO:5). In the latter composite, the resistin gene is disposed in nucleotides 1-38587 (SEQ ID NO:3). The syntaxin binding protein 2 gene is disposed in the last 30943 nucleotides (SEQ ID NO:4).

The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleic acid sequence-based amplification (NASBA) or long range PCR may be used. In a specific embodiment, 5'- or 3'-non-coding portions of the gene may be identified by methods including but are not limited to, filter probing, clone enrichment using specific probes and protocols similar or identical to 5'- and 3'-"RACE" protocols which are well known in the art. For instance, a method similar to 5'-RACE is available for generating the missing 5'-end of a desired full-length transcript. (Fromont-Racine et al., 1993, Nucl. Acids Res. 21:1683-1684).

Once the DNA fragments are generated, identification of the specific DNA fragment containing the desired human resistin and/or syntaxin gene may be accomplished in a number of ways. For example, if an amount of a portion of a human resistin or syntaxin gene or its specific RNA, or a fragment thereof, is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). The present invention provides such nucleic acid probes, which can be conveniently prepared from the specific sequences disclosed herein, e.g., a hybridizable probe having a nucleotide sequence corresponding to at least a 10, and preferably a 15, nucleotide fragment of the sequences depicted in SEQ ID NO:2. Preferably, a fragment is selected that is unique to the polypeptides of the invention. Methods are commonly known in the art for preparing such unique sequences and are reviewed in Stoughton, 2005, Annu. Rev. Biochem. 74:53-82. Those DNA fragments with substantial homology to the probe will hybridize. As noted above, the greater the degree of homology, the more stringent hybridization conditions can be used. In one embodiment, low stringency hybridization conditions are used to identify a homologous human resistin or syntaxin polynucleotide. However, in a preferred aspect, and as demonstrated experimentally herein, a nucleic acid encoding a polypeptide of the invention will hybridize to a nucleic acid derived from the polynucleotide sequence depicted in SEQ ID NO:2 or a hybridizable fragment thereof, under moderately stringent conditions; more preferably, it will hybridize under high stringency conditions.

Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, or antigenic properties as known for the human resistin or syntaxin polynucleotide.

A gene encoding human resistin or syntaxin polypeptide can also be identified by mRNA selection, i.e., by nucleic acid hybridization followed by in vitro translation. In this procedure, fragments are used to isolate complementary mRNAs by hybridization Immunoprecipitation analysis or functional assays of the in vitro translation products of the products of the isolated mRNAs identifies the mRNA and, therefore, the complementary DNA fragments, that contain the desired sequences.

Nucleic Acid Constructs

The present invention also relates to nucleic acid constructs comprising a polynucleotide sequence containing the exon/intron segments of the human resistin and/or syntaxin gene operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) and a transcription terminator sequence located just downstream of the open reading frame at the 3'-end of the mRNA. A coding sequence can include, but is not limited to, DNA, cDNA, and recombinant nucleic acid sequences.

The isolated polynucleotide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The control sequence may be an appropriate promoter sequence, a nucleic acid sequence which is recognized by a host cell for expression of the nucleic acid sequence. The promoter sequence contains transcriptional control sequences that regulate the expression of the polynucleotide. The promoter may be any nucleic acid sequence that shows transcriptional activity in the host cell of choice including mutant, truncated, and hybrid promoters, and may be obtained from genes encoding extracellular or intracellular polypeptides either homologous or heterologous to the host cell.

The control sequence may also be a suitable transcription terminator sequence, a sequence recognized by a host cell to terminate transcription. The terminator sequence is operably linked to the 3'-terminus of the nucleic acid sequence encoding the polypeptide. Any terminator which is functional in the host cell of choice may be used in the present invention.

The control sequence may also be a suitable leader sequence, a nontranslated region of an mRNA which is important for translation by the host cell. The leader sequence is operably linked to the 5'-terminus of the nucleic acid sequence encoding the polypeptide. Any leader sequence that is functional in the host cell of choice may be used in the present invention.

The control sequence may also be a polyadenylation sequence, a sequence which is operably linked to the 3'-terminus of the nucleic acid sequence and which, when transcribed, is recognized by the host cell as a signal to add polyadenosine residues to transcribed mRNA. Any polyadenylation sequence which is functional in the host cell of choice may be used in the present invention.

The control sequence may also be a signal peptide coding region, which codes for an amino acid sequence linked to the amino terminus of the polypeptide which can direct the encoded polypeptide into the cell's secretory pathway. The 5'-end of the coding sequence of the nucleic acid sequence may inherently contain a signal peptide-coding region naturally linked in translation reading frame with the segment of the coding region which encodes the secreted polypeptide. Alternatively, the 5'-end of the coding sequence may contain a signal peptide coding region which is foreign to the coding sequence. The foreign signal peptide-coding region may be required where the coding sequence does not normally contain a signal peptide-coding region. Alternatively, the foreign signal peptide-coding region may simply replace the natural signal peptide-coding region in order to obtain enhanced secretion of the polypeptide. However, any signal peptide-coding region which directs the expressed polypeptide into the secretory pathway of a host cell of choice may be used in the present invention.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, the *Rhizomucor miehei* aspartic proteinase gene, or the *Myceliophthora thermophila* laccase gene (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

Both eukaryotic and prokaryotic host systems are presently used in forming recombinant polypeptides. The polypeptide is then isolated from lysed cells or from the culture medium and purified to the extent needed for its intended use. Purification may be by techniques known in the art, for example, differential extraction, salt fractionation, chromatography on ion exchange resins, affinity chromatography, centrifugation, and the like. See, for example, Methods in Enzymology for a variety of methods for purifying proteins. Both prokaryotic and eukaryotic host cells may be used for expression of desired coding sequences when appropriate control sequences, which are compatible with the designated host, are used. Bacterial cells include, but are not limited to, *E. coli, Streptomyces*, and *Salmonella typhimurium*. Expression control sequences for prokaryotes include promoters, optionally containing operator portions, and ribosome binding sites. Transfer vectors compatible with prokaryotic hosts are commonly derived from, for example, pBR322, a plasmid containing operons conferring ampicillin and tetracycline resistance, and the various pUC vectors, which also contain sequences conferring antibiotic resistance markers. These markers may be used to obtain successful transformants by selection. Commonly used prokaryotic control sequences include the Beta-lactamase (penicillinase) and lactose promoter systems, the tryptophan (trp) promoter system and the lambda-derived $P_L$ promoter and N gene ribosome binding site and the hybrid TAC promoter derived from sequences of the trp and lac UV5 promoters. The foregoing systems are particularly compatible with *E. coli*; if desired, other prokaryotic hosts such as strains of *Bacillus* or *Pseudomonas* may be used, with corresponding control sequences.

Eukaryotic cells include, but are not limited to, yeast, insect cells such as *Drosophila*, animal cells such as COS and CHO cells, and plant cells. *Saccharomyces cerevisiae* and *Saccharomyces carlsbergensis* are the most commonly used yeast hosts, and are convenient fungal hosts. Yeast compatible vectors carry markers that permit selection of successful transformants by conferring prototrophy to auxotrophic mutants or resistance to heavy metals on wild-type strains. Yeast compatible vectors may employ the 2 micron origin of replication, the combination of CEN3 and ARS1 or other means for assuring replication, such as sequences which will result in incorporation of an appropriate fragment into the host cell genome. Examples of vectors for expression in yeast e.g., *S. cerevisiae* include pYepSec1 (Baldari, et al., 1987, EMBO J. 6:229-234; pMFa (Kuijan et al., 1982, Cell 30:933-943), pJRY88 (Schultz et al., 1987, Gene 54:113-123), and pYES2 (Invitrogen Corporation, San Diego, Calif.). The nucleic acid molecules can also be expressed in insect cells using, for example, baculovirus expression vectors. Baculovirus vectors available for expression of proteins in cultured insect cells (e.g., Sf 9 cells) include the pAc series (Smith et al., 1983, Mol. Cell Biol. 3:2156-2165) and the pVL series (Lucklow et al., 1989, Virology 170:31-39).

Mammalian cell lines available as hosts for expression are known in the art and include many immortalized cell lines available from the American Type Culture Collection (ATCC), including HeLa cells, Chinese hamster ovary (CHO) cells, baby hamster kidney (BHK) cells, and a number of other cell lines. Suitable promoters for mammalian cells are also known in the art and include viral promoters such as that from Simian Virus 40 (SV40), Rous sarcoma virus (RSV), adenovirus (ADV), and bovine papilloma virus (BPV). Mammalian cells may also require terminator sequences and poly A addition sequences; enhancer sequences which increase expression may also be included, and sequences which cause amplification of the gene may also be desirable. These sequences are known in the art.

It will be understood that not all vectors, expression control sequences and hosts will function equally well to express the polynucleotide sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the nucleic acid molecules of this invention on fermentation or in large scale animal culture.

The polypeptides may be detected using methods known in the art that are specific for the polypeptides. These detection methods may include use of specific antibodies, formation of an enzyme product, or disappearance of an enzyme substrate. An enzyme assay may be used to determine the activity of the polypeptide. Resistin can be determined using the immunoassay procedure described by Steppan et al., Nature 409: 307-12, 2001. The human syntaxin binding protein 2 may be detected by its ability to bind to syntaxins 1A, 2 and 3 but not to syntaxin 4 (Katagiri et al., J. Biol. Chem. 270: 4963-6, 1995).

Antibodies

According to the invention, the human resistin or human syntaxin binding protein 2 polypeptides produced according to the method of the present invention may be used as an immunogen to generate any of these antibodies. Such antibodies include but are not limited to polyclonal, monoclonal, chimeric, single chain, Fab fragments, and a Fab expression library.

Various hosts may be used and include but are not limited to goats, rabbits, rats, mice, humans, and others. These hosts may be immunized by injection with the polypeptides of the present invention or any fragment or oligopeptide thereof which has immunogenic properties (e.g., 5-10 peptide fragments with immunogenic properties). Various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are especially preferable in humans.

Monoclonal antibodies to the said polypeptides and peptides of the present invention may be prepared using any technique which provides for the production of antibody molecules by continuous cell lines in culture. These include, but are not limited to, the hybridoma technique, the human B-cell hybridoma technique, and the EBV-hybridoma technique. See, e.g., Kohler, et al., 1975, Nature, 256: 495-497; Kozbor et al., 1985, J. Immunol. Methods 81: 31-42; Cote et al., 1983, Proc. Natl. Acad. Sci. USA 80: 2026-2030; Cole et al., 1984, Mol. Cell Biol. 62: 109-120.

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between the polypeptide(s) of the present invention and its specific antibody.

Antibodies may be conjugated to a solid support suitable for a diagnostic assay (e.g., beads, plates, slides or wells formed from materials such as latex or polystyrene) in accordance with known techniques, such as precipitation. Antibodies may likewise be conjugated to detectable groups such as radiolabels (e.g. $^{35}S$, $^{125}I$, $^{131}I$), enzyme labels (e.g., horseradish peroxidase, alkaline phosphatase), and fluorescent labels (e.g., fluorescein) in accordance with known techniques.

Microarrays and Kits

The microarray generally contains a large number of single-stranded nucleic acid sequences, fixed to a solid support, wherein at least one of which is a nucleic acid hybridizing to at least one 20 (and/or larger) nucleotide fragment unique to a (forward or reverse strand) noncoding region of SEQ ID NO:3 or 4. The fragment may hybridize to the coding and noncoding region. Alternatively larger fragments, e.g., of about 50, 70, 75, 150, 500, 600, 750, 800, 850, 900 or about 950 nucleotides in length may be used. In yet another embodiment, BAC or YAC arrays may be used containing full length cDNA or genomic sequences. The kit may also comprise coding sequences of SEQ ID NO: 3 or 4.

In order to produce oligonucleotides to a known sequence for a microarray or detection kit, the nucleic acid of interest is typically examined using a computer algorithm which starts at the 5' or at the 3' end of the nucleotide sequence. Typical algorithms will then identify oligomers of defined length that are unique to said nucleic acid, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers may be synthesized at designated areas on a solid support using a light-directed chemical process or prepared elsewhere and then deposited on the solid support. The solid support may be paper, nylon or other type of membrane, filter, chip, glass slide or any other suitable solid support.

The microarrays of the present invention may be used to identify nucleic acids encoding resistin and/or syntaxin.

In another embodiment, the invention is directed to a kit comprising at least one nucleic acid comprising at least 20 nucleotides hybridizing under stringent conditions to a noncoding region of the nucleic acid of the present invention. The kit may also comprise a polynucleotide fragment encompassing the coding region of resistin or syntaxin. In a more specific embodiment, the kit comprises a probe or primer comprising 50, 70, 75, 150, 500, 600, 750, 800, 850, 900 or about 950 nucleotides in length may be used. In yet another embodiment, BAC, PAC or YAC arrays may be used containing full length genomic sequences. The nucleic acid may act as a probe or primer and may be labeled with a detectable label. The detectable label may, for example, be a radioactive label, fluorescer, antibody or enzyme. The kit may further comprise the label. Alternatively, the kit may comprise a microarray. The probes or primers of the present invention may act as a primer to synthesize further nucleic acid probes.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments disclosed herein. Examples of such assays can be found in Chard, 1986, An Introduction to Radioimmunoassay and Related Techniques, Elsevier Science Publishers, Amsterdam, The Netherlands; Bullock, G. R. et al., Techniques in Immunocytochemistry, Academic Press, Orlando, Fla. Vol. 1 (1982), Vol. 2 (1983), Vol. 3 (1985); Tinsel, Practice and Theory of Enzyme Immunoassays: Laboratory Techniques in Biochemistry and Molecular Biology, Elsevier Science Publishers, Amsterdam, The Netherlands (1985).

Therapeutic Uses

Antisense Oligonucleotides and Mimetics

The invention is further directed to antisense oligonucleotides and mimetics to these polynucleotide sequences. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature polypeptides of the present invention, is used to design an antisense RNA oligonucleotide of from about 10 to 40 base pairs in length. A DNA oligonucleotide is designed to be complementary to a region of the gene involved in transcription or RNA processing (triple helix (see Lee et al., Nucl. Acids Res., 6:3073 (1979); Cooney et al, Science, 241:456 (1988); and Dervan et al., Science, 251: 1360 (1991)), thereby preventing transcription and the production of said polypeptides. As defined herein, a "mimetic" is an oligonucleotide having non-naturally occurring portions which function similarly to naturally occurring oligonucleotides and may include peptide-nucleic acids (PNAs). Modifications may occur at the phosphate linkage (e.g., methylphosphonates, phosphothioates) or sugar linkage, cyclobutyl moieties in place of the pentofuranosyl sugar or at the purine or pyrimidine bases themselves as described in US 2004/0214325.

The antisense oligonucleotides or mimetics of the present invention may be used to decrease levels of a polypeptide. For example, human resistin inhibits actions of insulin. Therefore, the human resistin antisense oligonucleotides of the present invention could be used to treat insulin-resistant forms of type 2 diabetes. Human syntaxin binding protein 2 plays a role in vesicle trafficking, thus its antisense sequences may be used to treat endocrine tumors such as insulinomas from which hormones such as insulin are secreted in health-threatening excess.

The antisense oligonucleotides of the present invention may be formulated into pharmaceutical compositions. These compositions may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention, the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$ as found to be effective in in vitro and in vivo animal models.

In general, dosage is from 0.01 ug to 10 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 10 g per kg of body weight, once or more daily, to once every 20 years.

Gene Therapy

As noted above, human resistin inhibits actions of insulin, and human syntaxin binding protein 2 plays a role in secretory vesicle trafficking. Therefore, the human resistin gene may be used to modulate conditions in which insulin is secreted in excess, as in functional insulinomas. The human syntaxin binding protein 2 gene may be used to stimulate secretory vesicle release from hypofunctional endocrine tissues such as the pancreas islet cells in juvenile diabetes.

As described herein, the polynucleotide of the present invention may be introduced into a patient's cells for therapeutic uses. As will be discussed in further detail below, cells can be transfected using any appropriate means, including viral vectors, as shown by the example, chemical transfectants, or physico-mechanical methods such as electroporation and direct diffusion of DNA. See, for example, Wolff, Jon A, et al., "Direct gene transfer into mouse muscle in vivo," Science, 247, 1465-1468, 1990; and Wolff, Jon A, "Human dystrophin expression in mdx mice after intramuscular injection of DNA constructs," Nature, 352, 815-818, 1991. As used herein, vectors are agents that transport the gene into the cell without degradation and include a promoter yielding expression of the gene in the cells into which it is delivered. As will be (1) (2) discussed in further detail below, promoters can be general promoters, yielding expression in a variety of mammalian cells, or cell specific, or even nuclear versus cytoplasmic specific. These are known to those skilled in the art and can be constructed using standard molecular biology protocols. Vectors have been divided into two classes: a) Biological agents derived from viral, bacterial or other sources; b) Chemical physical methods that increase the potential for gene uptake, directly introduce the gene into the nucleus or target the gene to a cell receptor.

Biological Vectors

Viral vectors have higher transaction (ability to introduce genes) abilities than do most chemical or physical methods to introduce genes into cells. Vectors that may be used in the present invention include viruses, such as adenoviruses, adeno associated virus (AAV), vaccinia, herpesviruses, baculoviruses and retroviruses, bacteriophages, cosmids, plasmids, fungal vectors and other recombination vehicles typically used in the art which have been described for expression in a variety of eukaryotic and prokaryotic hosts, and may be used for gene therapy as well as for simple protein expression. Polynucleotides are inserted into vector genomes using methods well known in the art.

Retroviral vectors are the vectors most commonly used in clinical trials, since they carry a larger genetic payload than other viral vectors. However, they are not useful in non-proliferating cells. Adenovirus vectors are relatively stable and easy to work with, have high titers, and can be delivered in aerosol formulation. Pox viral vectors are large and have several sites for inserting genes, they are thermostable and can be stored at room temperature.

Examples of promoters are SP6, T4, T7, SV40 early promoter, cytomegalovirus (CMV) promoter, mouse mammary tumor virus (MMTV) steroid-inducible promoter, Moloney murine leukemia virus (MMLV) promoter, phosphoglycerate kinase (PGK) promoter, and the like. Alternatively, the promoter may be an endogenous adenovirus promoter, for example the E1 a promoter or the Ad2 major late promoter (MLP). Similarly, those of ordinary skill in the art can construct adenoviral vectors utilizing endogenous or heterologous poly A addition signals.

Plasmids are not integrated into the genome and the vast majority of them are present only from a few weeks to several months, so they are typically very safe. However, they have lower expression levels than retroviruses and since cells have the ability to identify and eventually shut down foreign gene expression, the continuous release of DNA from the polymer to the target cells substantially increases the duration of functional expression while maintaining the benefit of the safety associated with non-viral transfections.

Chemical/Physical Vectors

Other methods to directly introduce genes into cells or exploit receptors on the surface of cells include the use of liposomes and lipids, ligands for specific cell surface receptors, cell receptors, and calcium phosphate and other chemical mediators, microinjections directly to single cells, electroporation and homologous recombination. Liposomes are commercially available from Gibco BRL, for example, as LIPOFECTIN¨ and LIPOFECTACE¨, which are formed of cationic lipids such as N-[1-(2,3 dioleyloxy)-propyl]-n,n,n-trimethylammonium chloride (DOTMA) and dimethyl dioctadecylammonium bromide (DDAB). Numerous methods are also published for making liposomes, known to those skilled in the art.

For example, Nucleic acid-Lipid Complexes—Lipid carriers can be associated with naked nucleic acids (e.g., plasmid DNA) to facilitate passage through cellular membranes. Cationic, anionic, or neutral lipids can be used for this purpose. However, cationic lipids are preferred because they have been shown to associate better with DNA that, generally, has a negative charge. Cationic lipids have also been shown to mediate intracellular delivery of plasmid DNA (Felgner and Ringold, Nature 337:387 (1989)). Intravenous injection of cationic lipid-plasmid complexes into mice has been shown to result in expression of the DNA in lung (Brigham et al., Am. J. Med. Sci. 298:278 (1989)). See also, Osaka et al., J. Pharm. Sci. 85(6):612-618 (1996); San et al., Human Gene Therapy 4:781-788 (1993); Senior et al., Biochemica et Biophysica Acta 1070:173-179 (1991); Kabanov and Kabanov, Bioconjugate Chem. 6:7-20 (1995); Remy et al., Bioconjugate Chem. 5:647-654 (1994); Behr, J-P., Bioconjugate Chem 5:382-389 (1994); Behr et al., Proc. Natl. Acad. Sci., USA 86:6982-6986 (1989); and Wyman et al., Biochem. 36:3008-3017 (1997).

Cationic lipids are known to those of ordinary skill in the art. Representative cationic lipids include those disclosed, for example, in U.S. Pat. No. 5,283,185; and e.g., U.S. Pat. No. 5,767,099. In a preferred embodiment, the cationic lipid is N.sup.4-spermine cholesteryl carbamate (GL-67) disclosed in U.S. Pat. No. 5,767,099. Additional preferred lipids include N4 Dspermidine cholestryl carbamate (GL-53) and 1-(N4-spermind)-2,3-dilaurylglycerol carbamate (GL-89).

The vectors of the invention may be targeted to specific cells by linking a targeting molecule to the vector. A targeting molecule is any agent that is specific for a cell or tissue type of interest, including for example, a ligand, antibody, sugar, receptor, or other binding molecule.

Invention vectors may be delivered to the target cells in a suitable composition, either alone, or complexed, as provided above, comprising the vector and a suitably acceptable carrier. The vector may be delivered to target cells by methods known in the art, for example, intravenous, intramuscular, intranasal, subcutaneous, intubation, lavage, and the like. The vectors may be delivered via in vivo or ex vivo applications. In vivo applications involve the direct administration of an adenoviral vector of the invention formulated into a composition to the cells of an individual. Ex vivo applications involve the transfer of the adenoviral vector directly to harvested autologous cells which are maintained in vitro, followed by readministration of the transduced cells to a recipient.

In a specific embodiment, the vector is transfected into antigen-presenting cells. Suitable sources of antigen-presenting cells (APCs) include, but are not limited to, whole cells such as dendritic cells or macrophages; purified MHC class I molecule complexed to beta2-microglobulin and foster antigen-presenting cells. In a specific embodiment, the vectors of the present invention may be introduced into T cells or B cells using methods known in the art (see, for example, Tsokos and Nepom, 2000, J. Clin. Invest. 106:181-183).

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. An isolated nucleic acid molecule consisting of between 200-10000 contiguous nucleotides in a sequence segment of a 3'-noncoding region shown in sequence segment 1-19610 of SEQ ID NO:3.

2. The isolated nucleic acid molecule of claim 1, wherein the nucleic acid molecule consists of between 400-3000 contiguous nucleotides in a sequence segment of a 3'-noncoding region shown in sequence segment 1-19610 of SEQ ID NO:3.

3. A kit comprising the isolated nucleic acid molecule of claim 1.

4. The kit according to claim 1, in which the nucleic acid molecule is labeled with a detectable substance.

5. A microarray comprising one or more of the nucleic acid molecules of claim 1.

6. A kit comprising the microarray of claim 5.

7. A microarray comprising one or more of the nucleic acid molecules of claim 2.

8. A kit comprising the microarray of claim 7.

9. A method of detecting the presence of a nucleic acid sequence of SEQ ID NO:3, its complementary sequence or unique fragment thereof in a sample, said method comprising contacting the sample with the nucleic acid molecule of claim 1 and determining whether the nucleic acid molecule binds to said nucleic acid sequence in the sample.

10. An isolated nucleic acid molecule consisting of 40-10000 contiguous nucleotides in a sequence segment of a 3'-noncoding region shown in sequence segment and 1-19610 of SEQ ID NO:3.

11. The isolated nucleic acid molecule of claim 10, wherein said nucleic acid molecule consists of 40-800 contiguous nucleotides in a sequence segment of a 3'-noncoding region shown in sequence segment and 1-19610 of SEQ ID NO:3.

12. A kit comprising the isolated nucleic acid molecule of claim 10.

13. The kit according to claim 10, in which the nucleic acid molecule is labeled with a detectable substance.

14. A microarray comprising one or more of the nucleic acid molecules of claim 10.

15. A kit comprising the microarray of claim 10.

16. A microarray comprising one or more of the nucleic acid molecules of claim 11.

17. A kit comprising the microarray of claim 16.

18. A method of detecting the presence of a nucleic acid sequence of SEQ ID NO:3, its complementary sequence or unique fragment thereof in a sample, said method comprising contacting the sample with the nucleic acid molecule of claim 10 and determining whether the nucleic acid molecule binds to said nucleic acid sequence in the sample.

* * * * *

SEQUENCE LISTING

```
<160> NUMBER OF SEQ ID NOS: 5

<210> SEQ ID NO 1
<211> LENGTH: 108
<212> TYPE: PRT
<213> ORGANISM: Homo sapiens

<400> SEQUENCE: 1

Met Lys Ala Leu Cys Leu Leu Leu Leu Pro Val Leu Gly Leu Leu Val
1               5                   10                  15

Ser Ser Lys Thr Leu Cys Ser Met Glu Glu Ala Ile Asn Glu Arg Ile
            20                  25                  30

Gln Glu Val Ala Gly Ser Leu Val Phe Arg Ala Ile Ser Ser Ile Gly
        35                  40                  45

Leu Glu Cys Gln Ser Val Thr Ser Arg Gly Asp Leu Ala Thr Cys Pro
    50                  55                  60

Arg Gly Phe Ala Val Thr Gly Cys Thr Cys Gly Ser Ala Cys Gly Ser
65                  70                  75                  80

Trp Asp Val Arg Ala Glu Thr Thr Cys His Cys Gln Cys Ala Gly Met
                85                  90                  95

Asp Trp Thr Gly Ala Arg Cys Cys Arg Val Gln Pro
            100                 105


<210> SEQ ID NO 2
<211> LENGTH: 593
<212> TYPE: PRT
<213> ORGANISM: Homo sapiens

<400> SEQUENCE: 2

Met Ala Pro Ser Gly Leu Lys Ala Val Val Gly Glu Lys Ile Leu Ser
1               5                   10                  15

Gly Val Ile Arg Ser Val Lys Lys Asp Gly Glu Trp Lys Val Leu Ile
            20                  25                  30

Met Asp His Pro Ser Met Arg Ile Leu Ser Ser Cys Cys Lys Met Ser
        35                  40                  45

Asp Ile Leu Ala Glu Gly Ile Thr Ile Val Glu Asp Ile Asn Lys Arg
    50                  55                  60

Arg Glu Pro Ile Pro Ser Leu Glu Ala Ile Tyr Leu Leu Ser Pro Thr
65                  70                  75                  80

Glu Lys Ser Val Gln Ala Leu Ile Lys Asp Phe Gln Gly Thr Pro Thr
                85                  90                  95

Phe Thr Tyr Lys Ala Ala His Ile Phe Phe Thr Asp Thr Cys Pro Glu
            100                 105                 110

Pro Leu Phe Ser Glu Leu Gly Arg Ser Arg Leu Ala Lys Val Val Lys
        115                 120                 125

Thr Leu Lys Glu Ile His Leu Ala Phe Leu Pro Tyr Glu Ala Gln Val
    130                 135                 140
```

-continued

```
Phe Ser Leu Asp Ala Pro His Ser Thr Tyr Asn Leu Tyr Cys Pro Phe
145                 150                 155                 160

Arg Ala Glu Glu Arg Thr Arg Gln Leu Glu Val Leu Ala Gln Gln Ile
                165                 170                 175

Ala Thr Leu Cys Ala Thr Leu Gln Glu Tyr Pro Ala Ile Arg Tyr Arg
            180                 185                 190

Lys Gly Pro Glu Asp Thr Ala Gln Leu Ala His Ala Val Leu Ala Lys
        195                 200                 205

Leu Asn Ala Phe Lys Ala Asp Thr Pro Ser Leu Gly Glu Gly Pro Glu
    210                 215                 220

Lys Thr Arg Ser Gln Leu Leu Ile Met Asp Arg Ala Ala Asp Pro Val
225                 230                 235                 240

Ser Pro Leu Leu His Glu Leu Thr Phe Gln Ala Met Ala Tyr Asp Leu
                245                 250                 255

Leu Asp Ile Glu Gln Asp Thr Tyr Arg Tyr Glu Thr Thr Gly Leu Ser
            260                 265                 270

Glu Ala Arg Glu Lys Ala Val Leu Leu Asp Glu Asp Asp Asp Leu Trp
        275                 280                 285

Val Glu Leu Arg His Met His Ile Ala Asp Val Ser Lys Lys Val Thr
    290                 295                 300

Glu Leu Leu Arg Thr Phe Cys Glu Ser Lys Arg Leu Thr Thr Asp Lys
305                 310                 315                 320

Ala Asn Ile Lys Asp Leu Ser Gln Ile Leu Lys Lys Met Pro Gln Tyr
                325                 330                 335

Gln Lys Glu Leu Asn Lys Tyr Ser Thr His Leu His Leu Ala Asp Asp
            340                 345                 350

Cys Met Lys His Phe Lys Gly Ser Val Glu Lys Leu Cys Ser Val Glu
        355                 360                 365

Gln Asp Leu Ala Met Gly Ser Asp Ala Glu Gly Glu Lys Ile Lys Asp
    370                 375                 380

Ser Met Lys Leu Ile Val Pro Val Leu Leu Asp Ala Ala Val Pro Ala
385                 390                 395                 400

Tyr Asp Lys Ile Arg Val Leu Leu Leu Tyr Ile Leu Leu Arg Asn Gly
                405                 410                 415

Val Ser Glu Glu Asn Leu Ala Lys Leu Ile Gln His Ala Asn Val Gln
            420                 425                 430

Ala His Ser Ser Leu Ile Arg Asn Leu Glu Gln Leu Gly Gly Thr Val
        435                 440                 445

Thr Asn Pro Gly Gly Ser Gly Thr Ser Ser Arg Leu Glu Pro Arg Glu
    450                 455                 460

Arg Met Glu Pro Thr Tyr Gln Leu Ser Arg Trp Thr Pro Val Ile Lys
465                 470                 475                 480

Asp Val Met Glu Asp Ala Val Glu Asp Arg Leu Asp Arg Asn Leu Trp
                485                 490                 495

Pro Phe Val Ser Asp Pro Ala Pro Thr Ala Ser Ser Gln Ala Ala Val
            500                 505                 510

Ser Ala Arg Phe Gly His Trp His Lys Asn Lys Ala Gly Val Glu Ala
        515                 520                 525

Arg Ala Gly Pro Arg Leu Ile Val Tyr Val Met Gly Gly Val Ala Met
    530                 535                 540

Ser Glu Met Arg Ala Ala Tyr Glu Val Thr Arg Ala Thr Glu Gly Lys
545                 550                 555                 560

Trp Glu Val Leu Ile Gly Ser Ser His Ile Leu Thr Pro Thr Arg Phe
                565                 570                 575
```

-continued

```
Leu Asp Asp Leu Lys Ala Leu Asp Lys Lys Leu Glu Asp Ile Ala Leu
            580                 585                 590

Pro


<210> SEQ ID NO 3
<211> LENGTH: 38587
<212> TYPE: DNA
<213> ORGANISM: Homo sapiens

<400> SEQUENCE: 3

gtgcctctag aggatcccca tgcacagatt agaaaggtga gtcttggccg ggcagggtgg      60

ctcgtgcctg tcatcccagc gctgtaggac gccgaggtgg gtggatcacc tgccaggagt     120

ttaagaccat cctggtcaac atggcgaaac ccctctctac taaaaataca gaaattagcc     180

agtcatgatg gcgggcgcct gtaatcccag ctatttgaga ggctgaggtg ggagaatcac     240

ttgaacccag gaggcggagg ttgcagtgag ctgagatcgc gcactgcact ccagcctggg     300

cgacagagtg attctgtctc aacaaaataa ataaataaac aaacaaacaa ataaataagg     360

gtgagtcttg ggctgcaggg tatggggcac caaaatgagg taccggtccc caggcacaga     420

ctcaggatgg ggaacctggg gtgagaaggg agggtgcaga ctcagagggc tgccgggaac     480

tgggctcctt ctccccgccc catcccctga cccaaagcct tttgctccag caactgggct     540

ccaggggagc ccaccagccg gagccagggc gaggactgcg tgatgatgcg gggctccggt     600

cgctggaacg acgccttctg cgaccgtaag ctgggcgcct gggtgtgcga ccggctggcc     660

acatgcacgc cgccagccag cgaaggttcc gcggagtcca tgggacctga ttcaagacca     720

gaccctgacg gccgcctgcc cacccccctct gcccctctcc actcttgagc atggatacag    780

ccaggcccag agcaagaccc tgaagacccc caaccacggc ctaaaagcct ctttgtggct     840

gaaaggtccc tgtgacattt tctgccaccc aaacggaggc agctgacaca tctcccgctc     900

ctctatggcc ctgccttccc aggagtacac cccaacagca ccctctccag atgggagtgc     960

ccccaacagc accctctcca gatgagagta caccccaaca gcaccctctc cagatgagag    1020

tacaccccaa cagcaccctc tccagatgag agtacacccc aacagcaccc tctccagatg    1080

cagccccatc tcctcagcac cccaggacct gagtatcccc agctcaggtg gtgagtcctc    1140

ctgtccagcc tgcatcaata aaatggggca gtgatggcct ccccacatttg tccccttctt   1200

ggaggcctgg ctgggtctgg tctctgggtg tggcacatgg gagctgggaa ttccagagtc    1260

tgatgcctga gaccaccttt gaaagttggg acatcagatc tttggccggg tgtggtggcc    1320

catgcctgta attccagcac tttgggaagt caaggcaggc gaatcatctg aggtcaggag    1380

ttcaagacca gcctggccaa catggcaaaa ccccgtctct attaaaaata caaaaattca    1440

gccgggcacg gtggctcacg cctgtaatcc cagcactttg ggaggccaag gcaggcggat    1500

cacaaggtca ggagatcgag accatcctgg ctaacacggt gaaactccgt ctctactaaa    1560

aatacaaaaa attagccggg cgtggcggcg tgtgcctgta gtcccagctg ctggggaggc    1620

tgaggcagga gaatggcgtg aacccgggag gtggagcttg cagtgagccg agattgcgcc    1680

actgcactcc agcctgggcg acagagcgag actccatctc aaaaaaaaaa aaaaaaacaaa   1740

aacacaaaaa ttcgctgggc gtggtggtgc acacccgtaa tcctagctac tcaggaggct    1800

gaggcaggag aagtgcttga acctgggagg tggaggttgc aatgatctga gatcacgcca    1860

ctgtgacaga gcgagacccc aactaaataa atttaaaaag aaagaaagaa aattgggagc    1920

aagcagatgt ggtggctcat gcctgtaatc ccagcacttt gggaggctga attgagccga    1980
```

-continued

```
tcacttgaga ccaggagttc gagaccagcc tggccaacat agtgaaaccc cgtctctact   2040

aaaaaaaaaa tacaaaaatt agccaggcac ggtggcatgt gcctataatc ccagctactc   2100

gggaggctga ggcaggagaa tcacttgaac ctgggaggca gaggttgcag tgagccagga   2160

tcgtgctact gcactccagc ctgggtaaca gagtgagatt gcatgtcaaa aaaaaaaaaa   2220

agaagaaaaa agaaacaaat tgaggagcaa ctgaagtaga attcgatctc ccgtttttat   2280

tttttcctgc tctatgacac ggagaatgtg caggacatga agcctctgag gtccaatggc   2340

cccttggaat actgtagggg aaggcggtgg atcaccctga ggccgggagg gcgtgagttg   2400

actcatggaa gtacccagag cagggcttag tacacagaag gcactcagta agtgctggct   2460

ggctggacag gctgatgggg agtgggcccg gtcaaccgga ggccatttcg ggtctggagg   2520

tgttaaccct actcagggtc tgggaggctg aggtggcacc agcctcacgc tcggccaagg   2580

tcgacccatg ccggaggcca cgggagggag gccaggagca cagggtcccc tctccacact   2640

cctctaccag tggctcaggc caacactggg gtcattgcac ctcttccctt tcccctgaca   2700

acacctccag gtccaagacc ataagaaatg ccagtgggct ctgctgtcaa acggcgctca   2760

caatcactca ctgctcaccc cttctgccac tgcctcgact ggagcagtca cctccgcccg   2820

gggctctctc ttcactgccc cctttccaga agtttcctcc agctcagata aaaggccaaa   2880

gccagctgcg cacagtggct catgcctgtc atcccagcgc tttgggaggc tgaggtggga   2940

ggactgcttg agttcaggag tttgaggcca gcctgggcaa catagtgagg ccccatctct   3000

acaaaaaata caaaaactag aggtgtagtg atgggcaact tggtcccagc tgcttgggag   3060

gccgaggtgg gaggattgtg cccctgctct cagcctgggc gacagtgaga acctgtctca   3120

aaaaaaaaga agaagaaaag agaaaaagcc agccaggtgc ggtggctcac gcctgtaatc   3180

ctagcacttt gggaggccaa ggcgggcaga tcacttgagg tcaggagttc cagaccagcc   3240

tggccaacat ggtgaaaccc cgtctccact aaaaatacaa aaattagctg ggtgtggtgg   3300

cggatgccta tagtcccaac tattcaggag gctgaagcag gagaattgct tgaacccagg   3360

aggctgagat ctgagatcgc accactgcac tccagcctgg gcgacagagt gagactccat   3420

ctctaaataa taataataat aataattaat ctgtgtgacc atgggcacat gacttctttt   3480

ggaacctgcc tgtgaaatga gctgatgctg cttgcccagc tcaccaaggg ctggtgcctg   3540

gctcctcctc ctcctcttcc tctcacccac ccacctggag ggtccagggg aagaccttcc   3600

ttgcagccca gagcaccgta agttagagct gctgtgatca gaagctgccg aaccacaggc   3660

tcttctttct cttcatcctc ccttgcccca accccgggcc cagcctcata accctacagc   3720

ttgttcaaac gttttccctt ctcctcaagc cccctaactc accctcggtg gccggtgggg   3780

atggggcgtg ggaacagacc ctgggccctg cactcccagc ttacaaattc ccgcagcccc   3840

tcttcctccc tcccgatttc tctgacatcc ctcacagccc cgcctctgga cagaagaatg   3900

gcccctgccc tggccggccc tggaagcccc tctcgccagg gtctcagagg acctgcctgg   3960

ggctgcttag cccaaagcgt cctgcatttt gctctgaaat ccagcttctc agacaccatg   4020

ttcccctccc tccgtccccc atccaggact gtggtttctg tgtctgtgca gacgcccaga   4080

cctccctcca gaactccaga ccccaaaccc caagacctgt gcatctgctg gccccctaga   4140

cgcctccccc tcattccaga ttcaggctat catcctgccc aagccctctc ccggcgcctc   4200

cctccacctc caacagccaa cagctattcc aggatcagcc ctggggctat gtgtggtggt   4260

tgctcaatgg tttcattcat cctagagacg ccaccttctc cccagtgtgc tgaagcccac   4320

cctgctcaat gcctcttgct aggatggctg agactgccct gaccaagccc tcagccctgg   4380
```

-continued

```
tccaccaggc agtccaacag agcatcctaa acaaatctag aggtgacacc gacccctttg   4440
gcccttctca taaccagtga ggggagccca gctgacagtc cctgcagttc cttttctgaa   4500
cagacctgtc tgttcacatt ctggggggcg gtggaaagga agcagggaag attggatcat   4560
ggttcccccca aaaaatctgg aagaactttc cttgggggag aggaggagtt atcaggaacc   4620
aagtgtggtg aacaaaaagg gaaaggaaaa ttgcctgagg tgtaatacat tacttttttt   4680
ttcttttttta agacagggtc tcactctgtt gctcaggctg gagtgccagt ggtgtgatct   4740
tggctcactt caacctccgc ctcccaggtt taagtgatcc tcctgcctta gcctcccaag   4800
tagctgggat tacaggtgcc tgccaccacg cccagctaat ttttgtattt ttagtaaaga   4860
tgggttttgc catgttgacc aggttggtct caaacttccg gcctcaagtg atctgcccac   4920
ctcggcctct caaagtgctg ggattacaga cataagtcgc cacgcctggc cttatttcaa   4980
attcttttag acaaggtctc actatgttgc ccaggctgga caccaacccc tggcctcaag   5040
cgatccttct gcctcggcct cctgaatagc tgggactcca ggtgtgcacc actgcacccc   5100
acttatttta aaattttttt aacaagggaa atgtgtttgt atcatcctgg actttaaaat   5160
taactttaaa gtattgacca gactggccaa cacagtgaaa cctcatctct actaaaaata   5220
caaaaaatta ggtagctggg actacaggaa tgcacctcca tgcccagcta atttttgtat   5280
ttttagtaga gacagggttt caccatattg gccaggctgg ctcgaactcc tgacctcgtg   5340
atccgcctgc ctcggcctcc caaagtgctg ggattatagg cgtgagccac cgcgcctgac   5400
ctttttgttt tttagatgga gtttcgctct tgttgcccag gctggagtgc aatggtgcaa   5460
tctcggctca ctgcaacctc cacctcccgg gttggagcga ttctcctgcc tcagcctccc   5520
aagtagctgg gattacaggc atgtgccacc acacccggct aatgttttct atttttagta   5580
gagacggggt tttgccatgt tagccaggct ggtctcgaac tcctgacttc aggtgatcca   5640
cctgcctcag cctcccaaag tgctgggatt acaggcgtga gccaccgcac gtggcccctc   5700
ctggtgattc tgataccta aagcctgcat ctcaatctaa ggtccccagg aatcccctgg   5760
gggcctcgct aaaatgcacc ctcagattca gcagctctgg ggtgggcctg agactgcatt   5820
atggaccaac tcccagttga tgctgctact gctgatctac agaacacact ttgatttggc   5880
tcacgcctgt aaccccagca cttacggagg ccaaggtgga aggattgctt gaggccaaga   5940
gtttgagacc agcctgggca acctaataag agcccccatc tctacaaaaa ttttttaaaa   6000
attagctggg catggctggg cgccatggct cacgcctgta atcccagcac tttgggaagc   6060
cgaggtgggc agatcacgag gtgaggagat cgagaccatc ctggctaaca tggtgaaacc   6120
ccgtctctac taaaaatacg aaaaattagc caggtgtggt ggtgggcacc tgtagttcca   6180
gctactcggg aggctggggc aggagaatga catgaacccg ggaggcggag cttgcagtga   6240
gccgaagccg agatgctgcc actgcactcc agcctgggcg acagaacaaa accctgtctc   6300
tgaaaaatat aataaatgag ggaagaaggc aaacaatctc cctctgcctg ttttctaggc   6360
acacggtgac acccactcct ttacatgttg tctgtggttg cattcagtac atcagcggag   6420
taatggggca agagcacatg gcggcacagc agtggctcac gcctgtaatc ccagcacttt   6480
gggaggctga agtgggcgga tcacctgaga tgaggagttc gagaccagcc tgaccaacat   6540
ggtgaaaccc catctctact aaaaatacaa aaattagccg ggtgtggtgg gaggcacctg   6600
taatcccagc tacttgggaa gctgaggcag gagaatcacg tgaacccaag gtggaggttt   6660
gcagtgaggt gagatggtgc cactgcactc cagcctgggc gacagagcaa gactctatct   6720
caacaaataa aaaaaataat aataaagacc acatggcata aaatattgcc catctggcac   6780
```

-continued

```
tttgcgcagt ttgcccaccc ccagtctaaa ggcgtctgtc tcagcctgat gcgtctccca   6840
ggaccccatg cccctccag cctgcagaca gcctccaacc gtgattccag aacctgccag   6900
catttcccac caactccttt tgccgggttt atttctcccc accactcctg gtctcactca   6960
accccccaac cctatggcca gacccgcccc cactctactg taaacacatt cggacctggc   7020
ctccctcccc agcctggggc agggctgtgg ctcaaggtac tgagtggatc taaggccgcc   7080
acacaagaca caagacacac gtggggaggg gctctctgta tcctttatct ccggcagggt   7140
cagcggccct ccagggcccg gtctcgagcg atgactgcct cctcgaactt gatcatgagc   7200
gtggtgccct tgtgccagtg cgccgtgacc ttggcaggga agccgctgtg tgtgagcacc   7260
gcctccacga tgcccgccgt gaagctggcg cagttgagcg tgctgttctc cttgggcacg   7320
gagatgtagg tgttgatgag cggctcgcgc tcgatgatgt agaaggtgcg cgcgtcatcg   7380
ttggcctgct ccagcttgtc cgcctccttg ccgaagagcg ccttccacac ggcgcccttg   7440
acgaagagca acgcgcctag caccttggtc tcacgccggg caccctttc gcgcgccacc   7500
agcgcatcca gcacgcgcgc gcccacctgg cggcccagcg cggccaggcg cgactgcagc   7560
tcggccacgg agaagacgcg gctctggcag tgctgtacca gctcggagaa cagcagtgcg   7620
aaggcgctca ggctcacctc ggtgcgcggc cgcgccagcg cgcgctccag cagcgccgac   7680
ttcccgcgcg tgaagcgcgc ctccatgccg ccgccaccct gcggggagac caggaagtgc   7740
aggtgtcagg ggcaatggga aggggagcag gccgggagga aaggagggag aaccgcgagg   7800
ggccctggga caccctcgac ccatgccact gttgtgtgct ccagtgccga cttcccactt   7860
gcaaagagat gcgcgtaaaa cacgcctcga ttacacgtaa ccagataaat caagggaggg   7920
gggagtctta taccctcggc aggcagcggg ctagcgggag tggggacaag gtgggaggag   7980
agacacgagg gggaacagaa gaggaggccg aaaccaccca accctcgggc atgcagacgg   8040
ttcaattgcg aaagcgcctt cctgcccgct ccgccaccta caggagtaac tagaaaacta   8100
gtgtatgggg ggaggggcgt cagatctagg gcagggaggt gacaaagatg aggcaccacg   8160
aggggatatg ggcagtcgct cctgccccgc cctgcgctcc agcacagacg accctcggga   8220
actttcctgc cggcccccctg cggaaagcca gagtaaaggg ggtggagggt gggagtgggg   8280
taggagcgtg tcaagaccaa aagccaggag ggttgggggc tttaacaggg gggatccgtg   8340
gggccaggca ggaggggcgg gtaaccccca accccaagcc ctcaggcagg cagctccgat   8400
gtgtcacgca ggaacccttc gtcctttgag acgcggatgg gcctgggttc tgaaggctgg   8460
gaggaggggc ccagaggtgt tgggagcctc ccaccccgt gctctccaga aaggaagctg   8520
gatgctgagc aactgtggtc ctcccatcag ctgtcggtgc ggggagaggg agatggggta   8580
gggggctcct gaagagaaat ggggtgggga gcgggcgccg agacgggatc ggaggggcag   8640
ctgagaaccc gcccccacca tgcatgggga ggtgtgtgga tgctaagccg accccaacga   8700
ggtctgcgtg ggaggtggga gaaccagcgg ggaggggtgt cccaggggct ccgggccgcc   8760
cccgccccag catgcagatc cgtccgtggc gagggccctg ggcgcgcgag atgggagagg   8820
gatcgttaag accccaccac cgggctgcga tgggggctga agtgagctga actgccgtag   8880
ggtcagggcc ccgcgaccct cgccccgtac ctctacactg gggagaaacc caccctcctc   8940
gcagcctcct gaggggggcc gaagcgagcg ggctcgggat cgcggacgcc gagaccccag   9000
cccgggaccc acacgcccgc ggggaagggg ccggggagcg gacgaggccc ggcgcgggca   9060
ggggggtggg tagggtctca ccaggaaccg cagcagtctg ctcggccgag ctgctttacg   9120
gcgccgtaaa aggcgctgcg tgcgcaggcg ctcgacgggc caggcgtgtg ggcggggcgc   9180
```

-continued gcgcagcggt gcctgagagc ggccgcaggg gggcgcgcga gtccgcggag ccggacccag 9240
ggacgtggcc cacggccgtg atggctgctc cgcgcgtggc cagggtctcg ctggctctgg 9300
gtggcccacg ctggagggga cgcttgcagg cctagtcacc tgctcagggc gcacgtatga 9360
caatgggcca atgtataccc ttgcacatgg acacacctgt tggcttttcc aggcactcct 9420
atgtccttgg ggatgggttc aattgtctca agtgcatcca tgtggcccgc ggtggctccc 9480
gcctgtaacc ccagcatttt cggaggcgga ggtgggagaa tcacttgagg ccaggagttt 9540
gagaccagcc tggacaacat agctagactc ccacttcttt aaaaaaaatt agccaggtgt 9600
ggtggtgtga acctgtaatc ccatctactc gggaggcgga ggcaagagga tcgcctgagc 9660
ccaggaggtc gaggctgcaa tgagtcatga tcgtaccact gccctccagc ctgggtgata 9720
gagcgagacc ctgtctcaaa aaaacaaaaa caaacaacaa caacaacaaa tcaagtgcat 9780
gcatgagcgg tggacatagt accttagggt catgtacact catggataca tgctcaatgg 9840
catagataca ctcacgggca caattacaca cgtgggtaca cgcttagggc ttgtatatat 9900
ccgtggtccc aggtacactc agggagatgt tgtatgctca ggggcaccca ctctgggaca 9960
cagggaagac acagggaatg agttactcat tcacagatgc acaggtactc acgcagggca 10020
ctcagtctcg cccaccctgg tgccccgggg tcattgtcac gtgcagactc tccctctccc 10080
caggtcccaa aacccctccc cttgccccag taacaggtcc catagcgacg ctgttttccc 10140
ttgactttat ttatcttcat aagtcacaaa atgtgagtgc agagataaat gtctgtgtgc 10200
atgtgccctg agcacacagg gtggcataac tcggcacact cataatgaca cagccgttca 10260
cccagccaca gatagtgaca gggcacacat ggcgacaccc acatgtacgg agataaatct 10320
cccccaccat gacatgggta gacagaaaac acgccgcagt atactctagt atgtttacac 10380
aaacagggag acaggcccgt gcaatgcatg tcaccaacac ccacactcag agtgacatct 10440
gctggaggtg ctcagacaca gccacccacc gtgacatgcc gagactcaca tatgtcacat 10500
gacacaggca tgcatgccac attcactgtg actctcagtc ctattcattc atcacctttc 10560
tgggagatac actgaaatgt ccaccctttg caaaatgcac acacacgcgc acgcacacac 10620
gcacatacac gaacacacgc gcacacacgc acacacacgc acgcaggtgt acacacacac 10680
gagcaactcc gagacactca ttcaccatga ctcgaggttt ttctatacgt gggacgaggg 10740
gcaggttcac actaggctgg gggggggggg tcatttcccg tcttcgttgg caggtgcagc 10800
cccatcttcc aagttgtggc tttggctgcc acaatgtcct ctcatttatt gaggtgagga 10860
ctctggggat ggggagagac ccacagtgag gcagatcccg cccctgggag aggagctggg 10920
gctaaatctg aagccccacc caccctcctc cacctcctgt cggggcgcca acttacgtgg 10980
cattttctgc agcacctcca agattttctg tacctttgtg tcaatgtttt ttatgcctag 11040
ggggcgggga gggttgggtg ggaacagata agtcaagctg cggtggagcc tcaaacaaag 11100
cccccacctt ccttggaagc accccccctg ccccacaccc accctggggt acagcagagc 11160
ccatggattt ggggttccca ggagcctttc aatacccaca gagcaaccca gatggtaaca 11220
cccatcgccc ctccacaact tgagctttgg gagggtagga ccccggcttt ctcctcccct 11280
gaatcccctg cccccagctc agctccgggc attggtgaca aataaccccc atagaaggcg 11340
agactacaca ggcacctgct aatgtcgtct ctaatctatc aatcttgctc ctgaccatgg 11400
tgatgctctg ctgaacggaa tcccagcctc tcttctgtct ctcttcgcat gcttgtacgg 11460
agtttgagac tgagggcatg aaacaggggt gtctgtgcat ccatccctct ccagaccccc 11520
accatgaccc cacgggtctc cctcagaccc tccgctcacc attccaaagc tcccttttaa 11580

-continued

```
agcccagcag ctccttggac atctcagcat ctgttcagga ggggcaggaa aatccttgaa  11640
gcacccaggg agagagagag agaaggacaa gggagaaagt ctaggccccc cagcaccctc  11700
ctcccaagaa gtactcactc ttcaccatga tgaaggctga caggatgatg cagaggacaa  11760
aggccagggc caggaggatg tacaggctca ggatggctct gtacaaccag caggggacct  11820
gggtggagtc tgagggcggc ctgcactggg ctgggactgg agcaaagagg cagcaaagtg  11880
accttgaggg gccagcacca ccactcaaac catcctcact gtctctaaca ccatggacac  11940
ctcgctcctc tcaaaaccat cagcagctgt ggtcatgcag cttgtcatca tcgtcaacaa  12000
cactgccacc accagccacc ctcagcgatc taacaccgtc accatcacag accccctctc  12060
cagcattccc caacattgtc atcatcaaca gacctcatta gcacgtcaac agctgtcacc  12120
tcttccttcc ccatcgcttc ctcccttcca cgcagccccg gggcccctgc agttgcccgc  12180
ccacctgccc cttcccaagg tgatgggatg tgagcaggtg ggtgtctgct caccttggct  12240
cgtgggtcgt gaatgaccac cctttgcatg gtcctgattt ttgaaggcca aggtgatatt  12300
ctcatagtct gggtcatggg cacctgggag gggttggaga tctgctcaga gctctgtggt  12360
gtggagagtg gatccgggat cttgttttac ccaacccttt gcactcaata aattgtaggg  12420
ggtgaaagat aaggagtgag aagctaaaat ctgctttttg gttaagtgga gcgggtgtgt  12480
gagagtttga gtgatcacac cacacacaca tccacacaca catccacaca tcttggaggg  12540
gaaggagccc ccggccccca cctttgaccc cttacctctc ccatctgaac tctccttctt  12600
tttttatttt tattttttac agacagagtc tccctatgtt gcccaggcca gtctccacct  12660
ccagggctca cgcaatcctc ccgcctcagc ctcccaaagt gctaggatta cagacatgag  12720
caaaagcccc cggcccccca atctctcctt cttaacccct cccttccacc tcgagttccc  12780
taaccttgat tcttggctga gaccccctgt ttcttgtccc tgaaggctgg tgcttgcatc  12840
ttgacttcct ggtgcttgta gatttcctcc acttccatgg tccccagccc gcaaatttgt  12900
ccatacacgt ccccgcccac cggaaggtgt gggcagatga ggaaatctgg aggtgggggg  12960
aagaaagagg gggagcagcc tcctcttttc agggatccac gactctcgca ccctggggca  13020
ccctcattcc tgccccgatc aagaggctct tgggagccaa gaggtctcag gaaggaccaa  13080
gaagaaaaac ctctagaccg ggagatggaa ttcgacactc ggaaatgtta caggaagctg  13140
tggtctctgt gtgtgtctgt gtctacctgg atggacctca ccctcctacc tcctctccat  13200
ttcaaaagag aagctgtgac acctcagtgt cccaactttt cgcgtaagag caaccaggct  13260
tggagacagg accccctgggt cccccacac cttcctccct ccagcctcag ctccacccct  13320
cagctccacc cccaagaagt tcttctactt ctacaagtcc ccgtggagga aaagcacaga  13380
tgtgaggcaa cgggaactaa ccactggaac gccacaccca catctgggac tgaggacaga  13440
cccacatcct tccctccctc cccaaatccc ctgcttttat acaaccctgg aggaggctgg  13500
gtgcggtggc tcacgcctgt aatcccagca ctctgggagg ctgaggtggg tggatcatct  13560
gaggtcagga gtttgaaacc agcctggcta acatggtgaa accccgtctc tactaaaaat  13620
acaaaaatta gctgggcgtg gtggcgagcg cctgtaatcc tagctactca ggaggctgag  13680
gcaggagaat cgcttaaacc tgggaggcgg aggctgcagt gagcggagat cacaccattg  13740
cactccagaa tgggtgacaa gagggaaact ctgtctcaaa aaagaaccct ggaggaacag  13800
tttcctctgc acctggaaac tccaggtttc tcattctcat ccatccatct gcttatctac  13860
ccagatactc tctctcacac atgtacacac acaggtctgc acacggacac acatcacaaa  13920
ctcatttgca tactatttgc attgtgacac tcagaaaaat agacacaagc atgcgttcac  13980
```

-continued atgcccgcac tctgtctaga aggtgtctta gttcactttg tgtttatctg atcttgaaaa 14040
ctggggttac aaaaggcaca aagtagctgg gtatggtggc tcgctctgta gtcccagcta 14100
cccaggaggc tgaggtagga ggatcatttg aggccaggag tttgagacca gcgtgagcaa 14160
catagcaaga ccctgtctct ttaaatgttt tttaataatt ttttttgag acagggtttc 14220
actctgttgc ccaggccggg gtgcagcagc gtgatcatgg ctcactgcag ctttgacctc 14280
cctggctcaa gtaatccttc gtcctcggct tcccgagtag ctgaaattac aggtgggcac 14340
gacttcacct ggctaatttt tctccttttt tgagatggag ttttgtgctt gtcacccagg 14400
ctggagtgca atgacgctat ctcagctcac tgcaacctcc gcatcccagg ttcaagtcat 14460
tctcctgcct cagcctccca agtagctggg attacaggca tgcaccacca cccccggcta 14520
attttgtatt tttagtagag acggggtttc cccatgttgg tcaggctggt ctcgaactcc 14580
tgacttcacg tgatctaccc gccttggcct cccaaagtgc tgggattaca agcatcagcc 14640
accgtggccc agtctaattt ttcttatttt ttgtagagat gagggtctca atatgccgtc 14700
caggctggtc ttgatctcct gggttcaact gatcctccag ccttggtctc ccaaagtgct 14760
gggattacag gcatacattt ttatttttat ttttttctgg ccaggtgtgg tggctcacgc 14820
ctgtaatcac agcactttgg gagtctgagg cgggcggatc acctgaggtc aggagttaga 14880
gacaccagcc tgaccaatat gataaaaccc tgtctctact aaaaatgcaa aaattaactg 14940
ggcgtggtgg caggcgcctg taatctcagc cactcgggag gctgagacag gagaatcact 15000
tgaacccggg aggtggaggt tgcagtgagc cgagatcgcg ccattgcact ccagcctggg 15060
caacaagagc aaaactccgt caaaaaaaaa aaaaaaaaaa gaaaaaagaa gaaagaagaa 15120
agaaggaagg aaggaagaag aaaagaagaa aaaacaagta taagactgtc ttatgtgcag 15180
aaagtgatga tgttttggtt aaaaatatgt ggttaaattt cagacaactt gaatgttgag 15240
aaatgagcgt cgagatctgg tgaggataaa gttctgtttc ctaaaatatt gccaaatcct 15300
gtgtctccaa gaaagatcaa tttgataatg acttcatgcc agctgctcca tttggtctta 15360
gaaagaagtc agttactgag ctataggacc gccttctaat ggagcagacg gaccaattgg 15420
atgtgggctc tgccttgatg gacaggcaca gggggtggag ccacagcgtt gcacatttcc 15480
cgggcttggg tggggctgag acgcggctcc aggctctgga cttcctttga gaaaaaggtc 15540
acgctaaacc agaggcccac aagcaatcat gtcatgtggg aaacatctgc aaagctgcct 15600
gaccagcacc cgtccctttc atagggtaac attctcaatt ttcttttaag aaagaaaatg 15660
tgtgctagat ccagcaaacc ataagctagg gattggttta cagtggacaa atgatccaga 15720
cccagccaac cagagtctaa gattgggcag agaggcgggc atttgagcaa gatccagcca 15780
atgaaacgct ggtctgggat ttttattggt ttaaccacgg gggaaaaagc attctctttt 15840
ttttccagcc ctcactaggg ctgccacaat gggaggatgt aatgggagct gtgacaggga 15900
agaatttact tgagagcaaa ggcagtgctg agaaaatcag acccgagagg aagtctgggt 15960
cctggagaca tcatttgaga ccctggttcc aagccatacc tgaacctgtt gttctaaccc 16020
tgggcttgtc agttacacaa acaagaaact tccttttagt tttgcccaag ctagtttgaa 16080
gtggggtctg ttgtacttgc aagcagaaga atcttgcctt ggctggtctc tgtggcccac 16140
gcctgtaatc ccagcacttt ggaaggccga ggcaggtgaa tcacttaagg tcaggaattt 16200
gagaccagcc tggccaaaat ggcgaaatcc ccgtgtctac taaaaataca aaaattagcc 16260
aggagtggtg gtgggcgcct gcaatcccaa ctactcagga ggctgaagca ggagaatcac 16320
ttgaacctgg aggtggaggt tgcagtgagc tgagatcgtg ccactgcact ccagcctgga 16380

-continued caacagagtg agactccatc tcaaaaagga agaagaagaa ggaggaggag gagaaggatg 16440
aggaggagga aggagggagt gaggagggag gagggaggag gatatcttgc ctaccacagg 16500
ggatctaggc attagctatt gaggaaattg aggctctaat agggggtttg cctgtccaca 16560
tcacctgggc agatatgacc tccaagtctg cactctgggg caggagaatg tctatgttgg 16620
aattgaggaa cctgaagaga gccctcttag gtttcagata caggactatt ggatgggggt 16680
ggagacaaat agttctgggg acaatggagc atccccgccc ccaacacaca cacacagcag 16740
taaggggcag ggacacacac aaggcactag actcaccctc tctggccctg gccatgcttc 16800
taactcagtg gtcctgccct acccccatga ccactgtgga gtcaggagag agggtctggg 16860
aagggaatcc ctgggctgga gtctgggtgg ggtccctggc accagaagtg gttgtaatct 16920
ctgctcatgg ccaccagcat cagacagggg gctgggacca tcacaggggg tgggtggcag 16980
tgggaggaga gtccaaaaca tcctgcaaac cagaacctca ctctatcatc tgttgtccag 17040
gtgtgacatt tgagtctggg atccctttca agactaggtg ctaggaattc tgaagtctgt 17100
ggtgggaaat cagggactgg atggcaagac tcctgggtca ggcttcctgt agaactggac 17160
cccgaatcac ctgaatttgt gccccaggga gctgaggcgg gggatgctga ggcttttgcc 17220
cactagaaca ggggtcccca gccaccgggc attgggaacg gggcctcaca gcaggaggtg 17280
agtggtgggc gagcgagaga agcttcatct gtatttacag ccactcccca tcattcgcat 17340
taccacctga gctccacctc ctgtcagacc agcagcagca ttagattctc ataggagcaa 17400
gaatcccatc gtgaactgcg catttgaggg atgtagcttt ctcacttctt ataagaatca 17460
aatgcctggt aatctgtcgc tgtctcccat caccctcagc tgggaccatc tagttgcagg 17520
aacacaagct cagggctccc accgattcca cattatggtg agttgtagaa ttattttatt 17580
ctatattaca atgtcataat aataaaaata aagtgaataa taaatgtaat gcgcttgaat 17640
cacccagaaa ccatccccgc tcccccccta ccccatacac acaccaactg tcttccatga 17700
aaacagtctc tggtgccaaa aaggttgggg atcgctgcac tagggtatca gatacttatc 17760
caggtgcagt ggggactaga gtcagaaatg caagagtctg cctggagcat gtgtgtgttt 17820
gtgtcctgca tcatctctgc ccaccatagt caaatctgcg attctccgtg cattggccgg 17880
gggggtggtg cctttctgtg tccaagagtg tctaggggca catgggtgtg tctgtggatg 17940
tggtgtctcc atgtggccgt ggtaggtggg ttgtgtactc tgtgtgtgca cgtggctgtg 18000
tatagctgtg tgtgcatgtg cagtatgtgc acgtcggtgc tgtatctaag tgcacatgtg 18060
gctactgatc aacagacatt tactgaacgt ctactgtgtt ccatgctcta ttctaaaccc 18120
tgggggcgct gggtgcagtg gctcatgcct gtaatcccag cactttggaa ggccgaggtg 18180
ggtggatcac ctgaggtcag gagtttgaga ctagcctggc caacatggtg aaacccgctc 18240
tctactaaaa atacaaatta gctgggcatg gtggtgggca cctgtaatct cagctacttg 18300
agaggctaag gcaggaatat cacttgaacc caggaggcag aggttgcagt gagccgagat 18360
tgtgccactg cactccagcc tgggcgccag agtaagacct tgtctcgaaa ataaaaatta 18420
aaaaataggc caggcgcggt ggctcatgca tgtaatccca gcactttggg aggctgaggc 18480
gggtgaatcg cttgaggcca ggagctcaag accaacctag ccaacatggt gaaactcctt 18540
ctctactaaa aatacaaaaa ttagccaggt atggtggcga gcgcctgtag tcccagctac 18600
gtgggaggct gaggcaggag aatcgcttga acccaggagg cagaggttgc ggtgagccga 18660
gattgcacca ctgcactcca gcctgggcaa cagagcgaga ccctgtctca aaaaaaaaaa 18720
aagaaagaaa gaaagaaaag agaagagggg agaggagggg aggggagggg aggggagggg 18780

-continued

```
aggggagggg aagggaaggg aagaaacgaa accctggggg ggatctagga gcagacaagt  18840
cccctgctct gtgttttcat aatctagtat ccaggaaggg gtaagcaccc tgcgtgtatc  18900
tggttgtaac taactactca caactgcact tgcctgtgtg aaaacgtgag cttgtgatga  18960
tgcgtgacgt caggtaggcg tccctgactc tccgtaaccc aactttgcct gtgccttggg  19020
gattcctcct tgcaggtagg aagtgagggg tacaggttcc agctctgggc tgagacatga  19080
ttcagggttc caccctgacc tggggctcct ggagtcttgg ggccctggag ggtcccgtcc  19140
actgcccaga ctgacccagg tcctcgatga agcctcatta tgaggactgg gggaaaagga  19200
cccagccact tcctggggag gtcggagacc ccagggtgag cgtcaaggta gcctcaaaga  19260
tgagacgtca cctcttgaag gcagccatga gccttgggtg gggacgtcac tagaggaagt  19320
tcaggcccta ttttcggagg aagcagttgg agaccccata ggaggaaggg cgatggggca  19380
gtagaaagtc gcggtgtccc cgccccctcc agcagctacg cgccccactc tcttggagac  19440
gctagatcag tccctccggg cctactaaag aaaccacgca gggctcagat ccgctccatc  19500
atcatcatca tcatcatcat catcatctcc aggtttattt ccagctcccc cgcaacccct  19560
ccggacctgg agccgcctcc gcccgcgctg tgcacgcgct gcgcgcgacc tcagggctgc  19620
acacgacagc agcgcgctcc ggtccagtcc atgcccgcgc actggcagtg acatgtggtc  19680
tcggcgcgca catcccacga gccacaggcg gagccacaag tgcagccggt gacggcgaag  19740
cctgcagccc ggaacacagg agcgtggact ctgagctggg aggctgaggg tgggagcggg  19800
aggggggtgg ggagcgcgga ggggggttgg gggggcgggg gtggggacgg ggacggctgg  19860
aggctccaac cactgaatgg gcactggagg cagggagtga gggtggacac cagtgtccag  19920
atggtgggcg gagaaggctg ggagtcagga ccaagatcct aggggagtag aggctggaca  19980
cggggaacgt ggcggggagg gggcattccc aggggacttg gaacagaaat gggcgcctgg  20040
acaacagtct cctgcactca cctcgggggc aagtagccag gtccccccctg gaggtgacgc  20100
tctggcactc caggccaatg ctgcttattg ccctaaatac tggggggcag gaggaaagga  20160
gacaggggga gctgtgagac caaacggtcc ctcccccatc ctcccctagc cctgttggtt  20220
tggagctagg tccctgtggg cataggagct cactggcctc caggaccctg tcttgagttg  20280
ggtgttttgg agtaagggaa ggtttggagt gagagcgggg attgggtttg gagccgtgga  20340
taaggtgggg acagtcggag gggttgggag tggagttggg gttgaattta tgatctggtt  20400
ggatttgagg atgagatttg gtgagcgctg gggctgggtt ggagtcaggt ctgtgccagg  20460
gatcagtgag gtctctgaga cccttgggga gcttgcccaa gtggggggtc ctcacttagg  20520
gagccggcga cctcctggat cctctcattg atggcttctt ccatggagca cagggtcttg  20580
ctagacacca acagccccag gacagggagg aggaggagac agagagcttt catcctgcag  20640
gcgctgaaag agggaaccaa gagacccaca gctggatcag ccctgccctg tggggaagat  20700
ccggcccatg gagggagtag gatctgcccc tggacctgga cccctgtccc cccatgtggg  20760
ggacagggat ggaggctcag ccttgacccc agcctccccg ctggtgccat ggcaagcgca  20820
ggagcagctg tcacttaccc tctcggtggg ctcagctaac caaatccggc acacgaattc  20880
ctgcaccgca gctctttctt tgaggcctct tggggtgggg cttcctggct tggctaataa  20940
gtccctgggc ccccaaccct ccggtcccac atccggggcc aagaggaagc ccctgagcag  21000
acagtaaggg ctggaggagg aagggagcct tcccacttcc aacagggcct ccgtcttcat  21060
gtccagagac tggtcaggag gtggtgcccc agggataatg ccaggggctg tggtctgagg  21120
aacaggtaga caagcagagt tttgcatgca agggtggctg atgcaaacat gacaaaatta  21180
```

-continued

```
atgcctcttg ctaggcatgg tgcggacaag cacttgtagt cccagctact aaggaggctg  21240
acgtgagaga attgcttgag cccgggagtt cgaagctaca gtgacttatg atcacagcac  21300
tgcactccag tctgggcaac agagcaagac cacttctcta aaatagtaat aataattatg  21360
tctctgggtg agaatgacat accacattca tacccaaatg cccatgagca atagaactgg  21420
taaataaaat catggtttat ggccggtggc tcacgcctgt aatcccagca ctttgggagg  21480
ccaaggcggg cggatcactt gaggtcagga gcttgagacc aacctggcca acatgatgaa  21540
accctgtctc cattagacat acaaaaatta actgggcgtg gtggcgtgtg cctgtaatcc  21600
cagctacttg ggaggctgag gtgggagaat cacttgaacc cgggatgtgg aggttgcagt  21660
gcactgagat cgtgcccctg cactccatcc tggatgacta gcttgggcac catagcaaga  21720
ctccatctca aaaagaagaa agaaaaatca tggtttattc catcaatggc atcacctgca  21780
acagaagttg gaaagccatt gctcatgggc caagtccagc tcatgtttct tcttggacca  21840
cccatgagct tggaatggtt attacatttt tatttgttct ttgtttccag tacaacgggc  21900
cttttgtggt aaaatacata taacatacaa cttaccatta taacttactt ttttcttttt  21960
tgagacggaa tcttgctctg tcgcccaggc tggagtgcag tggcgcgatc tcggctcact  22020
acaagctccg cctcctgggt tcacgccatt ctcctgcttc agcctcccaa gtagctggga  22080
ctacaggcgc ctgccaccac gcccagctaa tttttgtat ttttttttt ttagtagaga  22140
tggagtttca ccgtgttagc caggatggtc tcgatcccct gaccttgtga tctgcccgcc  22200
ttggcctccc aaagtgctgg gattacaggc gtgaaccacc gtgcccggcc ttttttttt  22260
tttttttgag acggggtctt gctatgttgc ccaagctagt gtcagactcc tggcttcaag  22320
taatcctccc accttggact ccccagtagc tgaagctaca ggtatgcacc atcttgttcc  22380
attttaacca ttgcttttgt ttgtttcttt gtttcagagt ctcactcagt tgctcaggct  22440
ggagtacagt ggctcaatct tggctcactg caacctccac ctcctgggtt caagcaattc  22500
tcctgcctca gcctcccgag tagctgggat tacaggcgtg caccaccatg cccggctaat  22560
tttttgtatt tttagtagag atggggtttc accatgttgg ccaggctggt ctcaaattcc  22620
tgacctcaag tgatccaccc gcctcagcct cccaaagtgc cgggattaca ggtgtgagcc  22680
accatgccca gcctatttta accatttttc agagcacaat tctgtggcaa taagcacatt  22740
catgttgtta tgtagccacc actgccgtcc atctccagaa ctttctcctc tttccaaact  22800
gaaactctgt ccccatgaaa cactcactcc ctatccctct ccccagcccc tggcaccctc  22860
catcttgctt tctgcctcta tggatctgat gactctaggg acctcctagg agtggaatca  22920
cacagtgttt gtccttttgt atctgcttat ttcactgagc ataatatccc caaggttcat  22980
ccctgctgta gcctgagtca gaactgtttt cctttccatg gctgtatcac attcccttgt  23040
gtggatgaac cacgttgtgt ttattccttc atccatcgat ggacacttgg gttgcttcca  23100
gcttttgttt tgtttttttg tttgtttgtt tgtttttgtt agttcacgtc ttttgtgggt  23160
tttctttctt ttttgagatg gagtctcact ctgttgccct ggctggagtg cagtggcacg  23220
atctcggctc actgcaagct ccgcctcccg ggttcactcc attctcctgc ctcagcctcc  23280
cgagtagctg ggactatagg cgcccgccac catgcccagc taattttttt gtatttttag  23340
tagagacggg gtttcaccat gttagccagg atggtctcga tctcctgacc ttgtgatccg  23400
cccgtctcgg cctcccaaag tgctgggatt acaggtgtaa gccactgcgc ctggccgtct  23460
tttgttaatt catacagtta tttgtcttct ggtttgttga agcagtaagt cagacaacat  23520
ttgccacaat aatgtctgtc aaagtggctt gccataaaca ctgcagcacc acattcatca  23580
```

-continued gaagggcaac ctcgacgaag gtgactaatt ttgccattct catccacctt ataatatttc 23640
aggacagcca gcttcacctt ctttctcttg tgcttattcg tcttgcaggt aagacttctt 23700
cttctggccg ggctcagtgg ctcaggcctg taatcccagc actttgggag gccgaggcag 23760
gtggatcacg aggtcaggag ttcaagacca gcctggccaa catggtgaaa tcctgtctct 23820
actaaaaata caaaaattag ctgggcgtgg tggcacgtgc ctgtaatccc agctactcgg 23880
gaggctgagg caggagaatt gcttgaactg ggacccggga ggcagaggtt gcagtgagcc 23940
gagattgcac cactgcactc cagcctgagc tacagagcga gactccatct caaaaaaaat 24000
aaaaaaaaga cttcttcctt tccttagcac caccacgaat tctcaataca agatgaagag 24060
gagactcctt ttgaatgttg tagtcagaca gagtacgccc atcttccagt gcttgtcttt 24120
gctgatcagg aggaattctt tctttaccct ggatcttggc ctttacattt tctaccatat 24180
ctgagggttc agcctcgagg gtggtggtct tccctgtaag ggttttcagg aaaatctaca 24240
ttttggtggc ggctccacca cagatggcgg atctaaaagg tttttgtttt ttgttttttt 24300
gagacagagt ttcgctcttg tcacccaggc tggagtgcaa gtggcacgat cttggctcac 24360
tgcaacctct gactcctggg tttaagtgat tatcctgcct cggcctccga gtagccagga 24420
ttacaggcat gtgccaccac cacacctggc taattttttt ttcttttgta tttttagtag 24480
agatggggtt ttgccatgtt ggccaggctg gtctcaaact cctgatctgg agtgatccgc 24540
ctgcctcggc ctcccaaagt cctgggatta caggtgtgag ccactgtgcc tggcctgctt 24600
ctgccttttg gctattgtga ataatgctgc tctgaacata gatgtgcaaa tatctgtttg 24660
cagctcctgc tttcaattct tctgggcgta tgtccaggag tagtgctgcc tgatcatatg 24720
gtaattctat gtttaacttt ttgaggcact gccaattttc acatttttaa accataggga 24780
aaaaaaagtt gttttttttt taaaaaagac acagtctggc tctgttttcc acgctggagt 24840
gcaatggtgc aatcatagct cactgcagcc tcaaactcct gggctcaagc aatccccccc 24900
tcatcagcct cttgagtagg tgggactacg gcatgtgtca ccacacctaa ctaatttttt 24960
taattttttt gtagaggtgg ggtctcactc tattgcccag gctggtctca aactcctggc 25020
ctcaaaagat cctgccacct tagcttccca aagcactgag attacaggca tgagccactg 25080
tgcctagcca aaaaatattt gtaatgttta gtgaaaatag aaatcatata aaattcaaat 25140
tcatataatt ttcataaaaa gtccataaag aaaattttct taaaacattg tcagctgggt 25200
gcggtggctc atgcctgtaa tcacagcact ttgggaggct aaggcgggtg gatcacctga 25260
ggtcaggagt tcaagaccag cctggccaat gtggtgaaac cccatcacta cttacaatac 25320
aaaattagcc gggtgtggtg gcacgcgact gtaatcccag ctacttgaga ggccgaggca 25380
ggagaattgc ttgaacccgg gaggtggagg ttgcagtgag tcaagatggt gcccttgcac 25440
tccagcctgg gcaacaagag cgaaactctg tctcaaaaaa aaaaaaaatt gccaagctca 25500
gtggcaggca cctgtcatcc tagctacttg agagaccaaa gcaggaggat tgtttgagcc 25560
caggagtttg agggcagcct gagcaacata gtgagatcct gtccctacaa acacacacac 25620
acagtttgct accccctttt ttttgagagg gagactcgct cttgtcaccc aggctggagt 25680
gcagtggcac gaccttggct caccgcaacc tctgcctccc gggttaaagc gattctcctg 25740
cctcagcctc ccgagtagct gggattatag gcaggtgcgc caccatgtcc ggctaatttt 25800
tgtattttta gtagagatgg gatttcgcca tgttagccag gctggcttcg atctcctgat 25860
ctcaagtgat ccgcccgcct tggcctccca gagtgctgag actataggca tgagccactg 25920
cacctggccc catttttaa tatatcatca gtgactgcta tcacatgtcc atggcagagc 25980

-continued tcagcagctg tagagtggtt ggacagtagg gcccccaaag ctgagaatgt ttactatctg 26040
actcgttaca gaaaacattt ttttgtaccc ctggtatgtg gtgatgagtg agaatgagac 26100
aactgtccat ggattacagc tacacccaac catgtggctg attctcacga acatatgtta 26160
gcatagaagc cagaccccaa aaagaacata ccatacaaat ccatttatta aaaaaaaagg 26220
gggccgggcg cggtggctcc tgcctgtaat cccagcactt tgggaggcca aggcaggcgg 26280
atcacaaggt caggagatca agaccatcct ggctaacacg gtgaaacccc atctctacta 26340
aaaatccaaa aaaattagcc gggcgtggtg gcaggcacct gcagtcccag ctcctcggga 26400
ggctgaggca ggagaacggt gtgaacccgg gaggcggagc ttgcagtgag ccgagatggc 26460
gccactgcac tccagcctgg gcgacagagc aagactccgt ctcaaaaaaa aaaaaaaata 26520
cctaaaaata caaaaattag ccaggtgtag cggcaggtgc ctgtaatccc agctactcgg 26580
gatgctgagg gaggagaatc gcttgaacca agaggtggag gttgcagtga gctgaaatca 26640
tgctactgca ctccagcctg ggcaacagag agagactccg tctcacaata atgataataa 26700
taataaatga aatacaaaca aaactaattt atgctgtcgg aaatgacgat ggaagagtcc 26760
tggggaatca gagatagtgg tgataaaagc ataccaggaa ggcccctagt gaggggggaa 26820
ttttgtaaaa gttttcagct gtaactctca tttgcacaat tttctctatg tatttatatt 26880
tcaatcaaca tgatgcatgt gtattaaagc cctgtgtaaa tgcaacggtg cacacaggtt 26940
caaagcgcag gcaatattta ttgagcaact attatgttcc atatgctgtg ttaaacacca 27000
tgcatacact aagaagcaga gggatgctgc ccttgcccgg gacgagttgg cccttgtcag 27060
tcagggaaag gcagacacca acagaacagc aataaaaagg ccgggcaatg ggccaggcgc 27120
ggtggctcat gcttgtaatc ccagcctttt gggaggccga ggcgggtgga tcacctgagg 27180
tcgggagttc gagaccagcg tgaccaacat ggagaaaccc cttttctact aaaaacacaa 27240
aattagccag gcgtggtggc acaccaggtg ggtagctgta atcctagtta ctcgggaggc 27300
tgaggcagga gaattgcttg aacccgggag gcggaggttg tggtgagcca aggttgtgcc 27360
attgctttcc agcctgggca acaaaaagca aaactccatc tcaaaaaaaa aaaaaaaagt 27420
ccgggcgcca tggctcacac ctgtaatccc agtgctttag gagaccgagg tgggtggatc 27480
acttgagccc aggagttcaa gaccagcctg gccaacacag tgagaccctc cctctgtaca 27540
aaacgtaaga aaacattagg cagggatggt ggtggcttcc tgtagtccca gctactcagg 27600
aggctgagac agaagtaccg cttgagtcca ggagttggag actgcagtga gctatgatcg 27660
caccactgca ctccagcctg gacaacagag caagacccca tctctaaaaa aaagaaaaca 27720
aaaaaacaac aacaaaaaac accaatagaa tgctcaatca gccatcagcc tcaaggaccc 27780
ttccatctcc caaggagagg aacccttttc cgtgagaacc tctgacctaa aaatcaaccc 27840
cacatggggg aatccagaaa gtattttggg gggaggaaaa gatgtttgaa gggagggtgg 27900
aggatgcaga agggttaacc aggagaggca gttagggagg gccttctggg tggagggaga 27960
ggactgcatg ttccaaggac ctgaggcaga atggagtgtg tgtatttaga ggaactgaaa 28020
gcaaatttgt gggacagggg atctagaggg gaaaagtgaa ttccacaggc tccctgtctc 28080
ttctggtcct agcaggaact ttcaagtccg tttttgtcca gatatttccc catgctcaag 28140
tcccagctca tcctgcctcc ttgaagacat gacttctgtc tcttcttgag ctactctttg 28200
acacaccctg gacaaagggt agcttgaaaa gagacagaaa ccatgttatt gccaggtgca 28260
gtggctcacg cctgtcatcc ttgtgctttg ggaggctgag gcaggaggat cgcttgaggc 28320
caggagcttg agaccagcct ggacaacata acaagacccc atctctacaa agataaaagg 28380
gaaaaagccg ggcgcagtgg ttcacgcctg taatcccagc actttgggag gccaaggtgg 28440
gcagatcacc tgaggtcagg agttcgagac cagcctggcc aacatggcga aaccccgtct 28500
ctactaaaaa tacaaaaatt agatgggcgt ggtggcgggc acctgtaatc ccagctactc 28560
gggaggctga ggcaggaaaa tcacttgaac ccaggaggtg gaggttgcag tgagctgaga 28620
ttgcaccact gcactccagc ctgggcgaca gagtgagcct tggtctcaat caatcaatca 28680
atcaatcaat ggaaaaaaat tagctgggtg tggtggtcca tgctggtagt cccagctact 28740
gaggaggctg gggtgtgagg atcacttgag cccaggaagg ctgagactgc aatgagctat 28800
gatggcatca ctgcactcca gcctggacaa caaagcaaga tcccgtctca aaaaaaaaga 28860
agaaaaagaa aaatcatttt ttgagagctc tgattttcaa accctttgtt ctcagaactc 28920
ttcgggtaaa accttttgaa cgacacaaaa ggagtgggca gctgtgatga cagattgagg 28980
agaaagcagg gtaggcatgg aacctctagg gttccctagg gacccagttt gaaaactctt 29040
ggttcagtag caggaaaagg caatatgccc cttaattctc ttctaaaaca taaaatcctt 29100
taacttcctc tgatttctac cagtaaaact gagctctact gacctcaatt ttgtaccaaa 29160
tgctatctaa taaaatccca gaaacagtga tttttgaaaa atccattttg ttgatgtgta 29220
atttacatac agtagaatgt gcctatctta tgtgtttggt ttcatgcatt gtttttcttt 29280
ttcaactttt taaatttttt tttttttttg agacagggtc tcactctgtt gcccaggttg 29340
gcgtgcagtg gcacaatctc ggctcactgc aaccttcgcc tctcgggttc aagcaattct 29400
cctgcctcag cctcctgagt aggtgggacc acaggcacgc gccactacac ccagctaatt 29460
tttgtatttt tagtagagac agggtttctc catgttggcc aggttggtct cgaactcttg 29520
acctcaagtg atccacccac ttcggcctcc caaagtgctg ggaccacagg cacacaccac 29580
cacgcccaac taatttttgt atttttcata gagatggggt ttcaccatgt tgcccaggct 29640
ggtctcaaac tcctggcctc aagtgatctg cctgccttgg cctcccaaag tgctggaatt 29700
acaggcataa gccaccatgg ccagccctct ttatcaactt ttatttattt tttcattttt 29760
ttgagacgga gtctcgctct gttgcccaaa ctggagtgca gcggtgcgac ctcagctcac 29820
tgcaacctcc gcctcccggg ttcaagcgat tctcctgcat cagcctccca agtagctggg 29880
attacaggtg cccgccacca cgcccatcta atttttgtat ttttagtgga gacggggttt 29940
caccatgttg cccaggctgg tctcgaactc ctggcctcaa agcgacctgc ccgccttggc 30000
ctcccaaagt gctgggatta cagttgtgag ccgccgcgcc cgggaccctc tttatcaact 30060
tttattttag attcagggga tacctgtgcc agtctcctac ctgagtatat tgcatgatgc 30120
tgaggtttgg ggtatgagcg actctgtcac ccagatggtg agcacagcac tcaacagtta 30180
gattttcaac cctcatgccc cttttcctca cccctccctg gcaatcccca ctgttcatta 30240
ttgccacctt tatgtccatg agtacctgaa gtttagatcc cacttataag tgagaacagg 30300
cagtctttgg tctgctgtta ctgagtttga tgcattttga caaatgtgtc tacctgcctg 30360
ctgcacgttt tggttttccc aagaattatt ttctaaaaat cagtttttat taaggtggca 30420
tttatataca ctaaaattct gcacacgatc ttgtaaccat caccaccaaa tacgtattta 30480
tttatttatt attatttttt agagatggcg tctcactctg tctcgatctc ccacgccggg 30540
gtgcagtggt gccatcagag ctcactgcat cctccaactc ctgggctcaa gcgatcctcc 30600
tgcctcagcc tcctgagtag ctaggactac aggcacccac caccacccac agttaattga 30660
aaaaattgat tcttctttgt agagacaggg tctcatatgt tgccaggatc cttggtcttt 30720
gacctcccaa agtgcagaga ttacaggcat gcaccactaa tgccgggcca aatacttgta 30780
atttaaatta tcgctgggct gggcacggtg gctcacgcct gtaacccagc actttgggag 30840
gccgaggggg gaagttcacc tgaggtcagg agttccagac cagcctggcc aacatgctga 30900
aaccctgtct caactaaaaa tacaaaaatc agccggacat tgtggcagac gcctgtaatc 30960
ccagctaatc gggaggctaa gacaggagaa tcgcttgaac ccgggaggca gaggttgcag 31020
tgagccgaga tcgcaccatt gtgctccaac ctgggcaaca agagcgaaac tccatctcaa 31080
aaaataataa taaaataaat tatagttgga aaaaaggggt ttcctaaaga cccaagggaa 31140
atggcctctt tgttcctgaa gccacagaga ggatttttct gctccccaca actagttttc 31200
cttgtgaaaa ttcataattg ctaccagctt gttctcctct ctgtcactat acatctgtcc 31260
ttgaagcctt atttgaacaa agagttctgg tatcactcgg atgcctagaa actgttgccg 31320
ttctgtgaaa ccgaccacca gaggaaaccc atgcttctca ttggctgcct tactaagatg 31380
gtgacttgtt gccctggtga caagttgcaa tgacaggtgg ctctgccaaa tcagaacaca 31440
gtgatacttg cttcccctcc cgggtgaagg atggaaaata aaagtaaaag ccttggcggc 31500
tgtcaggctt ctttaccaaa gagctggaga gcactccttg gccccattta tgcaaacact 31560
tcccatctac agatgatcca gcttcggagt gggagtctaa gcagctgcca ggaccaccgc 31620
ttggcagagg acaggctggg ggctctggca tgacctgctg gggccaggct gtgacttgga 31680
gcaagaggta gcaagaacct cgaggcagtg aacatcaaaa gagagatttc cggggctaaa 31740
caccctaggt ttttccttcc tcctgaaccc taaccctaac cctctcggct cactgcaacc 31800
tccacctccc gagtgcaagc aattctcatg cctcagcctc ccgagtagct gggatcacag 31860
gcgtgcgcca ccacgcccgg ctaactttgt atttttatta gagacggggg tttctccacg 31920
ttggtcaggc tggtgtcaaa ctctcgaact caggtgatct gcccgccttg gcctccaaaa 31980
gtgctgggat tacaggcgtg cgccaccgtg cccagcttat ttttgtattt ttagtagagg 32040
tggggtttca ccctgttggc caggctggtc ttgaactcct gaactcaagt gatctgcctg 32100
cctcagcctg ccaaaatgct ggggttacag gcgccaggcc aagtatctta ttttaaaagg 32160
ttacaaagaa tatagatgtg gataaaataa aagtttcttt gcattaccac tttcctgcaa 32220
gaaatgaggg ggaggggctt atgaaacaac tcacaccccc ccaattgagg aactgtagat 32280
gaaagggaag gtgctgacag gcccgtctgg ccacggtttc ctggaataaa actgagccac 32340
acacctccac aaatccccag cctccggcaa gtaccccaga agtactcaca ctccaccacc 32400
ttctgtgatc gcaacagccc tacgcaacat tacagagggc aaaacccacg ctggggaagg 32460
cggggctact gtcaaaaggt caccagggcc aggcacagtg gctcacgcct ataatcccag 32520
ctccttggga gaccaaggca ggaggatccg ttgagctcaa gagtttgagt tcagcctggg 32580
caacacagga aaacccccgt ctttacaaaa actttttaaa aattagctgg gtgtggtggc 32640
atgcccgtgt aatcccagcc actacttagg aggccgaagg gggaggatct attgcttcag 32700
cccgggagtt tgtggctgca gtgagctatg attgcaccac tgcactccag cctaagtgac 32760
agacagagac tcttaaaaaa aaaaaaaaaa gggcagggca cggtggctta tgtctgtaat 32820
cctagcactt tgggaggccg aggcgggcag atcatctggc gtcaggagtt cgaggccaac 32880
ctggccaata tggtgaaacc ctgtctctac caaaagtaca aaacttagct gggtgtgatg 32940
gtgggcacct gtaatcccag ctactcggga ggctgaggtg ggagaatcgc ttgaatctgg 33000
gaggtggagt ttgcagtgag ccaagattgc gccactgcac tccagcctgg gtgacagaat 33060
gagactctgt ctcaaaaaaa aaaaaaaaaa gtggggcacc tatattccca gcactttggg 33120
aagctgaggc aggaggatgg cttgaggcca aaaattcaaa acccggcctg ggcaacatag 33180

```
caagacccca tctctatgaa aaaaaaaaaa aaaaagtcac caggccagct agcctagatt  33240
tcagagccag aatttgtctg atgccattgt ctttactttt tctttttctt tttttttttt  33300
ttgagacaga gtctcactct gtcacccaag ctgcagggca gtgggacaat ctcagctcac  33360
tgcaacctct gcctcccagg ctcaagcgat tctcctgcct cagcctcctg agtagctggg  33420
attacagaca tccaccacca tttccagcta atttttgtat ttttagtaga ggtgaggttt  33480
caccttttg gtcaggctgg tctccaactc ccaagctcag gtgatctgcc cacctcagcc  33540
tcccaaagtg ctgggattac agttgcgagc caccacgcct ggactgctct tcattctttt  33600
ttcagaactt tcccagctgc caacagagac agaaactgaa tcatctcaga agtgaatgaa  33660
ggaggctgag ggcgggtgga ctgcttgatt aggagttcga gatttgccta ggcaacatgg  33720
aaaaagcctg tctctgctaa aaatacaaaa attagccggg cgtggtggca catgcctgta  33780
atgccagctg cttgggaggc tgaggcagga gaatcacttg aacccgggag gcagaggctg  33840
cagcgagccg agatcgcgcc actgcactcc agcctaggta acagggcgag actccgcctc  33900
aaaaaaaaaa gaagggaatg aaggacaccc aaaatggagc ctctgtctgc cagggctttg  33960
ctatcctggc ctgcctatcc cagccctgga cacctcatct ctgatcccac cagagcggaa  34020
ccttcccatt cgcagggcca tttccttacc cagaaacctt ttcacaatgt tcttggcagc  34080
agctgttggt caactgtgtt ttaaggtttt tgagcaactt tacagaaaat aaaagggaag  34140
ctaccctcaa tgtctgggtc tccccctggg tggcctctct ttgtcacctt actcatttcc  34200
acgagatttc cttgcttcgt tgagttacat cacctccttt tcctgtctgg gtccaggacg  34260
cctcctctgc aggtctccag cactgattcc tttgtccccg atttctctgc tagggtcgct  34320
ggcttcacca tcccaccacc actgctgctg gcccagcccg cagctttaat ttctctggac  34380
cctcacgttt ttgttatttg tgtttttttt ggagatgagg tcttgctctg tcacccaggc  34440
tggagtgcag tggtgcaatc acagctcact gtagcctcca cctcccagac tcaagtgatc  34500
ttcctgcctc agcctcccaa gtagctgggt gtgtgccacc aggtgcagct acattttttg  34560
tagaggcagg ggtcttgcta tattgcccag gctggtctca aactcccagc tttagatgat  34620
cctttcacct cggcctccca gagtgctggg attaccagca tgagccactg cacccgtcct  34680
ctcatgtatt ttttattaat cgatttatct atttacttat tttgagacag agtcttgctg  34740
taccacccag gctggagtgc agtggcatga tctcggccca ctgcaacctc cactccctgg  34800
gttcaagtga ttctcctgcc tcagcctccc gagtagctgg gattacaggt gcccgccacc  34860
atgcctggct aatttttgta tttttagtag tgacgaggtt tcaccgtgtt ggccaggctg  34920
gtctcgaatt cctgacctca ggtgatccac ccaactcggc ctcccaaagt gctgggatta  34980
caggcgtgag ccaccgcact cggcctccct catgtatttt taagcggaac aggttcaaga  35040
tcacaaatgt tttcctctca ctctttcaat gagtttctat tctagaatct cctgcacgcc  35100
acaggaagga gaactctcac cctgtaatgc acataaatac atgagatcac cattgttctc  35160
acccagtaat cagaatcgtt agtgataatt agtaataaat ttatttttac tatatctaat  35220
aaattagata gtaattacta tggcagccaa tcgttcctgg gtgctcccta gatgcttcca  35280
agggagccac acgtgaccct cagggctgtg cccattccag gctcttctgc tgagctcatg  35340
taaccgcttg cctcaaggca ttccacaaat aatacataag tcaatgtatc acgttgtcac  35400
tttctgtaca aaccagctag ttccggaggg aagcagaaag ccttttcag aagaaccaca  35460
gctaattcca gtagcaggaa tgataaagtt ggacataatc ctcaagagag taatgaatca  35520
aaaatggatg gcgggccagg cacggtggct gatgcctgta atcccagcac tttaggagga  35580
```

-continued tgaggcaggt gaatcatttg aggtcaggag ttcaagacca gcttggccac catggtgaga 35640
ccccgtctct actaaaaata caaaaattag cctggcatgg tggctcatgc ttgtagtccc 35700
agcttcttgg gaggctgagg caggagaatt gattgaaccc tggaggtgga gattgcagtg 35760
agccaagatt gcatcactgc actccagcct gggcaacaag agcgaaactc tatctcaaaa 35820
acaaacaaac aaacaataac aacaacaaaa ttgatggctg ctaatgactt tttttctttt 35880
ctttcctttt ttatttttat tttttatgag acagggtctc actctatcgc ccaaactgga 35940
gtgcagtgcc gagatcataa ctcagtgcag cctcaacctc ttggactcaa gtgatcttcc 36000
cacctcagcc tcccatgtag ctgggactac aagcaattgc tgccacatct ggctaattat 36060
tttattttgt tgtattttat ttatttattt tttgagacag agtcttactc tgtcacccag 36120
gctggagtgc aatggcatga tctcagctca ctgcaacctc cgcctcctgg attcaagtta 36180
ttctcctacc tcagcttcct gagtagctgg gataacaggt gtgcaccacc acgcctggtt 36240
aatttttggt tttttggtag agacggggtt tcatcatgtt ggccaggctg gtcttgaact 36300
cctgacctca agtgatccgc ccatctcagc ctcccaaagt gctgggatta caggtatgag 36360
ccaccgtgcc cggtctttat tttatttttta gtagagacag ggttttgcta tgttgcccag 36420
gctggtctca aactcctggg cctaagtgat cctcctgcct tggcctccca aagtgctggg 36480
aactacaggc gtgagccact gggcccagct cctgttaaca tctttatgtg gagagttact 36540
ggggaccagg gacattcccc aaacccaccc atcaatcgta gtgacatgac gttatggacc 36600
ccctgatgtg atgtaccagg aagtacccgg ccctaccagc atgatattat tctggctgca 36660
actgaccctt attccaatag agcatgtggt tctaagccat ttatagggta aacattgggg 36720
cagggatggg gagagaggaa gcaacctgcc aaatccagaa tgaggatcat tcctcggtac 36780
cagaagagaa ccagaaagaa agcaccctaa gtggggatac cacaaggaag taaagcaggg 36840
gcctctccca gctggggaag ggaaggagga aggagtacaa tagcttgcaa ggcacagcat 36900
tgcggatgat gggaatagca ggtgcaaagg ttctggggca gggacagtgt ggtgtgtttg 36960
aagaacagca gccaggttca ccatgagatg ggaaatggac ttgggggaag ggatctcaaa 37020
ggataatttt tttttttttt ttgagacagg gtttcgctct tgttgcccag gctggagtgc 37080
agtggcatga tggctcactg caacctctgc cttccggttt caagcgattc tcctgcctca 37140
gcctcccgag tagctgggat tacaggcgcc caccaccacg cccggctaat ttttgtattt 37200
ttagtagaga cagggtttca ccatgttggc tagactggtc ttgaactcct gacctcgtga 37260
tccgcccgcc tcggcctccc aaagtgctgg gattacagac gtgagccacc gcgcccggcc 37320
ccccaacttt ttttttgttt ttaacacaac ttctcgcttt ctcacccagg ctggagggca 37380
gaggcacaat catagctcac tgcagcctcg aactcctagg ctccagcgat cctcacagga 37440
gggttttgag gatctgcata aagcgtgcag agggagcttg acttcgtgct cgttaggacc 37500
cgatattgtc agctgccgcc gcccacaggg acacataaat atttgtagac tcaatatttg 37560
cctttagtgt gaagacattg catcacctgg gtataagtaa ggagcagagg cagaggcggt 37620
ttaagcaaca gacttttgtc tccgctgaga accacggaat aacccctgac ctacttcccc 37680
gtcgtgtcta attcgggtca cctcatctcc agttacagac gcggaagatc aaagaaaccg 37740
ggaaattgcg ccgcagcgcc ccctggcgtt cgcagcgcgt gcctacacaa gccactcccg 37800
gcgcaaaact gcggcttccc aggaaattga gtttaaatgt ttttttttct tttttcttaa 37860
tctagaaaag atcatttatt gtatcaagta actacccagt taggcgtgaa tacattttaa 37920
aatttttatt aaaacgagta ttggccgggc gcggtggctc actcctgtaa tcccagcact 37980
ttgggaggcc aaggcaggtg gatcacggcg tcaggagttc gagaccatcc cggccaacat 38040
ggtgaaaccc cgtctctact aaaaatacaa aaattagctg ggcgtggtgg cacgcacctg 38100
tagtcccagc tactcgggag gctgagacag aagaatcggt tgaaccgggg aggcggaggt 38160
tgcagtgagc tgagatcatg ccactgcact ccagcctggg cgacggagcg agactccatc 38220
tccaaaaaat aaataaataa ataaatataa tataatataa aataaaataa aaagagtatt 38280
gtagagattg gctgggcaca gtggctcaca cctctaattc ctgcattttg ggaggctgag 38340
gtgggaggtc ttcagcccag gagttagaga ccagcctggc caacatggca aaaccccatc 38400
tctactaaaa gtacaaaaat tcgctgggca tggtgtcgca cgtctgtgat cccagctttt 38460
tgggaggctg aggcaggaga atcgcttgaa cccaggaggc agaggttaca gtgaatcgag 38520
atcgcaccac tgcactccag cctgggcaac agagtgagac cttgtctcaa aaatacatat 38580
atttagg 38587

<210> SEQ ID NO 4
<211> LENGTH: 30943
<212> TYPE: DNA
<213> ORGANISM: Homo sapiens

<400> SEQUENCE: 4
gggcgtggtg gcacatgcct gtaatgccag ctgcttggga ggctgaggca ggagaatcac 60
ttgaacccgg gaggcagagg ctgcagcgag ccgagatcgc gccactgcac tccagcctag 120
gtaacagggc gagactccgc ctcaaaaaaa aaagaaggga atgaaggaca cccaaaatgg 180
agcctctgtc tgccagggct ttgctatcct ggcctgccta tcccagccct ggacacctca 240
tctctgatcc caccagagcg gaaccttccc attcgcaggg ccatttcctt acccagaaac 300
cttttcacaa tgttcttggc agcagctgtt ggtcaactgt gttttaaggt ttttgagcaa 360
ctttacagaa aataaaaggg aagctaccct caatgtctgg gtctccccct gggtggcctc 420
tctttgtcac cttactcatt tccacgagat ttccttgctt cgttgagtta catcacctcc 480
ttttcctgtc tgggtccagg acgcctcctc tgcaggtctc cagcactgat tcctttgtcc 540
ccgatttctc tgctagggtc gctggcttca ccatccccacc accactgctg ctggcccagc 600
ccgcagcttt aatttctctg gaccctcacg tttttgttat ttgtgttttt tttggagatg 660
aggtcttgct ctgtcaccca ggctggagtg cagtggtgca atcacagctc actgtagcct 720
ccacctccca gactcaagtg atcttcctgc ctcagcctcc caagtagctg ggtgtgtgcc 780
accaggtgca gctacatttt ttgtagaggc aggggtcttg ctatattgcc caggctggtc 840
tcaaactccc agctttagat gatcctttca cctcggcctc ccagagtgct gggattacca 900
gcatgagcca ctgcacccgt cctctcatgt atttttttatt aatcgattta tctatttact 960
tattttgaga cagagtcttg ctgtaccacc caggctggag tgcagtggca tgatctcggc 1020
ccactgcaac ctccactccc tgggttcaag tgattctcct gcctcagcct cccgagtagc 1080
tgggattaca ggtgcccgcc accatgcctg gctaattttt gtatttttag tagtgacgag 1140
gtttcaccgt gttggccagg ctggtctcga attcctgacc tcaggtgatc cacccaactc 1200
ggcctcccaa agtgctggga ttacaggcgt gagccaccgc actcggcctc cctcatgtat 1260
ttttaagcgg aacaggttca agatcacaaa tgttttcctc tcactctttc aatgagtttc 1320
tattctagaa tctcctgcac gccacaggaa ggagaactct caccctgtaa tgcacataaa 1380
tacatgagat caccattgtt ctcacccagt aatcagaatc gttagtgata attagtaata 1440
aatttatttt tactatatct aataaattag atagtaatta ctatggcagc caatcgttcc 1500

-continued

```
tgggtgctcc ctagatgctt ccaagggagc cacacgtgac cctcagggct gtgcccattc   1560
caggctcttc tgctgagctc atgtaaccgc ttgcctcaag gcattccaca aataatacat   1620
aagtcaatgt atcacgttgt cactttctgt acaaaccagc tagttccgga gggaagcaga   1680
aagccttttt cagaagaacc acagctaatt ccagtagcag gaatgataaa gttggacata   1740
atcctcaaga gagtaatgaa tcaaaaatgg atggcgggcc aggcacggtg gctgatgcct   1800
gtaatcccag cactttagga ggatgaggca ggtgaatcat ttgaggtcag gagttcaaga   1860
ccagcttggc caccatggtg agaccccgtc tctactaaaa atacaaaaat tagcctggca   1920
tggtggctca tgcttgtagt cccagcttct tgggaggctg aggcaggaga attgattgaa   1980
ccctggaggt ggagattgca gtgagccaag attgcatcac tgcactccag cctgggcaac   2040
aagagcgaaa ctctatctca aaaacaaaca aacaaacaat aacaacaaca aaattgatgg   2100
ctgctaatga ctttttttct tttctttcct tttttatttt tattttttat gagacagggt   2160
ctcactctat cgcccaaact ggagtgcagt gccgagatca taactcagtg cagcctcaac   2220
ctcttggact caagtgatct tcccacctca gcctcccatg tagctgggac tacaagcaat   2280
tgctgccaca tctggctaat tattttattt tgttgtattt tatttattta tttttgaga    2340
cagagtctta ctctgtcacc caggctggag tgcaatggca tgatctcagc tcactgcaac   2400
ctccgcctcc tggattcaag ttattctcct acctcagctt cctgagtagc tgggataaca   2460
ggtgtgcacc accacgcctg gttaattttt ggttttttgg tagagacggg gtttcatcat   2520
gttggccagg ctggtcttga actcctgacc tcaagtgatc cgcccatctc agcctcccaa   2580
agtgctggga ttacaggtat gagccaccgt gcccggtctt tattttattt ttagtagaga   2640
cagggttttg ctatgttgcc caggctggtc tcaaactcct gggcctaagt gatcctcctg   2700
ccttggcctc ccaaagtgct gggaactaca ggcgtgagcc actgggccca gctcctgtta   2760
acatctttat gtggagagtt actggggacc agggacattc cccaaaccca cccatcaatc   2820
gtagtgacat gacgttatgg accccctgat gtgatgtacc aggaagtacc cggccctacc   2880
agcatgatat tattctggct gcaactgacc cttattccaa tagagcatgt ggttctaagc   2940
catttatagg gtaaacattg gggcagggat ggggagagag gaagcaacct gccaaatcca   3000
gaatgaggat cattcctcgg taccagaaga gaaccagaaa gaaagcaccc taagtgggga   3060
taccacaagg aagtaaagca ggggcctctc ccagctgggg aagggaagga ggaaggagta   3120
caatagcttg caaggcacag cattgcggat gatgggaata gcaggtgcaa aggttctggg   3180
gcagggacag tgtggtgtgt ttgaagaaca gcagccaggt tcaccatgag atgggaaatg   3240
gacttggggg aagggatctc aaaggataat tttttttttt tttttgagac agggtttcgc   3300
tcttgttgcc caggctggag tgcagtggca tgatggctca ctgcaacctc tgccttccgg   3360
tttcaagcga ttctcctgcc tcagcctccc gagtagctgg gattacaggc gcccaccacc   3420
acgcccggct aatttttgta tttttagtag agacagggtt tcaccatgtt ggctagactg   3480
gtcttgaact cctgacctcg tgatccgccc gcctcggcct cccaaagtgc tgggattaca   3540
gacgtgagcc accgcgcccg gccccccaac tttttttttg tttttaacac aacttctcgc   3600
tttctcaccc aggctggagg gcagaggcac aatcatagct cactgcagcc tcgaactcct   3660
aggctccagc gatcctcaca ggagggtttt gaggatctgc ataaagcgtg cagagggagc   3720
ttgacttcgt gctcgttagg acccgatatt gtcagctgcc gccgcccaca gggacacata   3780
aatatttgta gactcaatat ttgcctttag tgtgaagaca ttgcatcacc tgggtataag   3840
taaggagcag aggcagaggc ggtttaagca acagactttt gtctccgctg agaaccacgg   3900
```

-continued

```
aataacccct gacctacttc cccgtcgtgt ctaattcggg tcacctcatc tccagttaca   3960
gacgcggaag atcaaagaaa ccgggaaatt gcgccgcagc gccccctggc gttcgcagcg   4020
cgtgcctaca caagccactc ccggcgcaaa actgcggctt cccaggaaat tgagtttaaa   4080
tgtttttttt tctttttttct taatctagaa aagatcattt attgtatcaa gtaactaccc   4140
agttaggcgt gaatacattt taaaattttt attaaaacga gtattggccg ggcgcggtgg   4200
ctcactcctg taatcccagc actttgggag gccaaggcag gtggatcacg gcgtcaggag   4260
ttcgagacca tcccggccaa catggtgaaa ccccgtctct actaaaaata caaaaattag   4320
ctgggcgtgg tggcacgcac ctgtagtccc agctactcgg gaggctgaga cagaagaatc   4380
ggttgaaccg gggaggcgga ggttgcagtg agctgagatc atgccactgc actccagcct   4440
gggcgacgga gcgagactcc atctccaaaa aataaataaa taaataaata taatataata   4500
taaaataaaa taaaaagagt attgtagaga ttggctgggc acagtggctc acacctctaa   4560
ttcctgcatt ttgggaggct gaggtgggag gtcttcagcc caggagttag agaccagcct   4620
ggccaacatg gcaaaacccc atctctacta aaagtacaaa aattcgctgg gcatggtgtc   4680
gcacgtctgt gatcccagct ttttgggagg ctgaggcagg agaatcgctt gaacccagga   4740
ggcagaggtt acagtgaatc gagatcgcac cactgcactc cagcctgggc aacagagtga   4800
gaccttgtct caaaaataca tatatttagg aatttgctat gttgcccagg ctggcctcaa   4860
actcctggcc tcaagcaatc ctcccacctc gccctcccaa agtgctggga ttgcaggcgt   4920
gagccactgt gcccgacctt gagcttaagt tttaaacatt aaaaccacct ccctcccact   4980
ccctgcacct cccgtaagtt aaaacgcgtc cctgctgagg ccctgcaaag gcatatccag   5040
ggcaggcgga ccccaggggt ccacagccga cccactttct tccccacacc tcatcccctt   5100
cacaactctc ctcatccatc tccctgccct ggtgggagat tccgataaat cctaattgtg   5160
gaactgctga atcagagggg gctgcatttt ccttagcccc cacctgcaaa ttgtgtgtgc   5220
agtttttctg ggatgagtgt ccttagattt ccctgaattc tcaaaaggat ctgtgacctc   5280
aaaatcagga gagaggccgg gcacggtggc tcacgcctgt catcccagta ctttgggagg   5340
ccgaggtggg cagatcgctt gagcccagga gaccagcctg ggcaacatag ccagacccag   5400
tctctacaaa aaattaaaag attaactggg cttggtgatg tgcactcatg gtcccagcta   5460
ctcaggaggc tgaggtggga ggatcgcttg agcacaggcg gtaagagagg ctctacctct   5520
gaagaggatg cttccccacc ctctgccccc tccccaggca cccactccag cagtgagaat   5580
ttcactgcca acatgagaca tgggtcccta cctgtcccaa ctcagaccct gtctatgatg   5640
tcctatggcc tcagcaggga ccaaaaccct caccatggcc tcaccagaac ctccacgtgg   5700
ttctcagatt gggttgcagg tcagtaccct cccctccagc tcctcagggg cctcctgcat   5760
tctctggcct tggcttctgc tctgccctcc cctcccttcc cttcgccccc ttcattttca   5820
ttctctatgc aaatgctgcc tcctctagga agccttccct gattgccccc agtctgggtg   5880
gattagatgt gatatgggct cccacagccc cttttgcctc agattactca tgtggctggc   5940
tgtatatctg tgccccagag aggtttcttt tcctttttct tttttttttt tttttttgag   6000
atagggtgtc accttgccac ccaggctgga gtgcagtggc atgatcatag ctcattgcag   6060
tctcaacctc ccgggctcaa gcaatccttc cacctgaaag tcctgagcag ctgggactac   6120
aggcgtgtgc catcacgtgc ctgactaatt tttcttattt tttgtagaga tggggtcttg   6180
ctatgttgcc caggctggtc ttaaactcct agcctcaagc gatctcccac ctcagtctcc   6240
tgagtaaact ggaccccagg tgcaagacac catgcccata aaaaaatttt aaaaaaattt   6300
```

-continued aattttaaaa tttttttgta gagataggat cgtgttatgc cgcccaggct ggtctcaaac 6360
tcctgggccc aagcgatcct cccacctagg cctcccaaag cactgggatt acaggtgtaa 6420
gctacctcgc ccggcctctc ctgttctatt ggtgctgtga gattcacacc tcacttgagt 6480
gctatgggct gaactgtgtc ctctccacaa atgtctatgc tgaagtcctg ccccgcaact 6540
gcctcagaaa gtgactatac ttggagatag aatctttaaa gaaataatta agtaaaaatg 6600
aggtcatatg cgtgggccct aatccaacat gaccagtttc cttgtaagaa gagcagatta 6660
ggacacagac atgcactggg gcggggggag gagactgtgt gaacacacag ggaaaacaca 6720
gctgtctaca aggaaaggag agaagcttca gaaggagtca cacctgtgga catcttcatc 6780
ttggacttcc agtctctaga aacagaagac tataaatgtg tttgctttga gacagagtct 6840
tgctctgttg cccaggctgg agtgcaacgg tgcgatctca gctcactaca acctccgcct 6900
cccgaaggag gcgtagtgta attctcctgc ctcagcctcc caagtagctg gtaccacagg 6960
tgtccaccac cacacctggc taatttttgt atttttagta gagacaaggt ttcaccatgt 7020
tggccaggct tgtcttgaac tcctgacctc aggtgatcca cctgcctcag cctctcaaag 7080
tgctgggatt atagttttgt ttttgagatg gaggtctcgc ttttgtcacc caaggctgga 7140
gtgcactggc acggtcttgg ctcactgcaa cctctgcctc ccaggctcaa atgatcctcc 7200
cacctcagcc tcctgagtag ctgggaccac ggtgcacacc actacattca gctaattcta 7260
tttttttgta gacacaggat ctcactatgt tgcccaggct agtcttgaac tcctggcctc 7320
aagtgatcaa cctgccttgg cctcccaatg tgcgactaca ggcatgagcc acggtgcctg 7380
gcaatttctg ttaagtcacc tagtctgtgg tactttgtta tgacagccct agcaaacaga 7440
tacacccacc gaaggccctg ataagtcctg cagtcaggag tctctgtgaa ccccgtgggg 7500
ctgggaggag aaagcaggga gcgtttgctg tgtgcctcac atgaatacag cagaagctga 7560
acacaactcc tggcatcgta tgcctacagg tccccttgga acagttctag gggggttgga 7620
gttccagggt ccattctgct taataacaat attaacggag cagccaaaat ggttccagtg 7680
aaaatggggt agcagcagct gtcatgcttg cacgccacca gccttcctgc gctatctctg 7740
ttctctcctc tgcaaagcag ctgctatttt gggctccctg tttttagatt gggaaccccg 7800
gaagttggtc agggcctcac cgctagaata tcttagagct gatattcaaa tgagagtcca 7860
attttttttt ttttgagacg gagtctcgct ttgttgccca ggttggagtg caaaggggca 7920
atctcggctc actgcagcct ccacatcctg ggttcaagtg attctcctgc ctcagcctcc 7980
caagtagctg ggactacagg tgcacaccac cacacccagc tagttgtttt gtatttctag 8040
tagagatggg ttttcaccat gttggccagg ctggtcttga agtcctgacc tcaagtgatc 8100
ctcccgcctt ggcctcccaa agtgctggga ttacaggcgt gagccaccgt gccctgccaa 8160
aagtccaagt tcttaacctc catgagggct tgagatgccc tcaggggcag ggagaggcta 8220
attctccttc tgagaggata atagggggttg gtggggcctg gggcacaggc ctggctcagc 8280
acaactccca gggactccct tgataagaag gtgaggtagg cactggctgg cagagcgacg 8340
ggaagagttt atttctctgg aaagggaggg gtagggggcg gggccagggg tcagggcagg 8400
gcaatgtcct ccagcttctt gtccagtgcc ttcaggtcat ccaggaagcg ggtcggggtg 8460
aggatgtgtg aggagcctgt gcaggggcag aggtttgggg aagatgttgg ggggcgctgc 8520
cttcgtcttt gacaggctcc cggtcccggc tggtgtgggg ctgtccctgt ccctcagcaa 8580
accaggtccc tgactccaag gactctggag tccagacacc tagaaggtac aagcccaggc 8640
cccgggaacc caagccccag accccagggt cccagtcctg gtgacttacc aatgagcacc 8700

-continued tcccacttgc cctcggtggc cctggtcacc tcgtaggcgg ccctcatctc tgacatggcc 8760
acaccgccca tgacatacac gatgagccgg gggcccgccc gggcttctat gccagccttg 8820
ttcttgtgcc agtgaccgaa gcgggcactg tgcagggcag gggcagaaag tccaggcagg 8880
aggccctcac cgccgccagg ccgcccacct aacacagacc caggcgtggg cgggggcggc 8940
cccggggcct cacctgacag cggcctggga gctggccgtg gggcggggt cggatacgaa 9000
gggccacagg ttcctgtcca gccggtcctc cacggcgtcc tggcggccga gaggcaggtt 9060
aggggaggaa ccccaggcat ggggtccggg gtcaggagtg ccccccacgg ggtattcagg 9120
ggccaagatc ctggcagaca ggaaccagca tctccacctc ctgcctctgg gggacccagg 9180
agtctaggcc tctagtccat tggggaccta gaaatctaga tccataactc actggggacc 9240
cacgaatcta attccataac tccttgggta cccagaagtc taaacccaca gttcctcggc 9300
aacccagtag tctgggcctc caggcccttg gggaccatca gtcaataccc ccagcccttt 9360
ggggaaccca gtgtctgggc tctcagcccc tcagagcccc agaagtccag gtattcaagg 9420
tccatgggga tgaggaggcc caggtctctg gcccccacgc agaaagaggg gccggggctc 9480
ttagagggac aaggaggaag ccaggaagcc gccccaggcc cattgccatt ggatggtgct 9540
gccctgggat cctgggaagg ccagggctgg ggctcagggg cactcctgcg ggacagggga 9600
acagactaga gagatatagc ggaggcagcc ggcaggtggg gaggaagtga ggctccccag 9660
cacaggcccc gctgtcaccc caattcctca gctgcgggct tggcgtgccc ccctcagcag 9720
agcagatcgg tgccaaggga atgccagcaa tgagcatttt cccctaagcc ctgaggctta 9780
gcacctcagc aggagggagg ctgagccgcc agccgatgcg gagggctggc ccccaccctg 9840
acctgccacc cagtacctcc attacatcct tgatgaccgg ggtccagcgg gacagctgat 9900
aggtgggctc catgcgttct ctcggctcca gccggctgga ggtccccgag ccctacaggc 9960
agggcaggga gggcagcagg gggattgagg ggaaggaggc tggtcacaga ggggctgcgc 10020
ctggtgtggc tggtagggtg ggggatggca ggcaaagatg gggaagtgga acagagagcg 10080
agagagagcg agagacagca agaaagcgag agagagaaac agtgagccag agagagacgg 10140
agagagaaag ccaaagggag agagagcgag ccagagaaag acaaagacag aggcagagat 10200
aggcaaagag ataagaagca gtgagacaaa gtatgaaggc aaagagagag acaagagatg 10260
aagcaggaaa cagagagagg aagatgggga cagaaggggg acggagaggg gaggggagca 10320
agacagagaa cagagagaaa ggggaaggca gagagaaggg tgagagagag agatatggag 10380
aaacagtgca cagcgagatg gatgagggat gggggagaga tggggacggg gtgagggcac 10440
cctggagggg gacgcacagg gccagagaga gacaggagag gctgacccaa gagtcaagca 10500
cacacatggc tgtgtgtggg tgctggatgg gtgcggggga ccctcagaga cccctgggag 10560
cccagataga caatgtggtg tagcccccat gctggggacc ctactccctg cctctagcac 10620
tcagaccacc cgctcccaac tgcaccactg ccaggaccag cctggcagcg accatgtctc 10680
acttcccctg cctattgtgt aagctgggac tgggagaggc cccagtgtcc tctgggcccc 10740
agaccagacc cgaaacactg cttttggcct cccagcaacc acaccacgcc aggaaccaca 10800
ccgtgcctgt gcaccaatgg ccctctgcct tgcagagccc cggctgtgat ccgcaccctc 10860
tcccagggtc cccccatgcc cgctcctggc gtaccccggg gttggtgaca gtgcctccca 10920
gctgctccag gttacggatg aggctgctgt gcgcctgtac attggcatgc tggatcagct 10980
tggccaggtt ctcctcactc acacctgggg gacgggaatg ggcagggtgg aggcggcggc 11040
caggtgagct cccaggttta ggggagtttg gggtgggctg aggagctccc aggactctga 11100
tgagagaacc ttgcagtggg gagggcctca gtaccctgtg ctagtgtgag caagagtggg 11160
aaacctggag ggggtagatc aggggctcct ccagatgagc tgagggagcc ccacatctat 11220
aggaatcaca gatgtgaggg tttctacgtt agcagggagc cctcacctca gtggaggaat 11280
ccccaagcca atggaggagg gttcccgggt ccagaggggt agctgtgggg gttggtgagc 11340
ccggtgagtg caaatgaccc aaggagagct gtggggttca gcagttccca ggatcgtggg 11400
agacgctggc aaatggggac gttccaactc cctgcagccc ccacccacca ttccgaagga 11460
ggatgtagag cagcaggacc cggatcttgt cgtaggcggg caccgccgcg tccagcagca 11520
ccggaacgat cagcttcatg gagtccttga tcttctcccc ctctgcgtcg gagcccatgg 11580
ccaggtcctg cgggcatggg gtcagccgtc caccggccgc tatgtgtcag ggaaggggat 11640
gggagaggcg ggccaaggac atccccagga tcctcggcaa gaggacattt gggtcctacc 11700
tcatctcagc accaggtctc tcaaggtccc acccctgtcc agggacagtc tctccacagg 11760
ccctgctcct cacccaggtc ccacctttcc agtgccccac ccacctacac acaggtcaca 11820
ccactatcct gagactacct ctccaaggct ccacccctca cccaggtccc agctctccaa 11880
ggctccaccc ctcacccagg tcccagctct ccgaggctcc acccctcacc caggtcccac 11940
ctctccgagg ttccacccct cacccaggtc ccacctctcc gaggttccac acctcaccca 12000
ggtcccacct ctccgaggct ccacccctca cccaggtccc acctctccaa ggctccaccc 12060
ctcacccaag tcccacctct ccaaggctcc acccctcacc caggtcccag ctctccaagg 12120
ctccacccct cacccaggtc ccacctctcc aaggctccac ccctcaccca ggtcccacct 12180
ctccgaggtt ccacccctca cccaggtccc acctctccaa ggccccgtgc ctcacccaga 12240
tcccacctct ccatggctct acctgtctcc cagctcctac ctctccaagg ccccacccct 12300
cactcaggtc ccacctctcc aaggctccgc ccctctccca ggtcccacct ctcttaaggc 12360
tccacccctc tcccaggtcc caccccctcca aggttccacc cctcatccag gtcccacctc 12420
tccaaggttc caccccctcac ccaggtccca cctctccaag gctccgcccc tcacccaggt 12480
cccacctctc caaggctccg cccctctccc agggcccacc tctccaaggc tccattcctc 12540
tcccaggtcc cacctctcca aggctctgcc cctcacccag gtcccacctc tccaaggctc 12600
cattcctctc ccaggtcgca cctctccaag gccctgccta cctctccaag gtcccaccca 12660
cctatgaata ggccacattc ctgtcctggg accacctgtc caaggctctg cccctcaccc 12720
aagtctgacc tctccaagcc ccatccacct atgcacaggc cacaccctca tcctaggacc 12780
gtttctccac aagacccact ccttccccac caggtcccac ctctctccaa ggcccctcca 12840
cctctccaca agccctgccc ctcccccaga accccccatc tctacagttc agcccctccc 12900
caataccccg ccttggcagg accatcaccc ctgccccccg caagccctgc cccacctgct 12960
ccacactaca cagcttctcc accgagccct tgaagtgctt catacaatca tctgctagat 13020
gcaggtgcgt agaatactgc agggtgcagg gtgggggttg ggggataaca aaggctgagt 13080
caaggcagaa cgcagacaga gcatggggtt gaggggccga ggtgtccccg ctccctgccc 13140
acccgagcac accttattca gctccttctg gtactgcggc atctttttca ggatctggga 13200
taggtctttg atgttcgcct ggggaagtag ggggaagagg gtagggattg gggggcgaag 13260
ccaggcagtg cccacctggg tctcagtcca ggctcgaaat ccaggctgtg gccctgcgcc 13320
catggggagg ggggcttcct tccaccagcg cctttggtga cctgggtccg cccctacctt 13380
gtccgtggtc agcctcttgc tctcacagaa ggtcctcagg agctccgtga ccttcctggc 13440
catgagggtg ggcgggggtg agagtgaggg gagaggagcc acaggccatg ggtgagccca 13500
ctcagggggg acagggagag gtggggtgaa attggaggcc agtctggagt cacacgaggg 13560
gtgctcatga gggccaaaga cttggcagca gccagggatc ccaaggccgc taccaggccc 13620
acagtgggcg gtgggggggg gatccggtcc ccgtgtgcac gcacttggac acatctgcga 13680
tatgcatgtg gcgaagctcc acccacaagt catcgtcctc gtccagcaag acggccttct 13740
cccgcgcctc gctcagcccg gtggtctcat acctggggag gaaggaggga gcctgggggt 13800
caggggagct gaggactggg gaaccaggtc agtggcaagg gtggggacgg gttccaagtc 13860
tgcagacctg tatgtgtcct gctctatgtc cagcagatca tacgccatgg cctggaacgt 13920
gagctcatgc agtagtgggg acacggggtc agctgcccgg tccattatca gcagctggga 13980
gcgggttttc tctgggccct ggggtggggt ttagggcagg aatgaggcac tgaccctgag 14040
ccggttgggg ctgcccctca cctcccaagc acgcccctc acctcgccca gactgggagt 14100
gtctgccttg aaggcgttca gcttggccag gacggcgtgg gccaactggg ctgtgtcctc 14160
tgggcccctg gcggggaggt cagacacggg ggacatcatc aggggatggg gtcaaggatg 14220
ggtttgaagg tgagagtcag gggccagggt agggccgggg ctggggtcac aagagaggtt 14280
aaaggttagg tgttgcacgc ggttaagggg gggtcggcat cggggtgggg ctgggtgggg 14340
tccccacttg cggtagcgga tggccgggta ctcctgcagg gtggcgcaca gcgtggcaat 14400
ctgctgggcc agcacctcga gctgccgcgt gcgctcctct gcccggaagg ggcagtagag 14460
gttgtaggtg ctgtggggag catcgaggga gaacacctgg gcgaggaggg gacagaagca 14520
ccagggttgc cgctgcaggt gcacacctgc cccgcttccc gctgccgcca cctgcacctc 14580
ctgggagccg tccctggtcc ctgaagcctg ctttgccgaa ttggaggcag gcccaggtca 14640
accctaaacc catgcctgca ggagtcagtg gataaatacc ccagcccgtg tcccttaagc 14700
tggctggaca accccgcggt gcgctctacg ctgcccctg caagggccta gtgggataga 14760
actcaaggca agagctcctt ggactctgtg ggtacctccc ctttttaaaa ttttacttta 14820
tgtatgtttt tgagacagga tctcgctctg tcgcccaggc tggagggcag cagtgcaatc 14880
atagctcact gcagcctcga cctcccgggc tcaagcgact ctcccacccc agccccatga 14940
gtagctagga ctacaggtgc acgccaccac gccaagctaa tttctttctt tttcttttt 15000 taagagacgg ggtcttgctc tgtacccagg ctggtctcaa actcctggcc ccaagtgatc 15060
ctcctgccct ggcctcccac agcgctggga ttacaggtat gagccactgc gcccagcctc 15120
agtgtctgtt tctgagggaa caggggacat ttggtcacaa acccccaccc cctgcccagg 15180
atgagcccgg gccgtacctg ggcctcgtag gggaggaagg caaggtgaat ctccttcaac 15240
gtcttcacca cctttgccag acgagagcgg cctagctcac tgaacagggg ctcggggcag 15300
gctggggtga ggcaggagtg gggcatcagg ccagagcagc cccacacct ccttgcccca 15360 cccaccaaca ccctaggctc tcctcactca ctgtcggtga agaagatatg ggccgctttg 15420
taggtgaaag tcggggtccc ctggaagtct ttgatcaggg cctgaaccga ctggggaagg 15480
tggatcactc tctgggcctg agcctgcaca cctaggctca ttggctgcct aggcctccca 15540
gccacccccc atctgccacc atgtgcaaac atggacggac ggggacatgt atatgtgcaa 15600
atgcacacta gtgtcgcacc cacatgggca cacgcgcaca cacacagatg cacgcacgca 15660
cacacacata cacacgcatg cacacatgca cacacacaca gatgcacaca cacatacaca 15720
catgcacaca cagagatgca cacacataca tacacacatg cacacacaca gatgcgcgcg 15780
cacacataca tacacacata tacacacatg cagacactga tgcgcacaca cacgcataca 15840
cacatgcaca gacgcataca cacacgcata cacacgcaca cacagatgca cacacataca 15900
tagacacatg cacacagatg cacatacata tacacgcata cacacatgca cacacagata 15960
cacacagacg cacacacaga cgcagacaca tacatacaca cgcatacaca catgcacaca 16020
gacagacgca cacacacaca tacagatgca cacagatgca cacacacata catacacacg 16080
catacacaca tgcacagaca caaatgcaca cacagaccca cagacacaca cgcatacaca 16140
catacacaca aatgcacaca cagacgcaca cacatgcaca tgcacacaga cacatacata 16200
gacacacatg caaacacgca cacacatgca tacacagatg cacacacaca tgcacacaca 16260
tgcacacaca tacacatgga cacatgcaca cgtatacaca tgcacacatg caatcacatg 16320
catgcagaca tacacacaca tgcacatgta cacgcatgca cgcgcataca cacacgctca 16380
ctcatgtagg caccttctcc gtggggctca gcaaataaat ggcctccaga ctgggaatgg 16440
gttcccgccg tttgttgatg tcttcaacaa ctagtaggaa cagaggaagg gacacaggtg 16500
ggtggcatcc aggcagggcc acgtggggag tctcaggtgt gggggttgg aggcttgggg 16560 aggaggggtg gatgcttagg agggactgca ggagaaaccc acttagggac caccagctaa 16620
gagccacacg acagggttct gcaggggttg tgcagccaac tgggttcccc aaatttacag 16680
acagggagac tgaggttctg agaggacagg ctccctcagc acctatccct caatggcaaa 16740
gtgactggga caccacctgg ggtcacccat agaaggctct gcattcttgg gaccccacat 16800
ccagagtcca ccctgggagt cccacacagg gctccacgag ggagctgcac ggtcaggaag 16860
gggctgcagc cagggagtgc tgcaggggag gcctgcaatc catgggctcc cgcagtcagc 16920
ttgcaaggtt taagaatgga tttggtcaca tgatccgggc tgtccgtgca gggagctgcg 16980
tacttgggag ttctggacga tttgagggga tcctacactc aagggctgaa ccctgggaga 17040
ggggcacagt caggggttcc cacgctcagg tcccatctca ctggggacgc gttcactcac 17100
tggtgatgcc ctcagccagg atatctgaca ttttgcagca ggaagacaag atgcgcatgc 17160
ttgggtgatc catgataagc acctgtccag atggatggac agatggatgg aggagcaggc 17220
ggaagaggcc acagctggcc ccagaagggg ccaaggcagt gggaggggca gtttcaaggg 17280
ctggctgggt gggaggaccc agaacccatt cacccaactc cacccatgtg gacaggcagt 17340
tcttgggggt cccacattca gggtcttccc cataggcctg atgatgagct gcctctgggt 17400
acccagccat ctgcctcacc cctaccttcc actccccatc cttcttgaca ctccgaataa 17460
ctccgctcag aatttctgca gggaagggag gggaggggtc agaatgctgg ttctctggtc 17520
ccaccactgc cccaagcctt ctcagccttg gggctgaacc cccatcttaa ttcccattta 17580
cttttttttt ttttttaaga gaggaggatc tcactctgtc acctaggcta aagtgcagtg 17640
gtgtgatcat aactcactgc ggcctccaac tcctgggctc cagcgatcct cttgcctcag 17700
cctcccgagt agctgggact acaggtgcat gtaccaccca cagctaattt atttttattt 17760
ctgtatagat ggggtctcgc tatgttgccc aagctggtct caaacttttg gcctcaagca 17820
gtcctcctgc ctcggcctcc caaagtgctg ggattacagg tgtgagacac ggcacaggaa 17880
tcatttattt ttagccccca gttctgcaaa ttggcttctg gggtcacccc caatttacag 17940
acagggaaac agattcttag gcaacatgta actcacctac gcatcctgag tgtctaagtg 18000
gcagagtgct ggggcaaaag gtgccactcg ataaacatgt tttaggtgaa tgaaaagagg 18060
agaaccggga tcatctacag ctctatctgc ctctagcgcc aggctctcgg cttccccacc 18120
tgctacctca agtattcctg ctgtgagggt ttcagccagt ccccccaacc tggtctaaaa 18180
tgtaggaccc ctggttccca gctctgaggc atgcctagct gaggctatcc cactgacctc 18240
cggtctcagt ttcctcatct gtaaaatgga atcacttttt tctaatctcc cccaattaaa 18300

```
ggggtttgag ctacagaccg ccctgcctag aggagagagt ggagagaagt aacggggtgg  18360
ccccgcccag ccacgtccac tgtgtcatgt ccactgttat caagacggcc agggcggaag  18420
gagcagctga ggccggaact ccccggggtg gaggaagagg cgccctccac ccttccccca  18480
agaaccgggg ccggtgaggc ctggacgcct gcgtcctcca gctgcaaggc gctcctggaa  18540
atggggcaag gaggaagaca tcccctacac cacccctgtg gggcctggac acgtcccctg  18600
agcgctcaca gcacctaggg tcgctgacca gagccctagg aggccccaag aatccagccc  18660
ctgaactttg cccggcttaa gagatcctag agtgtgggca tccagctgtg ccctcctccc  18720
ccggcaggca ccctaggagg cccaggagtc cgggccccag cctccgccac actctacccg  18780
tcccctttgg gtccccggag tccggccccc caattttgtt ctgttctggc accggagagc  18840
aggggcgtcc agctgggaac ccgtccccgc ccgccccctc gagggtcagg tgctcggacg  18900
cccagcccgg cccccaactc ccagccgcca tgaaacccag gatcccagag cccgtgcgtc  18960
cccgaccccc gtcccacacc ggacgccaga gcccggcccc ggagaggcac tcactttccc  19020
ccaccaccgc cttcagcccc gagggcgcca tcttccccga ggggcgccgc cgccgcttcc  19080
gggtgtgtcc caaggtgggg gcgtggccgc gcgtcaccca cgtggacccc gccccgcgcc  19140
ctgtccccgc cccctgcgca cctggcccct ccccgccgtc ggttctcgcc caggcccagg  19200
aagttgagtc cctggcgggg aggacgggca ggtgcgtccg cgctgccgag cacgaagtcg  19260
ctggaggtgc acacctcgac gacacgctca cagatgggag ttcagacaca cacttcctgg  19320
cttgcgtgcg aagcaggatc gcagggcaat aatccctcca tcttccccgg gaggttctgt  19380
gcctgcaaga tacacggcac ccactcgatg ccaccgggcc gccactgtct gggcctggga  19440
tcttgaccca cttgccttct gtacttcagg gtttagaggc agcagcagca gcagcagccg  19500
tcttggataa cttttgatgg attcaggagg cctggagacc tcttgtgtgc aggcacctgg  19560
acataatttt cattcagtcc tgcccaatgt tccgacctgg actgcggtgc cgacgaggaa  19620
accgaggctt agcgggatcc ctaatccaag gccacgacga gtgagcctgc tgggttcaag  19680
ccaggagcct gtccccaggg ggcatttgtc acagccttac cctcttccgg gagggcgcaa  19740
cgcttaccct cgtggaccaa caatcgaatt aacatgctga tacacacatg ggtgagtga   19800
cgccctcaaa tgcttgcaaa cacagacaca cactcggaat ttcagaagct gcttctgctg  19860
tgtgtcctgt cgcttggaag gcacagcccc agcagcaccc atacaaaatg aggtctccga  19920
tttaaggtgc gaggtatgtg tgcaaacaga ctcttgctgg tctgagctgg ttccttcgct  19980
cggccgtgtt gatgaaggta ccaagccccc tgccacttac atgggacata gggagtgaat  20040
cagacccgaa ggtctggggg agataggaaa ggatccatgc tgccctaaag gaaataaact  20100
aatgtgacaa caagtgccac agaaggtagg ggtgggaggg gactttactg aggatgaccc  20160
ccgagggcct ctctgaagaa gcagcctttt gacattatcc ctaaatggat tctagaagca  20220
gccacacagc atgtccaggt agagaaggga ggagccccga gcttaagaag gctggagggt  20280
gggggcagca ggggccagac ttctgtagga caaggtcaga ctgacccatc ccagtgccag  20340
gatgcaggac tttcagtgct aaaaatagga cagtcacagg caaaccagga cggttggcaa  20400
ccgtaggtag gagtttgagc tatttcttcc tttcctttcc ttttcccttc ctttcttcct  20460
tcttctccct cctccccatt tttgtttgtt tttgttttgt aaagagacgg gtctcgctct  20520
gttgctcagg ctggagggca gtggcacgat catagctcac tgcagcctcg acttcctgag  20580
ctcaagggat tcttccactt cggccaccca agtagctggg actacaggtg cacgccaccg  20640
tgcccggttg attttgttgt tgttgttaag agacaggatc tccctatgtt gcccaggctg  20700
```

-continued

```
gtatcaaact cctgggctca agggatcctc ctgccttggc ctcccaaagt gttaggattt  20760
taggtatgag ccaccgcacg ctgccccttc ctccttttgt aacagcttta ctgagatata  20820
attcacatac catacaactc gctgacctaa ggtgcgtaag tcaatggctt tcagtatttt  20880
tggagttgtg tgtccattac cacaatccat tttagaacat ttccacaacc cctaggtgtt  20940
tgggttttgt cttctcaaga gttttgagca ggggaaggcg gggaaccctc cagatcctgg  21000
ggggatggaa gccaggaccg cctccagctt ctcagcctga ccccttgggg ggacagagag  21060
ctgttagggc cagccacccc accactaacc cccaaaagat atgaagtact aatccccaat  21120
accccacaat aggatcttat ttgaaatggg gttagtatag atattagcag tgagcatgag  21180
gtcacactgg agtagagtag gcccctaatg caatatcact ggtgtccttg taagatagtt  21240
atatgtctgc ctggttctgt gtaggtggtt ggggggggtgg ggaaatgggt atatgaagac  21300
tgggacacag agggagaatg ccatgtgacc acggaggcag ggagtgaaga gctgcagtga  21360
caagccaagg acatcaagga cggcaggcca ctgccaaaag ccagggaggg gcaaggaggg  21420
ctcctgagac ctggttttca gagggagcac agctctgcca acaccttcat ttcaggctgt  21480
ggcctctgga acgttggctc aataaatttg ttaaaaaaaa attttaaagg ctcagcatgg  21540
tggctcatgc ctgtaatccc agcactttgg gaggcccagg caggaggatc acatgaaccc  21600
aggagtttga gactagcctg ggcaaaatag tgagacctca tctctatata aaaatatata  21660
acaaaagtca acttatgtgt tttaagccat ctggtctatg acactttgtt ctggcaggcc  21720
taggaaaggg atacacgtac tgaggagggg gacacttcat tggcatagag ggagagagtg  21780
tgaacttggc cttttgtgga acagaggagg ctcgggcaga ggtggtgata gtgcagccca  21840
ttcattctga gatgaaactt ccactggttt ccgtaaaggc gtcttgggga gggaagggaa  21900
ggggatgggg acctcccagt ggtatcccct gcttgggcac tgagggaaag ccacagtggc  21960
tcgggggaaa aggcagggac gtcctctccc cgcctgcctc tgtccccagg gagtctcgcc  22020
tcctgttccc acctggggct agggtgatag aggagaggag atagctcaac ctggcattta  22080
ggtggtgtgg gaacaggaga ccccagactt tcttgttttg gggtctgggg caggcaacca  22140
ggctccaggg acagtgagtt gaaggaaggg tggctgggag accccttgac ttgctgccaa  22200
ggagacagag ctggagctag ggtggccggt ggtgtctgag gcaggtgcag agagggaggg  22260
agggaagggg cctttgactc caacctcctt tttctgtacc gactgcaggt ggcagctgcc  22320
ctttcaggag ccagtggggg aacctgggtg gctgggtggg gacacctgca agtcctccct  22380
aagccagcta ccaccctaca ctgttggcct cccttctcca actgtgggga tgctgctcag  22440
gccttttgtg acatcacacc tgagagtccc tggggtccag tcattgctgc tgggcacagc  22500
gaggtccaag ctcaggtcgc cctgccccct acccaccatg ccagatccag catcgttgtg  22560
ggcaaacaat tatctggatg atctttatgg ggcttaagct tgggtgggag cagatggggc  22620
atgagctggg gatttgggga tggggggaat ccacaccccc acgtcctgga cgtttaaaag  22680
gccctctctg gcactgggcc ggggcagagg ccagcagaaa agtgactgga gtccagggac  22740
atgatggatc aggaggagaa gacggaggaa ggctcaggcc cctgtgccga ggtgagaggg  22800
ccctgccccc accccacccc cagctcaagg tctcagagcc catgattgac aagactagtt  22860
tgtagggcac ctaattaacg agtgagtctc ctaggacccc ctgacccagt tgtggctgta  22920
gaaaggggct ggtgggcttg ggggtctgag tgccaggccc cagggcagag ggcagggctc  22980
tccgtgtgga cccctattga tgggagatgc tgggacctgg gggtagctcc tgggccatgt  23040
ttccctgatt cgtgtcccag ctcccaggcc acactcatca ggccccaatc taggacggcg  23100
```

```
ggacacgcat cggagcctgt cccttgaagc ggtaccacgt gaagtggcac tgctggccag  23160
ggcccctggg gcgggggccg ggattgggaa ggagactcat gtctcattca gaacagctct  23220
gcagagagga tcggcgggga ccatggtgag agctgaggaa gtggggacgg caggccccgg  23280
ggtcagggtg tgagcaagct ggctaggaag tttggggagg ggcccccaag ctgaagggcc  23340
aaccagactg agcgagtctg tccccaggcg ggctccccag accaggaggg cttcttcaat  23400
ctgctgagcc acgtgcaggg cgaccggatg gagggacagc gctgttcact gcaagccggg  23460
ccgggccaga ccaccaagag ccgtgagcat gggcacgggg gtgctgtcca tggggcgtga  23520
acggggtggg agtgcagggc aagtggtcat ctggagggcc tgggggcacg ggatgtggga  23580
ggtggttgtg caccctgaag catctgtgtg ggggtgaagg ggtagggttg ggggccccca  23640
ctccggctgt gtcctcccaa gtctgtgaac gtccacgcag agagcgaccc cacccccgag  23700
atggacagcc tcatggacat gctggccagt acccagggcc gccgcatgga tgaccaacgt  23760
gtgacagtca gcacgctgcc cgcttccagc ccgtggggtc caaggtaggt gatgttctgg  23820
cgatgtcgag gagaaacccg ccaggcagtg ctctccgatc ctgccctcca ccccagccag  23880
gagggaacag ggcctgcccc atctctgtcc atccgctgcc ctgacttcag atgggaggac  23940
caaggcccag gcagtggcta gaggggccca aggttataca ggggccatgc tagtgtaaga  24000
cccatggctg gaacttgtgg ctcctgcccc caagtctgaa ggttctgggg aggccaaagg  24060
gagaaaatag gaccccttcc taggaaagta tcccagggag gaagtcacgt aagctcacac  24120
ataggatata tacatctgta tactcacatc tgttgacttc acacatacac gaagcttggg  24180
ttctgatcaa gatcccagcg agggccccaa gacctgccac ctcacactca aatgccaccc  24240
taaatggcag atattgaggg taaacataga ccagtgctca caatgaggtg ggacacggtg  24300
gctacctgca ccctctctcc attgttcgcc acctgtggcc ggcactgccc ttgagccctc  24360
cccctggctg acccctcttc atccacagga cggagcacag aaacgagctg ggaccctcag  24420
tccccaaccc ctgctcaccc ctcaggaccc gaccgctctc ggcttccgtc ggaacagcag  24480
cccccagccc ccgacacaag ccccctgagg gcctgaggca tcctgggtct cactcggccc  24540
ccaaaaactg ataaaagaat aaaacactta aatgaataac aaggaactga gtatatgtat  24600
atttcatcag gggaggggct aggactccca cttggaggcc tcaggagttc tgctgggcgt  24660
cgcgaaggag cttctcctcc cgccgcttcc gtaacctctc tttgaattcc tctatctctt  24720
gaagctaggg gtggagaagc gggtgggaca ggaagggggg aggggcacac acctcagagc  24780
cgggaccccc cccccccgcc cacctctccc accaccctgc cccagaccac ggcttcaggg  24840
ttcagtgtct tcactggaag ccccctgcca attacaaagg ggtccgcgtg ggatccgctt  24900
cactcttcca ggagaaggca ataaggaaac catctactcc tctgctctcg gttccttact  24960
catggctgag agtaaaatgt ttctttttga gacaaagtct cactctattg cccaggctgg  25020
agtgcagtgg cgtgatcttg ggctcactgc aacctccacc tcctgggttc aagtgattct  25080
tctccctcag cctcccaagc agctggaatt ataggcgcct gccaccatgc ctggctaagt  25140
tttgtatttc tgtagacatg gggtttcgcc atgttggcca ggctggtttt gaactcctga  25200
cctcaagtga tctacccacc tcagcctccc atgccctggg attacaagca tgagccactg  25260
cgcctggcct aaaattttca tctaaaaccc atcccggata caagaatcca gcctcctcca  25320
tccctctggc aggaagaaga gatcacttac cttctcaggt ggccacagct ccctctgtaa  25380
ggaaaagtca caaatgggac acgagccaaa ggcctccaga gccccacatc agggcagggt  25440
cggcttatgg gaggcagaca ttagtcccca gcagactgct gccccacacc ctctcccacc  25500
```

-continued

```
cctggaatga accctcaaac actcctctta tgcccacctt gcgctgtatg acatcgtcct  25560
caaaccactc ggcctgattg gaaacccaga acatagccac agggaaagtg aggtagatta  25620
tcatctggaa tggcagaggg tgggtgaggt gagctccccc caagcaatgt gcagaggctc  25680
ctcagagcct gggggaccca tcctactgca gagtccagaa gcgcctcgtt acggccgacc  25740
caagaatccc agaactccca ccaagggtac agaaacctcg caccctaaaa cctaactcct  25800
ataatccagg aggcctcatt cctgaaagtt ccctctgagc tggagtcttc ctctcaaaca  25860
cagacagaca cacagacgcc ccagctacaa tcaaaagcat ctcctcgaga cctcattacc  25920
catccccact taagatcccg ggagcacccc caaacccagg aggcgtcact cttcaactcc  25980
acttctcgaa gtctaggaat ctccctgtca tagacaccca cccaccacga gcccgagagc  26040
tccccaggga tcttaagtct tccttcttta gagccccctt ctcagctcac ccctctctga  26100
ggtccttcct cggaccagcc ctctcacagc ccccaaaatc agaagcacaa atccgagaac  26160
ccccccagcc cagcgtcccc tctcctggat ttccaaccag aaaggtcctc tcaaatctta  26220
agagctttct ccttggagct ccctcttcct ttgaagtccc cccatttcca acctcatctt  26280
cagatccagg aagatcccct gcccagcctc ccaacccact cctgtgtcca ctgacccgaa  26340
atatctccag cttcaccccc atctcgtttc tcccggtcaa caaagccagt tccgcccaaa  26400
gccgaccctc cagcaagaca gaagctcact ggtgttttgc acgctccatt gctgaagctg  26460
attggccaat gtgtatcctc atggcgcatc ttctggcgcc tctattctgc ttccggtcgc  26520
tggcgtcgtc gaaaagaagt caataacgtg ggcctgtccg tcaaaaatga tttaaccaat  26580
agaaaacggg tctggctcgg aggggcgggc cgtcagtggt agacgtcata agcgcgcgac  26640
tctctcctgt acctgggcat ccagaaaaat ggtggtgatg gcgcgactct cgcggcccga  26700
gcggccggac cttgtcttcg tgagtccaca gaggagccgg gggtggcctg cgttggggca  26760
ttgggacctg gacgccgcag gggatcgagg ctgggtcggc aaggagattt aggccgaaac  26820
tgccaggcca aggtctggga accctaatgg gccagagacc ggatcgtcat gtccgcaccg  26880
aactgtccag gagtaaaaat atggtgttgt atcttcgggt ctgagtagaa aaccactgtc  26940
gaagggaagc gtctagcctc ccgaaccagg ggcggaaatg ggggcgtgca gggaatggga  27000
gaggaggaag atcgcataac tgaaccttga gaggtgaaga tcggtgtctg aagtaaaggc  27060
ttgcttacga ggccagggtt ctggtttctg ggatgaaggc ttggttttct ggatagcggt  27120
ctctaggcct ggactgcagc atgacagttt ctggggtggt ggccaggcta gaagaaccct  27180
ggtgatgtgg agcttgtcag gcgatggcca gtgaaatact tactctctgg agtagaggcg  27240
tgacatcttc accagattct tggtgtgcag agttaaaggc ttggcttctg gtgtataact  27300
cctcctgtga gataaaggcc tagcttttaa tttctggggc agagttgagc tagacgctgg  27360
ctagtgggat cctgggggcg gggctagtgg cttggaatct ggacctgaga gccctggtgg  27420
ctggggtaaa gatctggtca tctgggcctg gggtggagat gggtcagatg gtgacagtgg  27480
gagtctgagg ggcaaaggcc tggtgtctgg gaagaggcac gttttgaaga agtggggtct  27540
ggtgtccagg actggcatct gggccagggc cttggtatct aaggagtctg accatctggg  27600
gcagaaagcg agtggtgatg cggactcatt cctggcccag agccctaatg actgagaagt  27660
ctgatgattt gggttcgatt ttgggtagtt gaattctgag gggtaaaggt ctgggccact  27720
gtcttggtgt cgggcatctg gtttggtgcc tgggcatctg gtgacctgac ttccttggtg  27780
ggtggtggga tctaggtaaa agtccggagt ttggacctga gccccagcag tgggatggtg  27840
ctgcacacag gctctgaggg taggcctctc ttcttcccat tccctggccc tggcaggagg  27900
```

-continued aagaggacct cccctatgag gaggaaatca tgcggaacca attctctgtc aaatgctggc 27960
ttcgctacat cgagttcaaa cagggcgccc cgaagcccag gctcaatcag ctatacgagc 28020
gggcactcaa gctgctgccc tgcaggtggg aatggctcca gctgccctgc ccaccagccc 28080
ccaccccacc tggtccagtt ataacaaaac tgccaagtgg gtcccgggtc ccgggtgatt 28140
gcttcgtgtt tcatcactga cctgtacatc ccttgatggg tcagcacacc ttctctgatg 28200
tcccagtctg tccctgtcat tgctgagaca tgtcacccct cccacacccc ttcttcccac 28260
atttgccaac tggggcaggg caaatggttc tgggggtgtc cataaagctg accgatcagc 28320
atctgtcccc tcctattccc cagctacaaa ctctggtacc gatacctgaa ggcgcgtcgg 28380
gcacaggtga agcatcgctg tgtgaccgac cctgcctatg aagatgtcaa caactgtcat 28440
gagagggcct ttgtgttcat gcacaaggtt tggggctcgg cgaggggatg aatcgggaag 28500
tggagctcag tccatggtgg tgggtggggc ggggacaggg gctgggctca gcatgttagg 28560
gatgggggct tggattcctg ttgcttcttt gcatgggaag ttgggctgga ctcagtcctg 28620
gagctggggg tttctgggtc ccgccgcatt tatgtggtgg ccccaggtgt ggctcagcca 28680
caggacatcg agtgtctgtg gccaggccat ggagtccgtg gcttagcccc agccgcctct 28740
ccccacaccc ccagatgcct cgtctgtggc tagattactg ccagttcctc atggaccagg 28800
ggcgcgtcac acacacccgc cgcaccttcg accgtgccct ccgggcactg cccatcacgc 28860
agcactctcg aatttggccc ctgtatctgc gcttcctgcg ctcacaccca ctgcctgaga 28920
cagctgtgcg aggctatcgg cgcttcctca aggtgagcct agcaggtgcg ctggttcccc 28980
aggttagttt ccagaaacgg cctcactgtg acactagctc cgtgtaggat gtcacccagc 29040
agacgggatg tgggaagagg ctcctggaga tgcatgtgtt ttgttgttgt ccgtgattca 29100
tgtctttatt ttccaaatag tttgttcaca ctggtttcac attaggcata gcgatgggtg 29160
ctgaggacag tgtgactaag acactccctg cctgcacgga gcttttagtc taactaggaa 29220
gacagatgca tatgagctga tggcatgaac tagagtaaaa ccacagccat gaagagggcc 29280
aggaataagg gtggggagaa gcaggcaggg tggagagtgg aagcaccagc cgggcgggag 29340
tggggcatgg tttgctcaaa cttaaagtat ctgttttatg acgtttggat tctaagctgg 29400
accagtcagg actgaggctg gacccgtggg gcccaggctg gacactatag tcaaggctgg 29460
acccatggga tcaaggctga cccaaagggg ccaaggctag accagtcagg actgaggctg 29520
gactagtgga gccaaggctg gacccattgt gggttggggg tcaattctaa cccaaaagga 29580
ccaaggctgg accattgggg ctgagactgg accaccgcag tcaaggctgt gcccttgcgg 29640
gtcaaggcta acccaaaaag tccacagctg gtctagtcag gactgaggct ggaccagtgg 29700
agccaaggca ggacccacag gggttgagc ctaacccagt ggggccaagg ctagaccagt 29760
aggaaccggg ctggaccagt ggggctgagg ctggtttgac agggcttgct tttgcccaag 29820
acactcataa atgggtgggg ggggacgccc cgaagccact gaatcgggag gtgggcgtag 29880
ccctgccacc ccactgactg cctgaggggt ggctcggtcc ccagctgagt cctgagagtg 29940
cagaggagta cattgagtac ctcaagtcaa gtgaccggct ggatgaggcc gcccagcgcc 30000
tggccaccgt ggtgaacgac gagcgtttcg tgtctaaggc cggcaagtcc aactaccagg 30060
tgggcctgcc gggagccggc aactgggtgg gagggccacc ccctccatga ctgagcctga 30120
gactctcccc cactgcccca tgccctgcag ctgtggcacg agctgtgcga cctcatctcc 30180
cagaatccgg acaaggtaca gtccctcaat gtggacgcca tcatccgcgg gggcctcacc 30240
cgcttcaccg accagctggg caagctctgg tgttctctcg ccgactacta catccgcagc 30300

-continued

```
ggccatttcg agaaggtgca tgctggcaca cggggctctg ggttcggggc ggggtctccc  30360
tccgacactc ggggacacat gttgacacat gcacagacag aaaacatgcc atttatggct  30420
gggtgtggtg gctcacacct gtcatcccag cactttggga ggccgaggcg gtaggatcac  30480
ttgaggtcag cagttcaaga ccagcctggc caacatggtg aaaccccatc actactaaaa  30540
atacaaaaat tagtcagaca tggtggtgcg cgcctgtaat cccagctact cgggaggctg  30600
aggcaggaga atcgcttgaa cttgggaggt ggaggttgcc gtgagctgcg atcgcgccac  30660
ggaagtccag cctgggtggc agagcgagac tccatctcaa aaaaaaaaaa aaaaaaaaaa  30720
agtgccattt ttgacagaca tgcatatccc tgcacacgat tactatcctg ctgagggtgg  30780
gggagcactc ctgcccgcaa gcacgtcagc ctttggagtt cagccacatt ttgcgttcag  30840
ggtttcaccc tcttggctct gcggcctttg ccccaactaa gggtggtttg ttctttcatt  30900
tgtaaaaatc agggtgacag tttactgcct tgtcaccaat cag                    30943
```

<210> SEQ ID NO 5
<211> LENGTH: 64700
<212> TYPE: DNA
<213> ORGANISM: Homo sapiens

<400> SEQUENCE: 5

```
gtgcctctag aggatcccca tgcacagatt agaaaggtga gtcttggccg ggcagggtgg     60
ctcgtgcctg tcatcccagc gctgtaggac gccgaggtgg gtggatcacc tgccaggagt    120
ttaagaccat cctggtcaac atggcgaaac ccctctctac taaaaataca gaaattagcc    180
agtcatgatg gcgggcgcct gtaatcccag ctatttgaga ggctgaggtg ggagaatcac    240
ttgaacccag gaggcggagg ttgcagtgag ctgagatcgc gcactgcact ccagcctggg    300
cgacagagtg attctgtctc aacaaaataa ataaataaac aaacaaacaa ataaataagg    360
gtgagtcttg ggctgcaggg tatggggcac caaaatgagg taccggtccc caggcacaga    420
ctcaggatgg ggaacctggg gtgagaaggg agggtgcaga ctcagagggc tgccgggaac    480
tgggctcctt ctccccgccc catcccctga cccaaagcct tttgctccag caactgggct    540
ccaggggagc ccaccagccg gagccagggc gaggactgcg tgatgatgcg gggctccggt    600
cgctggaacg acgccttctg cgaccgtaag ctgggcgcct gggtgtgcga ccggctggcc    660
acatgcacgc cgccagccag cgaaggttcc gcggagtcca tgggacctga ttcaagacca    720
gaccctgacg gccgcctgcc cacccccctct gcccctctcc actcttgagc atggatacag    780
ccaggcccag agcaagaccc tgaagacccc caaccacggc ctaaaagcct ctttgtggct    840
gaaaggtccc tgtgacattt tctgccaccc aaacggaggc agctgacaca tctcccgctc    900
ctctatggcc ctgccttccc aggagtacac cccaacagca ccctctccag atgggagtgc    960
ccccaacagc accctctcca gatgagagta caccccaaca gcaccctctc cagatgagag   1020
tacaccccaa cagcaccctc tccagatgag agtacacccc aacagcaccc tctccagatg   1080
cagccccatc tcctcagcac cccaggacct gagtatcccc agctcaggtg gtgagtcctc   1140
ctgtccagcc tgcatcaata aaatggggca gtgatggcct cccacatttg tccccttctt   1200
ggaggcctgg ctgggtctgg tctctgggtg tggcacatgg gagctgggaa ttccagagtc   1260
tgatgcctga gaccaccttt gaaagttggg acatcagatc tttggccggg tgtggtggcc   1320
catgcctgta attccagcac tttgggaagt caaggcaggc gaatcatctg aggtcaggag   1380
ttcaagacca gcctggccaa catggcaaaa ccccgtctct attaaaaata caaaaattca   1440
gccgggcacg gtggctcacg cctgtaatcc cagcactttg ggaggccaag gcaggcggat   1500
```

-continued

```
cacaaggtca ggagatcgag accatcctgg ctaacacggt gaaactccgt ctctactaaa   1560
aatacaaaaa attagccggg cgtggcggcg tgtgcctgta gtcccagctg ctggggaggc   1620
tgaggcagga gaatggcgtg aacccgggag gtggagcttg cagtgagccg agattgcgcc   1680
actgcactcc agcctgggcg acagagcgag actccatctc aaaaaaaaaa aaaaaacaaa   1740
aacacaaaaa ttcgctgggc gtggtggtgc acacccgtaa tcctagctac tcaggaggct   1800
gaggcaggag aagtgcttga acctgggagg tggaggttgc aatgatctga gatcacgcca   1860
ctgtgacaga gcgagacccc aactaaataa atttaaaaag aaagaaagaa aattgggagc   1920
aagcagatgt ggtggctcat gcctgtaatc ccagcacttt gggaggctga attgagccga   1980
tcacttgaga ccaggagttc gagaccagcc tggccaacat agtgaaaccc cgtctctact   2040
aaaaaaaaaa tacaaaaatt agccaggcac ggtggcatgt gcctataatc ccagctactc   2100
gggaggctga ggcaggagaa tcacttgaac ctgggaggca gaggttgcag tgagccagga   2160
tcgtgctact gcactccagc ctgggtaaca gagtgagatt gcatgtcaaa aaaaaaaaaa   2220
agaagaaaaa agaaacaaat tgaggagcaa ctgaagtaga attcgatctc ccgtttttat   2280
tttttcctgc tctatgacac ggagaatgtg caggacatga agcctctgag gtccaatggc   2340
cccttggaat actgtagggg aaggcggtgg atcaccctga ggccgggagg gcgtgagttg   2400
actcatggaa gtacccagag cagggcttag tacacagaag gcactcagta agtgctggct   2460
ggctggacag gctgatgggg agtgggcccg gtcaaccgga ggccatttcg ggtctggagg   2520
tgttaaccct actcagggtc tgggaggctg aggtggcacc agcctcacgc tcggccaagg   2580
tcgacccatg ccggaggcca cgggagggag gccaggagca cagggtcccc tctccacact   2640
cctctaccag tggctcaggc caacactggg gtcattgcac ctcttccctt tcccctgaca   2700
acacctccag gtccaagacc ataagaaatg ccagtgggct ctgctgtcaa acggcgctca   2760
caatcactca ctgctcaccc cttctgccac tgcctcgact ggagcagtca cctccgcccg   2820
gggctctctc ttcactgccc cctttccaga agtttcctcc agctcagata aaaggccaaa   2880
gccagctgcg cacagtggct catgcctgtc atcccagcgc tttgggaggc tgaggtggga   2940
ggactgcttg agttcaggag tttgaggcca gcctgggcaa catagtgagg ccccatctct   3000
acaaaaaata caaaaactag aggtgtagtg atgggcaact tggtcccagc tgcttgggag   3060
gccgaggtgg gaggattgtg cccctgctct cagcctgggc gacagtgaga acctgtctca   3120
aaaaaaaaga agaagaaaag agaaaaagcc agccaggtgc ggtggctcac gcctgtaatc   3180
ctagcacttt gggaggccaa ggcgggcaga tcacttgagg tcaggagttc cagaccagcc   3240
tggccaacat ggtgaaaccc cgtctccact aaaaatacaa aaattagctg ggtgtggtgg   3300
cggatgccta tagtcccaac tattcaggag gctgaagcag gagaattgct tgaacccagg   3360
aggctgagat ctgagatcgc accactgcac tccagcctgg gcgacagagt gagactccat   3420
ctctaaataa taataataat aataattaat ctgtgtgacc atgggcacat gacttctttt   3480
ggaacctgcc tgtgaaatga gctgatgctg cttgcccagc tcaccaaggg ctggtgcctg   3540
gctcctcctc ctcctcttcc tctcacccac ccacctggag ggtccagggg aagaccttcc   3600
ttgcagccca gagcaccgta agttagagct gctgtgatca gaagctgccg aaccacaggc   3660
tcttctttct cttcatcctc ccttgcccca accccgggcc cagcctcata accctacagc   3720
ttgttcaaac gttttccctt ctcctcaagc cccctaactc accctcggtg gccggtgggg   3780
atggggcgtg ggaacagacc ctgggccctg cactcccagc ttacaaattc ccgcagcccc   3840
tcttcctccc tcccgatttc tctgacatcc ctcacagccc cgcctctgga cagaagaatg   3900
```

-continued gcccctgccc tggccggccc tggaagcccc tctcgccagg gtctcagagg acctgcctgg 3960
ggctgcttag cccaaagcgt cctgcatttt gctctgaaat ccagcttctc agacaccatg 4020
ttcccctccc tccgtccccc atccaggact gtggtttctg tgtctgtgca gacgcccaga 4080
cctccctcca gaactccaga ccccaaaccc caagacctgt gcatctgctg gccccctaga 4140
cgcctccccc tcattccaga ttcaggctat catcctgccc aagccctctc ccggcgcctc 4200
cctccacctc caacagccaa cagctattcc aggatcagcc ctggggctat gtgtggtggt 4260
tgctcaatgg tttcattcat cctagagacg ccaccttctc cccagtgtgc tgaagcccac 4320
cctgctcaat gcctcttgct aggatggctg agactgccct gaccaagccc tcagccctgg 4380
tccaccaggc agtccaacag agcatcctaa acaaatctag aggtgacacc gacccctttg 4440
gcccttctca taaccagtga ggggagccca gctgacagtc cctgcagttc cttttctgaa 4500
cagacctgtc tgttcacatt ctgggggcg gtggaaagga agcagggaag attggatcat 4560
ggttccccca aaaaatctgg aagaactttc cttgggggag aggaggagtt atcaggaacc 4620
aagtgtggtg aacaaaaagg gaaaggaaaa ttgcctgagg tgtaatacat tacttttttt 4680
ttctttttta agacagggtc tcactctgtt gctcaggctg gagtgccagt ggtgtgatct 4740
tggctcactt caacctccgc ctcccaggtt taagtgatcc tcctgcctta gcctcccaag 4800
tagctgggat tacaggtgcc tgccaccacg cccagctaat ttttgtattt ttagtaaaga 4860
tgggttttgc catgttgacc aggttggtct caaacttccg gcctcaagtg atctgcccac 4920
ctcggcctct caaagtgctg ggattacaga cataagtcgc cacgcctggc cttatttcaa 4980
attcttttag acaaggtctc actatgttgc ccaggctgga caccaacccc tggcctcaag 5040
cgatccttct gcctcggcct cctgaatagc tgggactcca ggtgtgcacc actgcacccc 5100
acttatttta aaattttttt aacaagggaa atgtgtttgt atcatcctgg actttaaaat 5160
taactttaaa gtattgacca gactggccaa cacagtgaaa cctcatctct actaaaaata 5220
caaaaaatta ggtagctggg actacaggaa tgcacctcca tgcccagcta atttttgtat 5280
ttttagtaga gacagggttt caccatattg gccaggctgg ctcgaactcc tgacctcgtg 5340
atccgcctgc ctcggcctcc caaagtgctg ggattatagg cgtgagccac cgcgcctgac 5400
ctttttgttt tttagatgga gtttcgctct tgttgcccag gctggagtgc aatggtgcaa 5460
tctcggctca ctgcaacctc cacctcccgg gttggagcga ttctcctgcc tcagcctccc 5520
aagtagctgg gattacaggc atgtgccacc acacccggct aatgttttct atttttagta 5580
gagacggggt tttgccatgt tagccaggct ggtctcgaac tcctgacttc aggtgatcca 5640
cctgcctcag cctcccaaag tgctgggatt acaggcgtga gccaccgcac gtggcccctc 5700
ctggtgattc tgataccta aagcctgcat ctcaatctaa ggtccccagg aatcccctgg 5760
gggcctcgct aaaatgcacc ctcagattca gcagctctgg ggtgggcctg agactgcatt 5820
atggaccaac tcccagttga tgctgctact gctgatctac agaacacact ttgatttggc 5880
tcacgcctgt aaccccagca cttacggagg ccaaggtgga aggattgctt gaggccaaga 5940
gtttgagacc agcctgggca acctaataag agcccccatc tctacaaaaa ttttttaaaa 6000
attagctggg catggctggg cgccatggct cacgcctgta atcccagcac tttgggaagc 6060
cgaggtgggc agatcacgag gtgaggagat cgagaccatc ctggctaaca tggtgaaacc 6120
ccgtctctac taaaaatacg aaaaattagc caggtgtggt ggtgggcacc tgtagttcca 6180
gctactcggg aggctggggc aggagaatga catgaacccg ggaggcggag cttgcagtga 6240
gccgaagccg agatgctgcc actgcactcc agcctgggcg acagaacaaa accctgtctc 6300

-continued

```
tgaaaaatat aataaatgag ggaagaaggc aaacaatctc cctctgcctg ttttctaggc   6360
acacggtgac acccactcct ttacatgttg tctgtggttg cattcagtac atcagcggag   6420
taatggggca agagcacatg gcggcacagc agtggctcac gcctgtaatc ccagcacttt   6480
gggaggctga agtgggcgga tcacctgaga tgaggagttc gagaccagcc tgaccaacat   6540
ggtgaaaccc catctctact aaaaatacaa aaattagccg ggtgtggtgg gaggcacctg   6600
taatcccagc tacttgggaa gctgaggcag gagaatcacg tgaacccaag gtggaggttt   6660
gcagtgaggt gagatggtgc cactgcactc cagcctgggc gacagagcaa gactctatct   6720
caacaaataa aaaaaataat aataaagacc acatggcata aaatattgcc catctggcac   6780
tttgcgcagt ttgcccaccc ccagtctaaa ggcgtctgtc tcagcctgat gcgtctccca   6840
ggaccccatg cccccctccag cctgcagaca gcctccaacc gtgattccag aacctgccag   6900
catttcccac caactccttt tgccgggttt atttctcccc accactcctg gtctcactca   6960
accccccaac cctatggcca gacccgcccc cactctactg taaacacatt cggacctggc   7020
ctccctcccc agcctggggc agggctgtgg ctcaaggtac tgagtggatc taaggccgcc   7080
acacaagaca caagacacac gtggggaggg gctctctgta tcctttatct ccggcagggt   7140
cagcggccct ccagggcccg gtctcgagcg atgactgcct cctcgaactt gatcatgagc   7200
gtggtgccct tgtgccagtg cgccgtgacc ttggcaggga agccgctgtg tgtgagcacc   7260
gcctccacga tgcccgccgt gaagctggcg cagttgagcg tgctgttctc cttgggcacg   7320
gagatgtagg tgttgatgag cggctcgcgc tcgatgatgt agaaggtgcg cgcgtcatcg   7380
ttggcctgct ccagcttgtc cgcctccttg ccgaagagcg ccttccacac ggcgcccttg   7440
acgaagagca acgcgcctag caccttggtc tcacgccggg caccctttc gcgcgccacc   7500
agcgcatcca gcacgcgcgc gcccacctgg cggcccagcg cggccaggcg cgactgcagc   7560
tcggccacgg agaagacgcg gctctggcag tgctgtacca gctcggagaa cagcagtgcg   7620
aaggcgctca ggctcacctc ggtgcgcggc cgcgccagcg cgcgctccag cagcgccgac   7680
ttcccgcgcg tgaagcgcgc ctccatgccg ccgccaccct gcggggagac caggaagtgc   7740
aggtgtcagg ggcaatggga aggggagcag gccgggagga aaggagggag aaccgcgagg   7800
ggccctggga caccctcgac ccatgccact gttgtgtgct ccagtgccga cttcccactt   7860
gcaaagagat gcgcgtaaaa cacgcctcga ttacacgtaa ccagataaat caagggaggg   7920
gggagtctta taccctcggc aggcagcggg ctagcgggag tggggacaag gtgggaggag   7980
agacacgagg gggaacagaa gaggaggccg aaaccaccca accctcgggc atgcagacgg   8040
ttcaattgcg aaagcgcctt cctgcccgct ccgccaccta caggagtaac tagaaaacta   8100
gtgtatgggg ggaggggcgt cagatctagg gcagggaggt gacaaagatg aggcaccacg   8160
aggggatatg ggcagtcgct cctgccccgc cctgcgctcc agcacagacg accctcggga   8220
actttcctgc cggccccctg cggaaagcca gagtaaaggg ggtggagggt gggagtgggg   8280
taggagcgtg tcaagaccaa aagccaggag ggttgggggc tttaacaggg gggatccgtg   8340
gggccaggca ggaggggcgg gtaaccccca accccaagcc ctcaggcagg cagctccgat   8400
gtgtcacgca ggaacccttc gtcctttgag acgcggatgg gcctgggttc tgaaggctgg   8460
gaggaggggc ccagaggtgt tgggagcctc ccaccccc gt gctctccaga aaggaagctg   8520
gatgctgagc aactgtggtc ctcccatcag ctgtcggtgc ggggagaggg agatggggta   8580
gggggctcct gaagagaaat ggggtgggga gcgggcgccg agacgggatc ggaggggcag   8640
ctgagaaccc gcccccacca tgcatgggga ggtgtgtgga tgctaagccg accccaacga   8700
```

-continued

```
ggtctgcgtg ggaggtggga gaaccagcgg ggaggggtgt cccaggggct ccgggccgcc   8760

cccgccccag catgcagatc cgtccgtggc gagggccctg ggcgcgcgag atgggagagg   8820

gatcgttaag accccaccac cgggctgcga tgggggctga agtgagctga actgccgtag   8880

ggtcagggcc ccgcgaccct cgccccgtac ctctacactg gggagaaacc caccctcctc   8940

gcagcctcct gaggggggcc gaagcgagcg ggctcgggat cgcggacgcc gagaccccag   9000

cccgggaccc acacgcccgc ggggaagggg ccggggagcg gacgaggccc ggcgcgggca   9060

ggggggtggg tagggtctca ccaggaaccg cagcagtctg ctcggccgag ctgctttacg   9120

gcgccgtaaa aggcgctgcg tgcgcaggcg ctcgacgggc caggcgtgtg ggcggggcgc   9180

gcgcagcggt gcctgagagc ggccgcaggg gggcgcgcga gtccgcggag ccggacccag   9240

ggacgtggcc cacggccgtg atggctgctc cgcgcgtggc cagggtctcg ctggctctgg   9300

gtggcccacg ctggagggga cgcttgcagg cctagtcacc tgctcagggc gcacgtatga   9360

caatgggcca atgtataccc ttgcacatgg acacacctgt tggcttttcc aggcactcct   9420

atgtccttgg ggatgggttc aattgtctca agtgcatcca tgtggcccgc ggtggctccc   9480

gcctgtaacc ccagcatttt cggaggcgga ggtgggagaa tcacttgagg ccaggagttt   9540

gagaccagcc tggacaacat agctagactc ccacttcttt aaaaaaaatt agccaggtgt   9600

ggtggtgtga acctgtaatc ccatctactc gggaggcgga ggcaagagga tcgcctgagc   9660

ccaggaggtc gaggctgcaa tgagtcatga tcgtaccact gccctccagc ctgggtgata   9720

gagcgagacc ctgtctcaaa aaaacaaaaa caaacaacaa caacaacaaa tcaagtgcat   9780

gcatgagcgg tggacatagt accttagggt catgtacact catggataca tgctcaatgg   9840

catagataca ctcacgggca caattacaca cgtgggtaca cgcttagggc ttgtatatat   9900

ccgtggtccc aggtacactc agggagatgt tgtatgctca ggggcaccca ctctgggaca   9960

cagggaagac acagggaatg agttactcat tcacagatgc acaggtactc acgcagggca  10020

ctcagtctcg cccaccctgg tgccccgggg tcattgtcac gtgcagactc tccctctccc  10080

caggtcccaa aacccctccc cttgccccag taacaggtcc catagcgacg ctgttttccc  10140

ttgactttat ttatcttcat aagtcacaaa atgtgagtgc agagataaat gtctgtgtgc  10200

atgtgccctg agcacacagg gtggcataac tcggcacact cataatgaca cagccgttca  10260

cccagccaca gatagtgaca gggcacacat ggcgacaccc acatgtacgg agataaatct  10320

cccccaccat gacatgggta gacagaaaac acgccgcagt atactctagt atgtttacac  10380

aaacagggag acaggcccgt gcaatgcatg tcaccaacac ccacactcag agtgacatct  10440

gctggaggtg ctcagacaca gccacccacc gtgacatgcc gagactcaca tatgtcacat  10500

gacacaggca tgcatgccac attcactgtg actctcagtc ctattcattc atcacctttc  10560

tgggagatac actgaaatgt ccaccctttg caaaatgcac acacacgcgc acgcacacac  10620

gcacatacac gaacacacgc gcacacacgc acacacacgc acgcaggtgt acacacacac  10680

gagcaactcc gagacactca ttcaccatga ctcgaggttt ttctatacgt gggacgaggg  10740

gcaggttcac actaggctgg gggggggggg tcatttcccg tcttcgttgg caggtgcagc  10800

cccatcttcc aagttgtggc tttggctgcc acaatgtcct ctcatttatt gaggtgagga  10860

ctctggggat ggggagagac ccacagtgag gcagatcccg cccctgggag aggagctggg  10920

gctaaatctg aagccccacc caccctcctc cacctcctgt cggggcgcca acttacgtgg  10980

cattttctgc agcacctcca agatttctg tacctttgtg tcaatgtttt ttatgcctag  11040

ggggcgggga gggttgggtg ggaacagata agtcaagctg cggtggagcc tcaaacaaag  11100
```

-continued

```
cccccacctt ccttggaagc acccccccctg ccccacaccc accctggggt acagcagagc  11160
ccatggattt ggggttccca ggagcctttc aatacccaca gagcaaccca gatggtaaca  11220
cccatcgccc ctccacaact tgagctttgg gagggtagga ccccggcttt ctcctcccct  11280
gaatcccctg cccccagctc agctccgggc attggtgaca aataaccccc atagaaggcg  11340
agactacaca ggcacctgct aatgtcgtct ctaatctatc aatcttgctc ctgaccatgg  11400
tgatgctctg ctgaacggaa tcccagcctc tcttctgtct ctcttcgcat gcttgtacgg  11460
agtttgagac tgagggcatg aaacaggggt gtctgtgcat ccatccctct ccagaccccc  11520
accatgaccc cacgggtctc cctcagaccc tccgctcacc attccaaagc tccctttttaa  11580
agcccagcag ctccttggac atctcagcat ctgttcagga ggggcaggaa aatccttgaa  11640
gcacccaggg agagagagag agaaggacaa gggagaaagt ctaggccccc cagcaccctc  11700
ctcccaagaa gtactcactc ttcaccatga tgaaggctga caggatgatg cagaggacaa  11760
aggccagggc caggaggatg tacaggctca ggatggctct gtacaaccag caggggacct  11820
gggtggagtc tgagggcggc ctgcactggg ctgggactgg agcaaagagg cagcaaagtg  11880
accttgaggg gccagcacca ccactcaaac catcctcact gtctctaaca ccatggacac  11940
ctcgctcctc tcaaaaccat cagcagctgt ggtcatgcag cttgtcatca tcgtcaacaa  12000
cactgccacc accagccacc ctcagcgatc taacaccgtc accatcacag acccccctctc  12060
cagcattccc caacattgtc atcatcaaca gacctcatta gcacgtcaac agctgtcacc  12120
tcttccttcc ccatcgcttc ctcccttcca cgcagccccg gggccctgc agttgcccgc  12180
ccacctgccc cttcccaagg tgatgggatg tgagcaggtg ggtgtctgct caccttggct  12240
cgtgggtcgt gaatgaccac cctttgcatg gtcctgattt ttgaaggcca aggtgatatt  12300
ctcatagtct gggtcatggg cacctgggag gggttggaga tctgctcaga gctctgtggt  12360
gtggagagtg gatccgggat cttgttttac ccaacccttt gcactcaata aattgtaggg  12420
ggtgaaagat aaggagtgag aagctaaaat ctgcttttttg gttaagtgga gcgggtgtgt  12480
gagagtttga gtgatcacac cacacacaca tccacacaca catccacaca tcttggaggg  12540
gaaggagccc ccggccccca cctttgaccc cttacctctc ccatctgaac tctccttctt  12600
tttttatttt tattttttac agacagagtc tccctatgtt gcccaggcca gtctccacct  12660
ccagggctca cgcaatcctc ccgcctcagc ctcccaaagt gctaggatta cagacatgag  12720
caaaagcccc cggcccccca atctctcctt cttaacccct cccttccacc tcgagttccc  12780
taaccttgat tcttggctga gaccccctgt ttcttgtccc tgaaggctgg tgcttgcatc  12840
ttgacttcct ggtgcttgta gatttcctcc acttccatgg tccccagccc gcaaatttgt  12900
ccatacacgt ccccgcccac cggaaggtgt gggcagatga ggaaatctgg aggtgggggg  12960
aagaaagagg gggagcagcc tcctcttttc agggatccac gactctcgca ccctggggca  13020
ccctcattcc tgccccgatc aagaggctct tgggagccaa gaggtctcag gaaggaccaa  13080
gaagaaaaac ctctagaccg ggagatggaa ttcgacactc ggaaatgtta caggaagctg  13140
tggtctctgt gtgtgtctgt gtctacctgg atggacctca ccctcctacc tcctctccat  13200
ttcaaaagag aagctgtgac acctcagtgt cccaactttt cgcgtaagag caaccaggct  13260
tggagacagg acccctgggt ccccccacac cttcctccct ccagcctcag ctccacccct  13320
cagctccacc cccaagaagt tcttctactt ctacaagtcc ccgtggagga aaagcacaga  13380
tgtgaggcaa cgggaactaa ccactggaac gccacaccca catctgggac tgaggacaga  13440
cccacatcct tccctccctc cccaaatccc ctgcttttat acaaccctgg aggaggctgg  13500
```

gtgcggtggc tcacgcctgt aatcccagca ctctgggagg ctgaggtggg tggatcatct 13560
gaggtcagga gtttgaaacc agcctggcta acatggtgaa accccgtctc tactaaaaat 13620
acaaaaatta gctgggcgtg gtggcgagcg cctgtaatcc tagctactca ggaggctgag 13680
gcaggagaat cgcttaaacc tgggaggcgg aggctgcagt gagcggagat cacaccattg 13740
cactccagaa tgggtgacaa gagggaaact ctgtctcaaa aaagaaccct ggaggaacag 13800
tttcctctgc acctggaaac tccaggtttc tcattctcat ccatccatct gcttatctac 13860
ccagatactc tctctcacac atgtacacac acaggtctgc acacggacac acatcacaaa 13920
ctcatttgca tactatttgc attgtgacac tcagaaaaat agacacaagc atgcgttcac 13980
atgcccgcac tctgtctaga aggtgtctta gttcactttg tgtttatctg atcttgaaaa 14040
ctggggttac aaaaggcaca aagtagctgg gtatggtggc tcgctctgta gtcccagcta 14100
cccaggaggc tgaggtagga ggatcatttg aggccaggag tttgagacca gcgtgagcaa 14160
catagcaaga ccctgtctct ttaaatgttt tttaataatt ttttttgag acagggtttc 14220 actctgttgc ccaggccggg gtgcagcagc gtgatcatgg ctcactgcag ctttgacctc 14280
cctggctcaa gtaatccttc gtcctcggct tcccgagtag ctgaaattac aggtgggcac 14340
gacttcacct ggctaatttt tctccttttt tgagatggag ttttgtgctt gtcacccagg 14400
ctggagtgca atgacgctat ctcagctcac tgcaacctcc gcatcccagg ttcaagtcat 14460
tctcctgcct cagcctccca agtagctggg attacaggca tgcaccacca cccccggcta 14520
attttgtatt tttagtagag acggggtttc cccatgttgg tcaggctggt ctcgaactcc 14580
tgacttcacg tgatctaccc gccttggcct cccaaagtgc tgggattaca agcatcagcc 14640
accgtggccc agtctaattt ttcttatttt ttgtagagat gagggtctca atatgccgtc 14700
caggctggtc ttgatctcct gggttcaact gatcctccag ccttggtctc ccaaagtgct 14760
gggattacag gcatacattt ttatttttat ttttttctgg ccaggtgtgg tggctcacgc 14820
ctgtaatcac agcactttgg gagtctgagg cgggcggatc acctgaggtc aggagttaga 14880
gacaccagcc tgaccaatat gataaaaccc tgtctctact aaaaatgcaa aaattaactg 14940
ggcgtggtgg caggcgcctg taatctcagc cactcgggag gctgagacag gagaatcact 15000
tgaacccggg aggtggaggt tgcagtgagc cgagatcgcg ccattgcact ccagcctggg 15060
caacaagagc aaaactccgt caaaaaaaaa aaaaaaaaaa gaaaaaagaa gaaagaagaa 15120
agaaggaagg aaggaagaag aaaagaagaa aaaacaagta taagactgtc ttatgtgcag 15180
aaagtgatga tgttttggtt aaaaatatgt ggttaaattt cagacaactt gaatgttgag 15240
aaatgagcgt cgagatctgg tgaggataaa gttctgtttc ctaaaatatt gccaaatcct 15300
gtgtctccaa gaaagatcaa tttgataatg acttcatgcc agctgctcca tttggtctta 15360
gaaagaagtc agttactgag ctataggacc gccttctaat ggagcagacg gaccaattgg 15420
atgtgggctc tgccttgatg gacaggcaca gggggtggag ccacagcgtt gcacatttcc 15480
cgggcttggg tggggctgag acgcggctcc aggctctgga cttcctttga gaaaaaggtc 15540
acgctaaacc agaggcccac aagcaatcat gtcatgtggg aaacatctgc aaagctgcct 15600
gaccagcacc cgtccctttc atagggtaac attctcaatt ttcttttaag aaagaaaatg 15660
tgtgctagat ccagcaaacc ataagctagg gattggttta cagtggacaa atgatccaga 15720
cccagccaac cagagtctaa gattgggcag agaggcgggc atttgagcaa gatccagcca 15780
atgaaacgct ggtctgggat ttttattggt ttaaccacgg gggaaaaagc attctctttt 15840
ttttccagcc ctcactaggg ctgccacaat gggaggatgt aatgggagct gtgacaggga 15900

-continued

```
agaatttact tgagagcaaa ggcagtgctg agaaaatcag acccgagagg aagtctgggt  15960
cctggagaca tcatttgaga ccctggttcc aagccatacc tgaacctgtt gttctaaccc  16020
tgggcttgtc agttacacaa acaagaaact tccttttagt tttgcccaag ctagtttgaa  16080
gtggggtctg ttgtacttgc aagcagaaga atcttgcctt ggctggtctc tgtggcccac  16140
gcctgtaatc ccagcacttt ggaaggccga ggcaggtgaa tcacttaagg tcaggaattt  16200
gagaccagcc tggccaaaat ggcgaaatcc ccgtgtctac taaaaataca aaaattagcc  16260
aggagtggtg gtgggcgcct gcaatcccaa ctactcagga ggctgaagca ggagaatcac  16320
ttgaacctgg aggtggaggt tgcagtgagc tgagatcgtg ccactgcact ccagcctgga  16380
caacagagtg agactccatc tcaaaaagga agaagaagaa ggaggaggag gagaaggatg  16440
aggaggagga aggagggagt gaggagggag gagggaggag gatatcttgc ctaccacagg  16500
ggatctaggc attagctatt gaggaaattg aggctctaat agggggtttg cctgtccaca  16560
tcacctgggc agatatgacc tccaagtctg cactctgggg caggagaatg tctatgttgg  16620
aattgaggaa cctgaagaga gccctcttag gtttcagata caggactatt ggatgggggt  16680
ggagacaaat agttctgggg acaatggagc atccccgccc ccaacacaca cacacagcag  16740
taaggggcag ggacacacac aaggcactag actcaccctc tctggccctg gccatgcttc  16800
taactcagtg gtcctgccct acccccatga ccactgtgga gtcaggagag agggtctggg  16860
aagggaatcc ctgggctgga gtctgggtgg ggtccctggc accagaagtg gttgtaatct  16920
ctgctcatgg ccaccagcat cagacagggg gctgggacca tcacaggggg tgggtggcag  16980
tgggaggaga gtccaaaaca tcctgcaaac cagaacctca ctctatcatc tgttgtccag  17040
gtgtgacatt tgagtctggg atccctttca agactaggtg ctaggaattc tgaagtctgt  17100
ggtgggaaat cagggactgg atggcaagac tcctgggtca ggcttcctgt agaactggac  17160
cccgaatcac ctgaatttgt gccccaggga gctgaggcgg gggatgctga ggcttttgcc  17220
cactagaaca ggggtcccca gccaccgggc attgggaacg gggcctcaca gcaggaggtg  17280
agtggtgggc gagcgagaga agcttcatct gtatttacag ccactcccca tcattcgcat  17340
taccacctga gctccacctc ctgtcagacc agcagcagca ttagattctc ataggagcaa  17400
gaatcccatc gtgaactgcg catttgaggg atgtagcttt ctcacttctt ataagaatca  17460
aatgcctggt aatctgtcgc tgtctcccat caccctcagc tgggaccatc tagttgcagg  17520
aacacaagct cagggctccc accgattcca cattatggtg agttgtagaa ttattttatt  17580
ctatattaca atgtcataat aataaaaata aagtgaataa taaatgtaat gcgcttgaat  17640
cacccagaaa ccatccccgc tcccccccta ccccatacac acaccaactg tcttccatga  17700
aaacagtctc tggtgccaaa aaggttgggg atcgctgcac tagggtatca gatacttatc  17760
caggtgcagt ggggactaga gtcagaaatg caagagtctg cctggagcat gtgtgtgttt  17820
gtgtcctgca tcatctctgc ccaccatagt caaatctgcg attctccgtg cattggccgg  17880
gggggtggtg cctttctgtg tccaagagtg tctaggggca catgggtgtg tctgtggatg  17940
tggtgtctcc atgtggccgt ggtaggtggg ttgtgtactc tgtgtgtgca cgtggctgtg  18000
tatagctgtg tgtgcatgtg cagtatgtgc acgtcggtgc tgtatctaag tgcacatgtg  18060
gctactgatc aacagacatt tactgaacgt ctactgtgtt ccatgctcta ttctaaaccc  18120
tgggggcgct gggtgcagtg gctcatgcct gtaatcccag cactttggaa ggccgaggtg  18180
ggtggatcac ctgaggtcag gagtttgaga ctagcctggc caacatggtg aaacccgctc  18240
tctactaaaa atacaaatta gctgggcatg gtggtgggca cctgtaatct cagctacttg  18300
```

agaggctaag gcaggaatat cacttgaacc caggaggcag aggttgcagt gagccgagat 18360
tgtgccactg cactccagcc tgggcgccag agtaagacct tgtctcgaaa ataaaaatta 18420
aaaaataggc caggcgcggt ggctcatgca tgtaatccca gcactttggg aggctgaggc 18480
gggtgaatcg cttgaggcca ggagctcaag accaacctag ccaacatggt gaaactcctt 18540
ctctactaaa aatacaaaaa ttagccaggt atggtggcga gcgcctgtag tcccagctac 18600
gtgggaggct gaggcaggag aatcgcttga acccaggagg cagaggttgc ggtgagccga 18660
gattgcacca ctgcactcca gcctgggcaa cagagcgaga ccctgtctca aaaaaaaaaa 18720
aagaaagaaa gaaagaaaag agaagagggg agaggagggg aggggagggg aggggagggg 18780
aggggagggg aagggaaggg aagaaacgaa accctggggg ggatctagga gcagacaagt 18840
cccctgctct gtgttttcat aatctagtat ccaggaaggg gtaagcaccc tgcgtgtatc 18900
tggttgtaac taactactca caactgcact tgcctgtgtg aaaacgtgag cttgtgatga 18960
tgcgtgacgt caggtaggcg tccctgactc tccgtaaccc aactttgcct gtgccttggg 19020
gattcctcct tgcaggtagg aagtgagggg tacaggttcc agctctgggc tgagacatga 19080
ttcagggttc caccctgacc tggggctcct ggagtcttgg ggccctggag ggtcccgtcc 19140
actgcccaga ctgacccagg tcctcgatga agcctcatta tgaggactgg gggaaaagga 19200
cccagccact tcctggggag gtcggagacc ccagggtgag cgtcaaggta gcctcaaaga 19260
tgagacgtca cctcttgaag gcagccatga gccttgggtg gggacgtcac tagaggaagt 19320
tcaggcccta ttttcggagg aagcagttgg agaccccata ggaggaaggg cgatggggca 19380
gtagaaagtc gcggtgtccc cgccccctcc agcagctacg cgccccactc tcttggagac 19440
gctagatcag tccctccggg cctactaaag aaaccacgca gggctcagat ccgctccatc 19500
atcatcatca tcatcatcat catcatctcc aggtttattt ccagctcccc cgcaacccct 19560
ccggacctgg agccgcctcc gcccgcgctg tgcacgcgct gcgcgcgacc tcagggctgc 19620
acacgacagc agcgcgctcc ggtccagtcc atgcccgcgc actggcagtg acatgtggtc 19680
tcggcgcgca catcccacga gccacaggcg gagccacaag tgcagccggt gacggcgaag 19740
cctgcagccc ggaacacagg agcgtggact ctgagctggg aggctgaggg tgggagcggg 19800
aggggggtgg ggagcgcgga ggggggttgg gggggcgggg gtggggacgg ggacggctgg 19860
aggctccaac cactgaatgg gcactggagg cagggagtga gggtggacac cagtgtccag 19920
atggtgggcg gagaaggctg ggagtcagga ccaagatcct aggggagtag aggctggaca 19980
cggggaacgt ggcggggagg gggcattccc aggggacttg gaacagaaat gggcgcctgg 20040
acaacagtct cctgcactca cctcgggggc aagtagccag gtccccccctg gaggtgacgc 20100
tctggcactc caggccaatg ctgcttattg ccctaaatac tggggggcag gaggaaagga 20160
gacaggggga gctgtgagac caaacggtcc ctcccccatc ctcccctagc cctgttggtt 20220
tggagctagg tccctgtggg cataggagct cactggcctc caggaccctg tcttgagttg 20280
ggtgttttgg agtaagggaa ggtttggagt gagagcgggg attgggtttg gagccgtgga 20340
taaggtgggg acagtcggag gggttgggag tggagttggg gttgaattta tgatctggtt 20400
ggatttgagg atgagatttg gtgagcgctg gggctgggtt ggagtcaggt ctgtgccagg 20460
gatcagtgag gtctctgaga cccttgggga gcttgcccaa gtggggggtc ctcacttagg 20520
gagccggcga cctcctggat cctctcattg atggcttctt ccatggagca cagggtcttg 20580
ctagacacca acagccccag gacagggagg aggaggagac agagagcttt catcctgcag 20640
gcgctgaaag agggaaccaa gagacccaca gctggatcag ccctgccctg tggggaagat 20700

-continued

```
ccggcccatg gagggagtag gatctgcccc tggacctgga cccctgtccc cccatgtggg  20760
ggacagggat ggaggctcag ccttgacccc agcctccccg ctggtgccat ggcaagcgca  20820
ggagcagctg tcacttaccc tctcggtggg ctcagctaac caaatccggc acacgaattc  20880
ctgcaccgca gctctttctt tgaggcctct tggggtgggg cttcctggct tggctaataa  20940
gtccctgggc ccccaaccct ccggtcccac atccggggcc aagaggaagc ccctgagcag  21000
acagtaaggg ctggaggagg aagggagcct tcccacttcc aacagggcct ccgtcttcat  21060
gtccagagac tggtcaggag gtggtgcccc agggataatg ccaggggctg tggtctgagg  21120
aacaggtaga caagcagagt tttgcatgca agggtggctg atgcaaacat gacaaaatta  21180
atgcctcttg ctaggcatgg tgcggacaag cacttgtagt cccagctact aaggaggctg  21240
acgtgagaga attgcttgag cccgggagtt cgaagctaca gtgacttatg atcacagcac  21300
tgcactccag tctgggcaac agagcaagac cacttctcta aaatagtaat aataattatg  21360
tctctgggtg agaatgacat accacattca tacccaaatg cccatgagca atagaactgg  21420
taaataaaat catggtttat ggccggtggc tcacgcctgt aatcccagca ctttgggagg  21480
ccaaggcggg cggatcactt gaggtcagga gcttgagacc aacctggcca acatgatgaa  21540
accctgtctc cattagacat acaaaaatta actgggcgtg gtggcgtgtg cctgtaatcc  21600
cagctacttg ggaggctgag gtgggagaat cacttgaacc cgggatgtgg aggttgcagt  21660
gcactgagat cgtgcccctg cactccatcc tggatgacta gcttgggcac catagcaaga  21720
ctccatctca aaaagaagaa agaaaaatca tggtttattc catcaatggc atcacctgca  21780
acagaagttg gaaagccatt gctcatgggc caagtccagc tcatgtttct tcttggacca  21840
cccatgagct tggaatggtt attacatttt tatttgttct ttgtttccag tacaacgggc  21900
cttttgtggt aaaatacata taacatacaa cttaccatta taacttactt ttttcttttt  21960
tgagacggaa tcttgctctg tcgcccaggc tggagtgcag tggcgcgatc tcggctcact  22020
acaagctccg cctcctgggt tcacgccatt ctcctgcttc agcctcccaa gtagctggga  22080
ctacaggcgc ctgccaccac gcccagctaa tttttttgtat ttttttttttt ttagtagaga  22140
tggagtttca ccgtgttagc caggatggtc tcgatcccct gaccttgtga tctgcccgcc  22200
ttggcctccc aaagtgctgg gattacaggc gtgaaccacc gtgcccggcc tttttttttt  22260
tttttttgag acggggtctt gctatgttgc ccaagctagt gtcagactcc tggcttcaag  22320
taatcctccc accttggact ccccagtagc tgaagctaca ggtatgcacc atcttgttcc  22380
attttaacca ttgcttttgt ttgtttcttt gtttcagagt ctcactcagt tgctcaggct  22440
ggagtacagt ggctcaatct tggctcactg caacctccac ctcctgggtt caagcaattc  22500
tcctgcctca gcctcccgag tagctgggat tacaggcgtg caccaccatg cccggctaat  22560
tttttgtatt tttagtagag atggggtttc accatgttgg ccaggctggt ctcaaattcc  22620
tgacctcaag tgatccaccc gcctcagcct cccaaagtgc cgggattaca ggtgtgagcc  22680
accatgccca gcctatttta accatttttc agagcacaat tctgtggcaa taagcacatt  22740
catgttgtta tgtagccacc actgccgtcc atctccagaa ctttctcctc tttccaaact  22800
gaaactctgt ccccatgaaa cactcactcc ctatccctct ccccagcccc tggcaccctc  22860
catcttgctt tctgcctcta tggatctgat gactctaggg acctcctagg agtggaatca  22920
cacagtgttt gtccttttgt atctgcttat ttcactgagc ataatatccc caaggttcat  22980
ccctgctgta gcctgagtca gaactgtttt cctttccatg gctgtatcac attcccttgt  23040
gtggatgaac cacgttgtgt ttattccttc atccatcgat ggacacttgg gttgcttcca  23100
```

gcttttgttt tgtttttttg tttgtttgtt tgtttttgtt agttcacgtc ttttgtgggt 23160
tttctttctt ttttgagatg gagtctcact ctgttgccct ggctggagtg cagtggcacg 23220
atctcggctc actgcaagct ccgcctcccg ggttcactcc attctcctgc ctcagcctcc 23280
cgagtagctg ggactatagg cgcccgccac catgcccagc taattttttt gtatttttag 23340
tagagacggg gtttcaccat gttagccagg atggtctcga tctcctgacc ttgtgatccg 23400
cccgtctcgg cctcccaaag tgctgggatt acaggtgtaa gccactgcgc ctggccgtct 23460
tttgttaatt catacagtta tttgtcttct ggtttgttga agcagtaagt cagacaacat 23520
ttgccacaat aatgtctgtc aaagtggctt gccataaaca ctgcagcacc acattcatca 23580
gaagggcaac ctcgacgaag gtgactaatt ttgccattct catccacctt ataatatttc 23640
aggacagcca gcttcacctt ctttctcttg tgcttattcg tcttgcaggt aagacttctt 23700
cttctggccg ggctcagtgg ctcaggcctg taatcccagc actttgggag gccgaggcag 23760
gtggatcacg aggtcaggag ttcaagacca gcctggccaa catggtgaaa tcctgtctct 23820
actaaaaata caaaaattag ctgggcgtgg tggcacgtgc ctgtaatccc agctactcgg 23880
gaggctgagg caggagaatt gcttgaactg ggacccggga ggcagaggtt gcagtgagcc 23940
gagattgcac cactgcactc cagcctgagc tacagagcga gactccatct caaaaaaaat 24000
aaaaaaaaga cttcttcctt tccttagcac caccacgaat tctcaataca agatgaagag 24060
gagactcctt ttgaatgttg tagtcagaca gagtacgccc atcttccagt gcttgtcttt 24120
gctgatcagg aggaattctt tctttaccct ggatcttggc ctttacattt tctaccatat 24180
ctgagggttc agcctcgagg gtggtggtct tccctgtaag ggttttcagg aaaatctaca 24240
ttttggtggc ggctccacca cagatggcgg atctaaaagg tttttgtttt ttgttttttt 24300
gagacagagt ttcgctcttg tcacccaggc tggagtgcaa gtggcacgat cttggctcac 24360
tgcaacctct gactcctggg tttaagtgat tatcctgcct cggcctccga gtagccagga 24420
ttacaggcat gtgccaccac cacacctggc taattttttt ttcttttgta tttttagtag 24480
agatggggtt ttgccatgtt ggccaggctg gtctcaaact cctgatctgg agtgatccgc 24540
ctgcctcggc ctcccaaagt cctgggatta caggtgtgag ccactgtgcc tggcctgctt 24600
ctgccttttg gctattgtga ataatgctgc tctgaacata gatgtgcaaa tatctgtttg 24660
cagctcctgc tttcaattct tctgggcgta tgtccaggag tagtgctgcc tgatcatatg 24720
gtaattctat gtttaacttt ttgaggcact gccaattttc acatttttaa accataggga 24780
aaaaaaagtt gttttttttt taaaaaagac acagtctggc tctgttttcc acgctggagt 24840
gcaatggtgc aatcatagct cactgcagcc tcaaactcct gggctcaagc aatccccccc 24900
tcatcagcct cttgagtagg tgggactacg gcatgtgtca ccacacctaa ctaatttttt 24960
taattttttt gtagaggtgg ggtctcactc tattgcccag gctggtctca aactcctggc 25020
ctcaaaagat cctgccacct tagcttccca aagcactgag attacaggca tgagccactg 25080
tgcctagcca aaaaatattt gtaatgttta gtgaaaatag aaatcatata aaattcaaat 25140
tcatataatt ttcataaaaa gtccataaag aaaattttct taaaacattg tcagctgggt 25200
gcggtggctc atgcctgtaa tcacagcact ttgggaggct aaggcgggtg gatcacctga 25260
ggtcaggagt tcaagaccag cctggccaat gtggtgaaac cccatcacta cttacaatac 25320
aaaattagcc gggtgtggtg gcacgcgact gtaatcccag ctacttgaga ggccgaggca 25380
ggagaattgc ttgaacccgg gaggtggagg ttgcagtgag tcaagatggt gcccttgcac 25440
tccagcctgg gcaacaagag cgaaactctg tctcaaaaaa aaaaaaaatt gccaagctca 25500
gtggcaggca cctgtcatcc tagctacttg agagaccaaa gcaggaggat tgtttgagcc 25560
caggagtttg agggcagcct gagcaacata gtgagatcct gtccctacaa acacacacac 25620
acagtttgct accccctttt ttttgagagg gagactcgct cttgtcaccc aggctggagt 25680
gcagtggcac gaccttggct caccgcaacc tctgcctccc gggttaaagc gattctcctg 25740
cctcagcctc ccgagtagct gggattatag gcaggtgcgc caccatgtcc ggctaatttt 25800
tgtattttta gtagagatgg gatttcgcca tgttagccag gctggcttcg atctcctgat 25860
ctcaagtgat ccgcccgcct tggcctccca gagtgctgag actataggca tgagccactg 25920
cacctggccc cattttttaa tatatcatca gtgactgcta tcacatgtcc atggcagagc 25980
tcagcagctg tagagtggtt ggacagtagg gcccccaaag ctgagaatgt ttactatctg 26040
actcgttaca gaaaacattt ttttgtaccc ctggtatgtg gtgatgagtg agaatgagac 26100
aactgtccat ggattacagc tacacccaac catgtggctg attctcacga acatatgtta 26160
gcatagaagc cagaccccaa aaagaacata ccatacaaat ccatttatta aaaaaaaagg 26220
gggccgggcg cggtggctcc tgcctgtaat cccagcactt tgggaggcca aggcaggcgg 26280
atcacaaggt caggagatca agaccatcct ggctaacacg gtgaaacccc atctctacta 26340
aaaatccaaa aaaattagcc gggcgtggtg gcaggcacct gcagtcccag ctcctcggga 26400
ggctgaggca ggagaacggt gtgaacccgg gaggcggagc ttgcagtgag ccgagatggc 26460
gccactgcac tccagcctgg gcgacagagc aagactccgt ctcaaaaaaa aaaaaaaata 26520
cctaaaaata caaaaattag ccaggtgtag cggcaggtgc ctgtaatccc agctactcgg 26580
gatgctgagg gaggagaatc gcttgaacca agaggtggag gttgcagtga gctgaaatca 26640
tgctactgca ctccagcctg ggcaacagag agagactccg tctcacaata atgataataa 26700
taataaatga aatacaaaca aaactaattt atgctgtcgg aaatgacgat ggaagagtcc 26760
tggggaatca gagatagtgg tgataaaagc ataccaggaa ggcccctagt gagggggga 26820 ttttgtaaaa gttttcagct gtaactctca tttgcacaat tttctctatg tatttatatt 26880
tcaatcaaca tgatgcatgt gtattaaagc cctgtgtaaa tgcaacggtg cacacaggtt 26940
caaagcgcag gcaatattta ttgagcaact attatgttcc atatgctgtg ttaaacacca 27000
tgcatacact aagaagcaga gggatgctgc ccttgcccgg gacgagttgg cccttgtcag 27060
tcagggaaag gcagacacca acagaacagc aataaaaagg ccgggcaatg ggccaggcgc 27120
ggtggctcat gcttgtaatc ccagcctttt gggaggccga ggcgggtgga tcacctgagg 27180
tcgggagttc gagaccagcg tgaccaacat ggagaaaccc cttttctact aaaaacacaa 27240
aattagccag gcgtggtggc acaccaggtg ggtagctgta atcctagtta ctcgggaggc 27300
tgaggcagga gaattgcttg aacccgggag gcggaggttg tggtgagcca aggttgtgcc 27360
attgctttcc agcctgggca acaaaaagca aaactccatc tcaaaaaaaa aaaaaaaagt 27420
ccgggcgcca tggctcacac ctgtaatccc agtgctttag gagaccgagg tgggtggatc 27480
acttgagccc aggagttcaa gaccagcctg gccaacacag tgagaccctc cctctgtaca 27540
aaacgtaaga aaacattagg cagggatggt ggtggcttcc tgtagtccca gctactcagg 27600
aggctgagac agaagtaccg cttgagtcca ggagttggag actgcagtga gctatgatcg 27660
caccactgca ctccagcctg gacaacagag caagacccca tctctaaaaa aaagaaaaca 27720
aaaaaacaac aacaaaaaac accaatagaa tgctcaatca gccatcagcc tcaaggaccc 27780
ttccatctcc caaggagagg aaccctttc cgtgagaacc tctgacctaa aaatcaaccc 27840
cacatggggg aatccagaaa gtattttggg gggaggaaaa gatgtttgaa gggagggtgg 27900
aggatgcaga agggttaacc aggagaggca gttagggagg gccttctggg tggagggaga 27960
ggactgcatg ttccaaggac ctgaggcaga atggagtgtg tgtatttaga ggaactgaaa 28020
gcaaatttgt gggacagggg atctagaggg gaaaagtgaa ttccacaggc tccctgtctc 28080
ttctggtcct agcaggaact ttcaagtccg tttttgtcca gatatttccc catgctcaag 28140
tcccagctca tcctgcctcc ttgaagacat gacttctgtc tcttcttgag ctactctttg 28200
acacaccctg gacaaagggt agcttgaaaa gagacagaaa ccatgttatt gccaggtgca 28260
gtggctcacg cctgtcatcc ttgtgctttg ggaggctgag gcaggaggat cgcttgaggc 28320
caggagcttg agaccagcct ggacaacata acaagacccc atctctacaa agataaaagg 28380
gaaaaagccg ggcgcagtgg ttcacgcctg taatcccagc actttgggag gccaaggtgg 28440
gcagatcacc tgaggtcagg agttcgagac cagcctggcc aacatggcga aaccccgtct 28500
ctactaaaaa tacaaaaatt agatgggcgt ggtggcgggc acctgtaatc ccagctactc 28560
gggaggctga ggcaggaaaa tcacttgaac ccaggaggtg gaggttgcag tgagctgaga 28620
ttgcaccact gcactccagc ctgggcgaca gagtgagcct tggtctcaat caatcaatca 28680
atcaatcaat ggaaaaaaat tagctgggtg tggtggtcca tgctggtagt cccagctact 28740
gaggaggctg gggtgtgagg atcacttgag cccaggaagg ctgagactgc aatgagctat 28800
gatggcatca ctgcactcca gcctggacaa caaagcaaga tcccgtctca aaaaaaaaga 28860
agaaaaagaa aaatcatttt ttgagagctc tgattttcaa accctttgtt ctcagaactc 28920
ttcgggtaaa accttttgaa cgacacaaaa ggagtgggca gctgtgatga cagattgagg 28980
agaaagcagg gtaggcatgg aacctctagg gttccctagg gacccagttt gaaaactctt 29040
ggttcagtag caggaaaagg caatatgccc cttaattctc ttctaaaaca taaaatcctt 29100
taacttcctc tgatttctac cagtaaaact gagctctact gacctcaatt ttgtaccaaa 29160
tgctatctaa taaaatccca gaaacagtga tttttgaaaa atccattttg ttgatgtgta 29220
atttacatac agtagaatgt gcctatctta tgtgtttggt ttcatgcatt gtttttcttt 29280
ttcaactttt taaatttttt tttttttttg agacagggtc tcactctgtt gcccaggttg 29340
gcgtgcagtg gcacaatctc ggctcactgc aaccttcgcc tctcgggttc aagcaattct 29400
cctgcctcag cctcctgagt aggtgggacc acaggcacgc gccactacac ccagctaatt 29460
tttgtatttt tagtagagac agggtttctc catgttggcc aggttggtct cgaactcttg 29520
acctcaagtg atccacccac ttcggcctcc caaagtgctg ggaccacagg cacacaccac 29580
cacgcccaac taatttttgt atttttcata gagatggggt ttcaccatgt tgcccaggct 29640
ggtctcaaac tcctggcctc aagtgatctg cctgccttgg cctcccaaag tgctggaatt 29700
acaggcataa gccaccatgg ccagccctct ttatcaactt ttatttattt tttcattttt 29760
ttgagacgga gtctcgctct gttgcccaaa ctggagtgca gcggtgcgac ctcagctcac 29820
tgcaacctcc gcctcccggg ttcaagcgat tctcctgcat cagcctccca agtagctggg 29880
attacaggtg cccgccacca cgcccatcta atttttgtat ttttagtgga gacggggttt 29940
caccatgttg cccaggctgg tctcgaactc ctggcctcaa agcgacctgc ccgccttggc 30000
ctcccaaagt gctgggatta cagttgtgag ccgccgcgcc cgggaccctc tttatcaact 30060
tttattttag attcagggga tacctgtgcc agtctcctac ctgagtatat tgcatgatgc 30120
tgaggtttgg ggtatgagcg actctgtcac ccagatggtg agcacagcac tcaacagtta 30180
gattttcaac cctcatgccc cttttcctca cccctccctg gcaatcccca ctgttcatta 30240
ttgccacctt tatgtccatg agtacctgaa gtttagatcc cacttataag tgagaacagg 30300

-continued

```
cagtctttgg tctgctgtta ctgagtttga tgcattttga caaatgtgtc tacctgcctg  30360
ctgcacgttt tggttttccc aagaattatt ttctaaaaat cagtttttat taaggtggca  30420
tttatataca ctaaaattct gcacacgatc ttgtaaccat caccaccaaa tacgtattta  30480
tttatttatt attatttttt agagatggcg tctcactctg tctcgatctc ccacgccggg  30540
gtgcagtggt gccatcagag ctcactgcat cctccaactc ctgggctcaa gcgatcctcc  30600
tgcctcagcc tcctgagtag ctaggactac aggcacccac caccacccac agttaattga  30660
aaaaattgat tcttctttgt agagacaggg tctcatatgt tgccaggatc cttggtcttt  30720
gacctcccaa agtgcagaga ttacaggcat gcaccactaa tgccgggcca aatacttgta  30780
atttaaatta tcgctgggct gggcacggtg gctcacgcct gtaacccagc actttgggag  30840
gccgaggggg gaagttcacc tgaggtcagg agttccagac cagcctggcc aacatgctga  30900
aaccctgtct caactaaaaa tacaaaaatc agccggacat tgtggcagac gcctgtaatc  30960
ccagctaatc gggaggctaa gacaggagaa tcgcttgaac ccgggaggca gaggttgcag  31020
tgagccgaga tcgcaccatt gtgctccaac ctgggcaaca agagcgaaac tccatctcaa  31080
aaaataataa taaaataaat tatagttgga aaaaaggggt ttcctaaaga cccaagggaa  31140
atggcctctt tgttcctgaa gccacagaga ggattttttct gctccccaca actagttttc  31200
cttgtgaaaa ttcataattg ctaccagctt gttctcctct ctgtcactat acatctgtcc  31260
ttgaagcctt atttgaacaa agagttctgg tatcactcgg atgcctagaa actgttgccg  31320
ttctgtgaaa ccgaccacca gaggaaaccc atgcttctca ttggctgcct tactaagatg  31380
gtgacttgtt gccctggtga caagttgcaa tgacaggtgg ctctgccaaa tcagaacaca  31440
gtgatacttg cttcccctcc cgggtgaagg atggaaaata aaagtaaaag ccttggcggc  31500
tgtcaggctt ctttaccaaa gagctggaga gcactccttg gccccattta tgcaaacact  31560
tcccatctac agatgatcca gcttcggagt gggagtctaa gcagctgcca ggaccaccgc  31620
ttggcagagg acaggctggg ggctctggca tgacctgctg gggccaggct gtgacttgga  31680
gcaagaggta gcaagaacct cgaggcagtg aacatcaaaa gagagatttc cggggctaaa  31740
caccctaggt ttttccttcc tcctgaaccc taaccctaac cctctcggct cactgcaacc  31800
tccacctccc gagtgcaagc aattctcatg cctcagcctc ccgagtagct gggatcacag  31860
gcgtgcgcca ccacgcccgg ctaactttgt atttttatta gagacggggg tttctccacg  31920
ttggtcaggc tggtgtcaaa ctctcgaact caggtgatct gcccgccttg gcctccaaaa  31980
gtgctgggat tacaggcgtg cgccaccgtg cccagcttat ttttgtattt ttagtagagg  32040
tggggtttca ccctgttggc caggctggtc ttgaactcct gaactcaagt gatctgcctg  32100
cctcagcctg ccaaaatgct ggggttacag gcgccaggcc aagtatctta ttttaaaagg  32160
ttacaaagaa tatagatgtg gataaaataa aagtttcttt gcattaccac tttcctgcaa  32220
gaaatgaggg ggaggggctt atgaaacaac tcacaccccc ccaattgagg aactgtagat  32280
gaaagggaag gtgctgacag gcccgtctgg ccacggtttc ctggaataaa actgagccac  32340
acacctccac aaatccccag cctccggcaa gtaccccaga agtactcaca ctccaccacc  32400
ttctgtgatc gcaacagccc tacgcaacat tacagagggc aaaacccacg ctggggaagg  32460
cggggctact gtcaaaaggt caccagggcc aggcacagtg gctcacgcct ataatcccag  32520
ctccttggga gaccaaggca ggaggatccg ttgagctcaa gagtttgagt tcagcctggg  32580
caacacagga aaaccccgt ctttacaaaa actttttaaa aattagctgg gtgtggtggc  32640
atgcccgtgt aatcccagcc actacttagg aggccgaagg gggaggatct attgcttcag  32700
```

cccgggagtt tgtggctgca gtgagctatg attgcaccac tgcactccag cctaagtgac 32760
agacagagac tcttaaaaaa aaaaaaaaaa gggcagggca cggtggctta tgtctgtaat 32820
cctagcactt tgggaggccg aggcgggcag atcatctggc gtcaggagtt cgaggccaac 32880
ctggccaata tggtgaaacc ctgtctctac caaaagtaca aaacttagct gggtgtgatg 32940
gtgggcacct gtaatcccag ctactcggga ggctgaggtg ggagaatcgc ttgaatctgg 33000
gaggtggagt ttgcagtgag ccaagattgc gccactgcac tccagcctgg gtgacagaat 33060
gagactctgt ctcaaaaaaa aaaaaaaaaa gtggggcacc tatattccca gcactttggg 33120
aagctgaggc aggaggatgg cttgaggcca aaaattcaaa acccggcctg ggcaacatag 33180
caagacccca tctctatgaa aaaaaaaaaa aaaaagtcac caggccagct agcctagatt 33240
tcagagccag aatttgtctg atgccattgt ctttactttt tctttttctt tttttttttt 33300
ttgagacaga gtctcactct gtcacccaag ctgcagggca gtgggacaat ctcagctcac 33360
tgcaacctct gcctcccagg ctcaagcgat tctcctgcct cagcctcctg agtagctggg 33420
attacagaca tccaccacca tttccagcta atttttgtat ttttagtaga ggtgaggttt 33480 caccttttg gtcaggctgg tctccaactc ccaagctcag gtgatctgcc cacctcagcc 33540
tcccaaagtg ctgggattac agttgcgagc caccacgcct ggactgctct tcattctttt 33600
ttcagaactt tcccagctgc caacagagac agaaactgaa tcatctcaga agtgaatgaa 33660
ggaggctgag ggcgggtgga ctgcttgatt aggagttcga gatttgccta ggcaacatgg 33720
aaaaagcctg tctctgctaa aaatacaaaa attagccggg cgtggtggca catgcctgta 33780
atgccagctg cttgggaggc tgaggcagga gaatcacttg aacccgggag gcagaggctg 33840
cagcgagccg agatcgcgcc actgcactcc agcctaggta acagggcgag actccgcctc 33900
aaaaaaaaaa gaagggaatg aaggacaccc aaaatggagc ctctgtctgc cagggctttg 33960
ctatcctggc ctgcctatcc cagccctgga cacctcatct ctgatcccac cagagcggaa 34020
ccttcccatt cgcagggcca tttccttacc cagaaacctt ttcacaatgt tcttggcagc 34080
agctgttggt caactgtgtt ttaaggtttt tgagcaactt tacagaaaat aaaagggaag 34140
ctaccctcaa tgtctgggtc tccccctggg tggcctctct ttgtcacctt actcatttcc 34200
acgagatttc cttgcttcgt tgagttacat cacctccttt tcctgtctgg gtccaggacg 34260
cctcctctgc aggtctccag cactgattcc tttgtccccg atttctctgc tagggtcgct 34320
ggcttcacca tcccaccacc actgctgctg gcccagcccg cagctttaat ttctctggac 34380
cctcacgttt ttgttatttg tgttttttttt ggagatgagg tcttgctctg tcacccaggc 34440
tggagtgcag tggtgcaatc acagctcact gtagcctcca cctcccagac tcaagtgatc 34500
ttcctgcctc agcctcccaa gtagctgggt gtgtgccacc aggtgcagct acattttttg 34560
tagaggcagg ggtcttgcta tattgcccag gctggtctca aactcccagc tttagatgat 34620
cctttcacct cggcctccca gagtgctggg attaccagca tgagccactg cacccgtcct 34680
ctcatgtatt ttttattaat cgatttatct atttacttat tttgagacag agtcttgctg 34740
taccacccag gctggagtgc agtggcatga tctcggccca ctgcaacctc cactccctgg 34800
gttcaagtga ttctcctgcc tcagcctccc gagtagctgg gattacaggt gcccgccacc 34860
atgcctggct aatttttgta tttttagtag tgacgaggtt tcaccgtgtt ggccaggctg 34920
gtctcgaatt cctgacctca ggtgatccac ccaactcggc ctcccaaagt gctgggatta 34980
caggcgtgag ccaccgcact cggcctccct catgtatttt taagcggaac aggttcaaga 35040
tcacaaatgt tttcctctca ctctttcaat gagtttctat tctagaatct cctgcacgcc 35100

-continued acaggaagga gaactctcac cctgtaatgc acataaatac atgagatcac cattgttctc 35160
acccagtaat cagaatcgtt agtgataatt agtaataaat ttatttttac tatatctaat 35220
aaattagata gtaattacta tggcagccaa tcgttcctgg gtgctcccta gatgcttcca 35280
agggagccac acgtgaccct cagggctgtg cccattccag gctcttctgc tgagctcatg 35340
taaccgcttg cctcaaggca ttccacaaat aatacataag tcaatgtatc acgttgtcac 35400
tttctgtaca aaccagctag ttccggaggg aagcagaaag ccttttttcag aagaaccaca 35460 gctaattcca gtagcaggaa tgataaagtt ggacataatc ctcaagagag taatgaatca 35520
aaaatggatg gcgggccagg cacggtggct gatgcctgta atcccagcac tttaggagga 35580
tgaggcaggt gaatcatttg aggtcaggag ttcaagacca gcttggccac catggtgaga 35640
ccccgtctct actaaaaata caaaaattag cctggcatgg tggctcatgc ttgtagtccc 35700
agcttcttgg gaggctgagg caggagaatt gattgaaccc tggaggtgga gattgcagtg 35760
agccaagatt gcatcactgc actccagcct gggcaacaag agcgaaactc tatctcaaaa 35820
acaaacaaac aaacaataac aacaacaaaa ttgatggctg ctaatgactt tttttctttt 35880
ctttcctttt ttatttttat tttttatgag acagggtctc actctatcgc ccaaactgga 35940
gtgcagtgcc gagatcataa ctcagtgcag cctcaacctc ttggactcaa gtgatcttcc 36000
cacctcagcc tcccatgtag ctgggactac aagcaattgc tgccacatct ggctaattat 36060
tttattttgt tgtattttat ttatttattt tttgagacag agtcttactc tgtcacccag 36120
gctggagtgc aatggcatga tctcagctca ctgcaacctc cgcctcctgg attcaagtta 36180
ttctcctacc tcagcttcct gagtagctgg gataacaggt gtgcaccacc acgcctggtt 36240
aatttttggt tttttggtag agacggggtt tcatcatgtt ggccaggctg gtcttgaact 36300
cctgacctca agtgatccgc ccatctcagc ctcccaaagt gctgggatta caggtatgag 36360
ccaccgtgcc cggtctttat tttattttta gtagagacag ggttttgcta tgttgcccag 36420
gctggtctca aactcctggg cctaagtgat cctcctgcct tggcctccca aagtgctggg 36480
aactacaggc gtgagccact gggcccagct cctgttaaca tctttatgtg gagagttact 36540
ggggaccagg gacattcccc aaacccaccc atcaatcgta gtgacatgac gttatggacc 36600
ccctgatgtg atgtaccagg aagtacccgg ccctaccagc atgatattat tctggctgca 36660
actgaccctt attccaatag agcatgtggt tctaagccat ttatagggta aacattgggg 36720
cagggatggg gagagaggaa gcaacctgcc aaatccagaa tgaggatcat tcctcggtac 36780
cagaagagaa ccagaaagaa agcaccctaa gtggggatac cacaaggaag taaagcaggg 36840
gcctctccca gctggggaag ggaaggagga aggagtacaa tagcttgcaa ggcacagcat 36900
tgcggatgat gggaatagca ggtgcaaagg ttctggggca gggacagtgt ggtgtgtttg 36960
aagaacagca gccaggttca ccatgagatg ggaaatggac ttgggggaag ggatctcaaa 37020
ggataatttt tttttttttt ttgagacagg gtttcgctct tgttgcccag gctggagtgc 37080
agtggcatga tggctcactg caacctctgc cttccggttt caagcgattc tcctgcctca 37140
gcctcccgag tagctgggat tacaggcgcc caccaccacg cccggctaat tttgtatttt 37200
ttagtagaga cagggtttca ccatgttggc tagactggtc ttgaactcct gacctcgtga 37260
tccgcccgcc tcggcctccc aaagtgctgg gattacagac gtgagccacc gcgcccggcc 37320
ccccaacttt tttttgttt ttaacacaac ttctcgcttt ctcacccagg ctggagggca 37380
gaggcacaat catagctcac tgcagcctcg aactcctagg ctccagcgat cctcacagga 37440
gggttttgag gatctgcata aagcgtgcag agggagcttg acttcgtgct cgttaggacc 37500

-continued

```
cgatattgtc agctgccgcc gcccacaggg acacataaat atttgtagac tcaatatttg  37560
cctttagtgt gaagacattg catcacctgg gtataagtaa ggagcagagg cagaggcggt  37620
ttaagcaaca gacttttgtc tccgctgaga accacggaat aacccctgac ctacttcccc  37680
gtcgtgtcta attcgggtca cctcatctcc agttacagac gcggaagatc aaagaaaccg  37740
ggaaattgcg ccgcagcgcc ccctggcgtt cgcagcgcgt gcctacacaa gccactcccg  37800
gcgcaaaact gcggcttccc aggaaattga gtttaaatgt tttttttct tttttcttaa  37860
tctagaaaag atcatttatt gtatcaagta actacccagt taggcgtgaa tacattttaa  37920
aatttttatt aaaacgagta ttggccgggc gcggtggctc actcctgtaa tcccagcact  37980
ttgggaggcc aaggcaggtg gatcacggcg tcaggagttc gagaccatcc cggccaacat  38040
ggtgaaaccc cgtctctact aaaaatacaa aaattagctg ggcgtggtgg cacgcacctg  38100
tagtcccagc tactcgggag gctgagacag aagaatcggt tgaaccgggg aggcggaggt  38160
tgcagtgagc tgagatcatg ccactgcact ccagcctggg cgacggagcg agactccatc  38220
tccaaaaaat aaataaataa ataaatataa tataatataa aataaaataa aaagagtatt  38280
gtagagattg gctgggcaca gtggctcaca cctctaattc ctgcattttg ggaggctgag  38340
gtgggaggtc ttcagcccag gagttagaga ccagcctggc caacatggca aaaccccatc  38400
tctactaaaa gtacaaaaat tcgctgggca tggtgtcgca cgtctgtgat cccagctttt  38460
tgggaggctg aggcaggaga atcgcttgaa cccaggaggc agaggttaca gtgaatcgag  38520
atcgcaccac tgcactccag cctgggcaac agagtgagac cttgtctcaa aaatacatat  38580
atttaggaat ttgctatgtt gcccaggctg gcctcaaact cctggcctca agcaatcctc  38640
ccacctcgcc ctcccaaagt gctgggattg caggcgtgag ccactgtgcc cgaccttgag  38700
cttaagtttt aaacattaaa accacctccc tcccactccc tgcacctccc gtaagttaaa  38760
acgcgtccct gctgaggccc tgcaaaggca tatccagggc aggcggaccc caggggtcca  38820
cagccgaccc actttcttcc ccacacctca tcccccttcac aactctcctc atccatctcc  38880
ctgccctggt gggagattcc gataaatcct aattgtggaa ctgctgaatc agagggggct  38940
gcattttcct tagcccccac ctgcaaattg tgtgtgcagt ttttctggga tgagtgtcct  39000
tagatttccc tgaattctca aaaggatctg tgacctcaaa atcaggagag aggccgggca  39060
cggtggctca cgcctgtcat cccagtactt tgggaggccg aggtgggcag atcgcttgag  39120
cccaggagac cagcctgggc aacatagcca gacccagtct ctacaaaaaa ttaaaagatt  39180
aactgggctt ggtgatgtgc actcatggtc ccagctactc aggaggctga ggtgggagga  39240
tcgcttgagc acaggcggta agagaggctc tacctctgaa gaggatgctt ccccaccctc  39300
tgccccctcc ccaggcaccc actccagcag tgagaatttc actgccaaca tgagacatgg  39360
gtccctacct gtcccaactc agaccctgtc tatgatgtcc tatggcctca gcagggacca  39420
aaaccctcac catggcctca ccagaacctc cacgtggttc tcagattggg ttgcaggtca  39480
gtaccctccc ctccagctcc tcaggggcct cctgcattct ctggccttgg cttctgctct  39540
gccctcccct cccttccctt cgccccccttc attttcattc tctatgcaaa tgctgcctcc  39600
tctaggaagc cttccctgat tgcccccagt ctgggtggat tagatgtgat atgggctccc  39660
acagcccctt ttgcctcaga ttactcatgt ggctggctgt atatctgtgc cccagagagg  39720
tttcttttcc tttttctttt ttttttttt ttttgagata gggtgtcacc ttgccaccca  39780
ggctggagtg cagtggcatg atcatagctc attgcagtct caacctcccg ggctcaagca  39840
atccttccac ctgaaagtcc tgagcagctg ggactacagg cgtgtgccat cacgtgcctg  39900
```

-continued

```
actaattttt cttatttttt gtagagatgg ggtcttgcta tgttgcccag gctggtctta  39960
aactcctagc ctcaagcgat ctcccacctc agtctcctga gtaaactgga ccccaggtgc  40020
aagacaccat gcccataaaa aaattttaaa aaaatttaat tttaaaattt ttttgtagag  40080
ataggatcgt gttatgccgc ccaggctggt ctcaaactcc tgggcccaag cgatcctccc  40140
acctaggcct cccaaagcac tgggattaca ggtgtaagct acctcgcccg gcctctcctg  40200
ttctattggt gctgtgagat tcacacctca cttgagtgct atgggctgaa ctgtgtcctc  40260
tccacaaatg tctatgctga agtcctgccc cgcaactgcc tcagaaagtg actatacttg  40320
gagatagaat ctttaaagaa ataattaagt aaaaatgagg tcatatgcgt gggccctaat  40380
ccaacatgac cagtttcctt gtaagaagag cagattagga cacagacatg cactggggcg  40440
gggggaggag actgtgtgaa cacacaggga aaacacagct gtctacaagg aaaggagaga  40500
agcttcagaa ggagtcacac ctgtggacat cttcatcttg gacttccagt ctctagaaac  40560
agaagactat aaatgtgttt gctttgagac agagtcttgc tctgttgccc aggctggagt  40620
gcaacggtgc gatctcagct cactacaacc tccgcctccc gaaggaggcg tagtgtaatt  40680
ctcctgcctc agcctcccaa gtagctggta ccacaggtgt ccaccaccac acctggctaa  40740
tttttgtatt tttagtagag acaaggtttc accatgttgg ccaggcttgt cttgaactcc  40800
tgacctcagg tgatccacct gcctcagcct ctcaaagtgc tgggattata gttttgtttt  40860
tgagatggag gtctcgcttt tgtcacccaa ggctggagtg cactggcacg gtcttggctc  40920
actgcaacct ctgcctccca ggctcaaatg atcctcccac ctcagcctcc tgagtagctg  40980
ggaccacggt gcacaccact acattcagct aattctattt ttttgtagac acaggatctc  41040
actatgttgc ccaggctagt cttgaactcc tggcctcaag tgatcaacct gccttggcct  41100
cccaatgtgc gactacaggc atgagccacg gtgcctggca atttctgtta agtcacctag  41160
tctgtggtac tttgttatga cagccctagc aaacagatac acccaccgaa ggccctgata  41220
agtcctgcag tcaggagtct ctgtgaaccc cgtggggctg ggaggagaaa gcagggagcg  41280
tttgctgtgt gcctcacatg aatacagcag aagctgaaca caactcctgg catcgtatgc  41340
ctacaggtcc ccttggaaca gttctagggg ggttggagtt ccagggtcca ttctgcttaa  41400
taacaatatt aacggagcag ccaaaatggt tccagtgaaa atggggtagc agcagctgtc  41460
atgcttgcac gccaccagcc ttcctgcgct atctctgttc tctcctctgc aaagcagctg  41520
ctattttggg ctccctgttt ttagattggg aaccccggaa gttggtcagg gcctcaccgc  41580
tagaatatct tagagctgat attcaaatga gagtccaatt tttttttttt tgagacggag  41640
tctcgctttg ttgcccaggt tggagtgcaa aggggcaatc tcggctcact gcagcctcca  41700
catcctgggt tcaagtgatt ctcctgcctc agcctcccaa gtagctggga ctacaggtgc  41760
acaccaccac acccagctag ttgttttgta tttctagtag agatgggttt tcaccatgtt  41820
ggccaggctg gtcttgaagt cctgacctca agtgatcctc ccgccttggc ctcccaaagt  41880
gctgggatta caggcgtgag ccaccgtgcc ctgccaaaag tccaagttct taacctccat  41940
gagggcttga gatgccctca ggggcaggga gaggctaatt ctccttctga gaggataata  42000
ggggttggtg gggcctgggg cacaggcctg gctcagcaca actcccaggg actcccttga  42060
taagaaggtg aggtaggcac tggctggcag agcgacggga agagtttatt tctctggaaa  42120
gggaggggta gggggcgggg ccaggggtca gggcagggca atgtcctcca gcttcttgtc  42180
cagtgccttc aggtcatcca ggaagcgggt cggggtgagg atgtgtgagg agcctgtgca  42240
ggggcagagg tttggggaag atgttggggg gcgctgcctt cgtctttgac aggctcccgg  42300
```

-continued

```
tcccggctgg tgtggggctg tccctgtccc tcagcaaacc aggtccctga ctccaaggac  42360
tctggagtcc agacacctag aaggtacaag cccaggcccc gggaacccaa gccccagacc  42420
ccagggtccc agtcctggtg acttaccaat gagcacctcc cacttgccct cggtggccct  42480
ggtcacctcg taggcggccc tcatctctga catggccaca ccgcccatga catacacgat  42540
gagccggggg cccgcccggg cttctatgcc agccttgttc ttgtgccagt gaccgaagcg  42600
ggcactgtgc agggcagggg cagaaagtcc aggcaggagg ccctcaccgc cgccaggccg  42660
cccacctaac acagacccag gcgtgggcgg gggcggcccc ggggcctcac ctgacagcgg  42720
cctgggagct ggccgtgggg gcggggtcgg atacgaaggg ccacaggttc ctgtccagcc  42780
ggtcctccac ggcgtcctgg cggccgagag gcaggttagg ggaggaaccc caggcatggg  42840
gtccggggtc aggagtgccc cccacggggt attcaggggc caagatcctg gcagacagga  42900
accagcatct ccacctcctg cctctggggg acccaggagt ctaggcctct agtccattgg  42960
ggacctagaa atctagatcc ataactcact ggggacccac gaatctaatt ccataactcc  43020
ttgggtaccc agaagtctaa acccacagtt cctcggcaac ccagtagtct gggcctccag  43080
gcccttgggg accatcagtc aatacccccca gccctttggg gaacccagtg tctgggctct  43140
cagcccctca gagccccaga agtccaggta ttcaaggtcc atggggatga ggaggcccag  43200
gtctctggcc cccacgcaga aagaggggcc ggggctctta gagggacaag gaggaagcca  43260
ggaagccgcc ccaggcccat tgccattgga tggtgctgcc ctgggatcct gggaaggcca  43320
gggctggggc tcaggggcac tcctgcggga caggggaaca gactagagag atatagcgga  43380
ggcagccggc aggtggggag gaagtgaggc tccccagcac aggccccgct gtcaccccaa  43440
ttcctcagct gcgggcttgg cgtgcccccc tcagcagagc agatcggtgc caagggaatg  43500
ccagcaatga gcattttccc ctaagccctg aggcttagca cctcagcagg agggaggctg  43560
agccgccagc cgatgcggag ggctggcccc caccctgacc tgccacccag tacctccatt  43620
acatccttga tgaccggggt ccagcgggac agctgatagg tgggctccat gcgttctctc  43680
ggctccagcc ggctggaggt ccccgagccc tacaggcagg gcagggaggg cagcaggggg  43740
attgagggga aggaggctgg tcacagaggg gctgcgcctg gtgtggctgg tagggtgggg  43800
gatggcaggc aaagatgggg aagtggaaca gagagcgaga gagagcgaga gacagcaaga  43860
aagcgagaga gagaaacagt gagccagaga gagacggaga gagaaagcca aagggagaga  43920
gagcgagcca gagaaagaca aagacagagg cagagatagg caaagagata agaagcagtg  43980
agacaaagta tgaaggcaaa gagagagaca agagatgaag caggaaacag agagaggaag  44040
atggggacag aagggggacg gagaggggag gggagcaaga cagagaacag agagaaaggg  44100
gaaggcagag agaagggtga gagagagaga tatggagaaa cagtgcacag cgagatggat  44160
gagggatggg ggagagatgg ggacggggtg agggcaccct ggagggggac gcacagggcc  44220
agagagagac aggagaggct gacccaagag tcaagcacac acatggctgt gtgtgggtgc  44280
tggatgggtg cgggggaccc tcagagaccc ctgggagccc agatagacaa tgtggtgtag  44340
cccccatgct ggggacccta ctccctgcct ctagcactca gaccacccgc tcccaactgc  44400
accactgcca ggaccagcct ggcagcgacc atgtctcact tcccctgcct attgtgtaag  44460
ctgggactgg gagaggcccc agtgtcctct gggccccaga ccagacccga aacactgctt  44520
ttggcctccc agcaaccaca ccacgccagg aaccacaccg tgcctgtgca ccaatggccc  44580
tctgccttgc agagccccgg ctgtgatccg caccctctcc cagggtcccc ccatgcccgc  44640
tcctggcgta ccccggggtt ggtgacagtg cctcccagct gctccaggtt acggatgagg  44700
```

-continued

```
ctgctgtgcg cctgtacatt ggcatgctgg atcagcttgg ccaggttctc ctcactcaca  44760
cctgggggac gggaatgggc agggtggagg cggcggccag gtgagctccc aggtttaggg  44820
gagtttgggg tgggctgagg agctcccagg actctgatga gagaaccttg cagtggggag  44880
ggcctcagta ccctgtgcta gtgtgagcaa gagtgggaaa cctggagggg gtagatcagg  44940
ggctcctcca gatgagctga gggagcccca catctatagg aatcacagat gtgagggttt  45000
ctacgttagc agggagccct cacctcagtg gaggaatccc caagccaatg gaggagggtt  45060
cccgggtcca gaggggtagc tgtgggggtt ggtgagcccg gtgagtgcaa atgacccaag  45120
gagagctgtg gggttcagca gttcccagga tcgtgggaga cgctggcaaa tggggacgtt  45180
ccaactccct gcagccccca cccaccattc cgaaggagga tgtagagcag caggacccgg  45240
atcttgtcgt aggcgggcac cgccgcgtcc agcagcaccg gaacgatcag cttcatggag  45300
tccttgatct tctccccctc tgcgtcggag cccatggcca ggtcctgcgg gcatggggtc  45360
agccgtccac cggccgctat gtgtcaggga aggggatggg agaggcgggc caaggacatc  45420
cccaggatcc tcggcaagag gacatttggg tcctacctca tctcagcacc aggtctctca  45480
aggtcccacc cctgtccagg gacagtctct ccacaggccc tgctcctcac ccaggtccca  45540
cctttccagt gccccaccca cctacacaca ggtcacacca ctatcctgag actacctctc  45600
caaggctcca cccctcaccc aggtcccagc tctccaaggc tccacccctc acccaggtcc  45660
cagctctccg aggctccacc cctcacccag gtcccacctc tccgaggttc cacccctcac  45720
ccaggtccca cctctccgag gttccacacc tcacccaggt cccacctctc cgaggctcca  45780
cccctcaccc aggtcccacc tctccaaggc tccacccctc acccaagtcc cacctctcca  45840
aggctccacc cctcacccag gtcccagctc tccaaggctc cacccctcac ccaggtccca  45900
cctctccaag gctccacccc tcacccaggt cccacctctc cgaggttcca cccctcaccc  45960
aggtcccacc tctccaaggc cccgtgcctc acccagatcc cacctctcca tggctctacc  46020
tgtctcccag ctcctacctc tccaaggccc cacccctcac tcaggtccca cctctccaag  46080
gctccgcccc tctcccaggt cccacctctc ttaaggctcc acccctctcc caggtcccac  46140
ccctccaagg ttccacccct catccaggtc ccacctctcc aaggttccac ccctcaccca  46200
ggtcccacct ctccaaggct ccgcccctca cccaggtccc acctctccaa ggctccgccc  46260
ctctcccagg gcccacctct ccaaggctcc attcctctcc caggtcccac ctctccaagg  46320
ctctgcccct cacccaggtc ccacctctcc aaggctccat tcctctccca ggtcgcacct  46380
ctccaaggcc ctgcctacct ctccaaggtc ccacccacct atgaataggc cacattcctg  46440
tcctgggacc acctgtccaa ggctctgccc ctcacccaag tctgacctct ccaagcccca  46500
tccacctatg cacaggccac accctcatcc taggaccgtt tctccacaag acccactcct  46560
tccccaccag gtcccacctc tctccaaggc ccctccacct ctccacaagc cctgcccctc  46620
ccccagaacc ccccatctct acagttcagc ccctccccaa taccccgcct tggcaggacc  46680
atcacccctg ccccccgcaa gccctgcccc acctgctcca cactacacag cttctccacc  46740
gagcccttga agtgcttcat acaatcatct gctagatgca ggtgcgtaga atactgcagg  46800
gtgcagggtg ggggttgggg gataacaaag gctgagtcaa ggcagaacgc agacagagca  46860
tggggttgag gggccgaggt gtccccgctc cctgcccacc cgagcacacc ttattcagct  46920
ccttctggta ctgcggcatc tttttcagga tctgggatag gtctttgatg ttcgcctggg  46980
gaagtagggg gaagagggta gggattgggg ggcgaagcca ggcagtgccc acctgggtct  47040
cagtccaggc tcgaaatcca ggctgtggcc ctgcgcccat ggggaggggg gcttccttcc  47100
```

-continued

```
accagcgcct ttggtgacct gggtccgccc ctaccttgtc cgtggtcagc ctcttgctct  47160
cacagaaggt cctcaggagc tccgtgacct tcctggccat gagggtgggc gggggtgaga  47220
gtgaggggag aggagccaca ggccatgggt gagcccactc aggggggaca gggagaggtg  47280
gggtgaaatt ggaggccagt ctggagtcac acgaggggtg ctcatgaggg ccaaagactt  47340
ggcagcagcc agggatccca aggccgctac caggcccaca gtgggcggtg ggggggggat  47400
ccggtccccg tgtgcacgca cttggacaca tctgcgatat gcatgtggcg aagctccacc  47460
cacaagtcat cgtcctcgtc cagcaagacg gccttctccc gcgcctcgct cagcccggtg  47520
gtctcatacc tggggaggaa ggagggagcc tgggggtcag gggagctgag gactggggaa  47580
ccaggtcagt ggcaagggtg gggacgggtt ccaagtctgc agacctgtat gtgtcctgct  47640
ctatgtccag cagatcatac gccatggcct ggaacgtgag ctcatgcagt agtggggaca  47700
cggggtcagc tgcccggtcc attatcagca gctgggagcg ggttttctct gggccctggg  47760
gtggggttta gggcaggaat gaggcactga ccctgagccg gttggggctg cccctcacct  47820
cccaagcacg ccccctcacc tcgcccagac tgggagtgtc tgccttgaag gcgttcagct  47880
tggccaggac ggcgtgggcc aactgggctg tgtcctctgg gcccctggcg gggaggtcag  47940
acacggggga catcatcagg ggatggggtc aaggatgggt ttgaaggtga gagtcagggg  48000
ccagggtagg gccggggctg gggtcacaag agaggttaaa ggttaggtgt tgcacgcggt  48060
taagggggggg tcggcatcgg ggtggggctg ggtggggtcc ccacttgcgg tagcggatgg  48120
ccgggtactc ctgcagggtg gcgcacagcg tggcaatctg ctgggccagc acctcgagct  48180
gccgcgtgcg ctcctctgcc cggaaggggc agtagaggtt gtaggtgctg tggggagcat  48240
cgagggagaa cacctgggcg aggaggggac agaagcacca gggttgccgc tgcaggtgca  48300
cacctgcccc gcttcccgct gccgccacct gcacctcctg ggagccgtcc ctggtccctg  48360
aagcctgctt tgccgaattg gaggcaggcc caggtcaacc ctaaacccat gcctgcagga  48420
gtcagtggat aaatacccca gcccgtgtcc cttaagctgg ctggacaacc ccgcggtgcg  48480
ctctacgctg ccccctgcaa gggcctagtg ggatagaact caaggcaaga gctccttgga  48540
ctctgtgggt acctcccctt tttaaaattt tactttatgt atgtttttga gacaggatct  48600
cgctctgtcg cccaggctgg agggcagcag tgcaatcata gctcactgca gcctcgacct  48660
cccgggctca agcgactctc ccaccccagc cccatgagta gctaggacta caggtgcacg  48720
ccaccacgcc aagctaattt ctttcttttt cttttttttaa gagacggggt cttgctctgt  48780
acccaggctg gtctcaaact cctggcccca agtgatcctc ctgccctggc ctcccacagc  48840
gctgggatta caggtatgag ccactgcgcc cagcctcagt gtctgtttct gagggaacag  48900
gggacatttg gtcacaaacc cccacccccct gcccaggatg agcccgggcc gtacctgggc  48960
ctcgtagggg aggaaggcaa ggtgaatctc cttcaacgtc ttcaccacct ttgccagacg  49020
agagcggcct agctcactga acaggggctc ggggcaggct ggggtgaggc aggagtgggg  49080
catcaggcca gagcagcccc cacacctcct tgccccaccc accaacaccc taggctctcc  49140
tcactcactg tcggtgaaga agatatgggc cgctttgtag gtgaaagtcg gggtcccctg  49200
gaagtctttg atcagggcct gaaccgactg gggaaggtgg atcactctct gggcctgagc  49260
ctgcacacct aggctcattg gctgcctagg cctcccagcc accccccatc tgccaccatg  49320
tgcaaacatg gacggacggg gacatgtata tgtgcaaatg cacactagtg tcgcacccac  49380
atgggcacac gcgcacacac acagatgcac gcacgcacac acacatacac acgcatgcac  49440
acatgcacac acacacagat gcacacacac atacacacat gcacacacag agatgcacac  49500
```

-continued

```
acatacatac acacatgcac acacacagat gcgcgcgcac acatacatac acacatatac  49560
acacatgcag acactgatgc gcacacacac gcatacacac atgcacagac gcatacacac  49620
acgcatacac acgcacacac agatgcacac acatacatag acacatgcac acagatgcac  49680
atacatatac acgcatacac acatgcacac acagatacac acagacgcac acacagacgc  49740
agacacatac atacacacgc atacacacat gcacacagac agacgcacac acacacatac  49800
agatgcacac agatgcacac acacatacat acacacgcat acacacatgc acagacacaa  49860
atgcacacac agacccacag acacacacgc atacacacat acacacaaat gcacacacag  49920
acgcacacac atgcacatgc acacagacac atacatagac acacatgcaa acacgcacac  49980
acatgcatac acagatgcac acacacatgc acacacatgc acacacatac acatggacac  50040
atgcacacgt atacacatgc acacatgcaa tcacatgcat gcagacatac acacacatgc  50100
acatgtacac gcatgcacgc gcatacacac acgctcactc atgtaggcac cttctccgtg  50160
gggctcagca aataaatggc ctccagactg ggaatgggtt cccgccgttt gttgatgtct  50220
tcaacaacta gtaggaacag aggaagggac acaggtgggt ggcatccagg cagggccacg  50280
tggggagtct caggtgtggg gggttggagg cttggggagg aggggtggat gcttaggagg  50340
gactgcagga gaaacccact tagggaccac cagctaagag ccacacgaca gggttctgca  50400
ggggttgtgc agccaactgg gttccccaaa tttacagaca gggagactga ggttctgaga  50460
ggacaggctc cctcagcacc tatccctcaa tggcaaagtg actgggacac cacctggggt  50520
cacccataga aggctctgca ttcttgggac cccacatcca gagtccaccc tgggagtccc  50580
acacagggct ccacgaggga gctgcacggt caggaagggg ctgcagccag ggagtgctgc  50640
aggggaggcc tgcaatccat gggctcccgc agtcagcttg caaggtttaa gaatggattt  50700
ggtcacatga tccgggctgt ccgtgcaggg agctgcgtac ttgggagttc tggacgattt  50760
gaggggatcc tacactcaag ggctgaaccc tgggagaggg gcacagtcag gggttcccac  50820
gctcaggtcc catctcactg gggacgcgtt cactcactgg tgatgccctc agccaggata  50880
tctgacattt tgcagcagga agacaagatg cgcatgcttg ggtgatccat gataagcacc  50940
tgtccagatg gatggacaga tggatggagg agcaggcgga agaggccaca gctggcccca  51000
gaaggggcca aggcagtggg aggggcagtt tcaagggctg gctgggtggg aggacccaga  51060
acccattcac ccaactccac ccatgtggac aggcagttct tgggggtccc acattcaggg  51120
tcttccccat aggcctgatg atgagctgcc tctgggtacc cagccatctg cctcacccct  51180
accttccact ccccatcctt cttgacactc cgaataactc cgctcagaat ttctgcaggg  51240
aagggagggg aggggtcaga atgctggttc tctggtccca ccactgcccc aagccttctc  51300
agccttgggg ctgaaccccc atcttaattc ccatttactt tttttttttt tttaagagag  51360
gaggatctca ctctgtcacc taggctaaag tgcagtggtg tgatcataac tcactgcggc  51420
ctccaactcc tgggctccag cgatcctctt gcctcagcct cccgagtagc tgggactaca  51480
ggtgcatgta ccacccacag ctaatttatt tttatttctg tatagatggg gtctcgctat  51540
gttgcccaag ctggtctcaa acttttggcc tcaagcagtc ctcctgcctc ggcctcccaa  51600
agtgctggga ttacaggtgt gagacacggc acaggaatca tttattttta gcccccagtt  51660
ctgcaaattg gcttctgggg tcacccccaa tttacagaca gggaaacaga ttcttaggca  51720
acatgtaact cacctacgca tcctgagtgt ctaagtggca gagtgctggg gcaaaaggtg  51780
ccactcgata aacatgtttt aggtgaatga aaagaggaga accgggatca tctacagctc  51840
tatctgcctc tagcgccagg ctctcggctt ccccacctgc tacctcaagt attcctgctg  51900
```

-continued

```
tgagggtttc agccagtccc cccaacctgg tctaaaatgt aggacccctg gttcccagct  51960
ctgaggcatg cctagctgag gctatcccac tgacctccgg tctcagtttc ctcatctgta  52020
aaatggaatc actttttttct aatctccccc aattaaaggg gtttgagcta cagaccgccc  52080
tgcctagagg agagagtgga gagaagtaac ggggtggccc cgcccagcca cgtccactgt  52140
gtcatgtcca ctgttatcaa gacggccagg gcggaaggag cagctgaggc cggaactccc  52200
cggggtggag gaagaggcgc cctccaccct tcccccaaga accggggccg gtgaggcctg  52260
gacgcctgcg tcctccagct gcaaggcgct cctggaaatg gggcaaggag gaagacatcc  52320
cctacaccac ccctgtgggg cctggacacg tcccctgagc gctcacagca cctagggtcg  52380
ctgaccagag ccctaggagg ccccaagaat ccagcccctg aactttgccc ggcttaagag  52440
atcctagagt gtgggcatcc agctgtgccc tcctccccg gcaggcaccc taggaggccc  52500
aggagtccgg gccccagcct ccgccacact ctacccgtcc cctttgggtc cccggagtcc  52560
ggcccccaa ttttgttctg ttctggcacc ggagagcagg ggcgtccagc tgggaacccg  52620
tccccgcccg ccccctcgag ggtcaggtgc tcggacgccc agcccggccc ccaactccca  52680
gccgccatga aacccaggat cccagagccc gtgcgtcccc gacccccgtc ccacaccgga  52740
cgccagagcc cggccccgga gaggcactca ctttccccca ccaccgcctt cagccccgag  52800
ggcgccatct tccccgaggg gcgccgccgc cgcttccggg tgtgtcccaa ggtgggggcg  52860
tggccgcgcg tcacccacgt ggaccccgcc ccgcgccctg tccccgcccc ctgcgcacct  52920
ggcccctccc cgccgtcggt tctcgcccag gcccaggaag ttgagtccct ggcggggagg  52980
acgggcaggt gcgtccgcgc tgccgagcac gaagtcgctg gaggtgcaca cctcgacgac  53040
acgctcacag atgggagttc agacacacac ttcctggctt gcgtgcgaag caggatcgca  53100
gggcaataat ccctccatct tccccgggag gttctgtgcc tgcaagatac acggcaccca  53160
ctcgatgcca ccgggccgcc actgtctggg cctgggatct tgacccactt gccttctgta  53220
cttcagggtt tagaggcagc agcagcagca gcagccgtct tggataactt ttgatggatt  53280
caggaggcct ggagacctct tgtgtgcagg cacctggaca taattttcat tcagtcctgc  53340
ccaatgttcc gacctggact gcggtgccga cgaggaaacc gaggcttagc gggatcccta  53400
atccaaggcc acgacgagtg agcctgctgg gttcaagcca ggagcctgtc cccagggggc  53460
atttgtcaca gccttaccct cttccgggag ggcgcaacgc ttaccctcgt ggaccaacaa  53520
tcgaattaac atgctgatac acacatgggg tgagtgacgc cctcaaatgc ttgcaaacac  53580
agacacacac tcggaatttc agaagctgct tctgctgtgt gtcctgtcgc ttggaaggca  53640
cagccccagc agcacccata caaaatgagg tctccgattt aaggtgcgag gtatgtgtgc  53700
aaacagactc ttgctggtct gagctggttc cttcgctcgg ccgtgttgat gaaggtacca  53760
agccccctgc cacttacatg ggacataggg agtgaatcag acccgaaggt ctgggggaga  53820
taggaaagga tccatgctgc cctaaaggaa ataaactaat gtgacaacaa gtgccacaga  53880
aggtaggggt gggaggggac tttactgagg atgacccccg agggcctctc tgaagaagca  53940
gccttttgac attatcccta aatggattct agaagcagcc acacagcatg tccaggtaga  54000
gaagggagga gccccgagct taagaaggct ggagggtggg ggcagcaggg gccagacttc  54060
tgtaggacaa ggtcagactg acccatccca gtgccaggat gcaggacttt cagtgctaaa  54120
aataggacag tcacaggcaa accaggacgg ttggcaaccg taggtaggag tttgagctat  54180
ttcttccttt cctttccttt tcccttcctt tcttccttct tctccctcct ccccattttt  54240
gtttgttttt gttttgtaaa gagacgggtc tcgctctgtt gctcaggctg gagggcagtg  54300
```

gcacgatcat agctcactgc agcctcgact tcctgagctc aagggattct tccacttcgg 54360
ccacccaagt agctgggact acaggtgcac gccaccgtgc ccggttgatt ttgttgttgt 54420
tgttaagaga caggatctcc ctatgttgcc caggctggta tcaaactcct gggctcaagg 54480
gatcctcctg ccttggcctc ccaaagtgtt aggattttag gtatgagcca ccgcacgctg 54540
ccccttcctc cttttgtaac agctttactg agatataatt cacataccat acaactcgct 54600
gacctaaggt gcgtaagtca atggctttca gtatttttgg agttgtgtgt ccattaccac 54660
aatccatttt agaacatttc cacaacccct aggtgtttgg gttttgtctt ctcaagagtt 54720
ttgagcaggg gaaggcgggg aaccctccag atcctggggg gatggaagcc aggaccgcct 54780
ccagcttctc agcctgaccc cttgggggga cagagagctg ttagggccag ccaccccacc 54840
actaaccccc aaaagatatg aagtactaat ccccaatacc ccacaatagg atcttatttg 54900
aaatggggtt agtatagata ttagcagtga gcatgaggtc acactggagt agagtaggcc 54960
cctaatgcaa tatcactggt gtccttgtaa gatagttata tgtctgcctg gttctgtgta 55020
ggtggttggg ggggtgggga aatgggtata tgaagactgg gacacagagg gagaatgcca 55080
tgtgaccacg gaggcaggga gtgaagagct gcagtgacaa gccaaggaca tcaaggacgg 55140
caggccactg ccaaaagcca gggaggggca aggagggctc ctgagacctg gttttcagag 55200
ggagcacagc tctgccaaca ccttcatttc aggctgtggc ctctggaacg ttggctcaat 55260
aaatttgtta aaaaaaaatt ttaaaggctc agcatggtgg ctcatgcctg taatcccagc 55320
actttgggag gcccaggcag gaggatcaca tgaacccagg agtttgagac tagcctgggc 55380
aaaatagtga gacctcatct ctatataaaa atatataaca aaagtcaact tatgtgtttt 55440
aagccatctg gtctatgaca ctttgttctg gcaggcctag gaaagggata cacgtactga 55500
ggagggggac acttcattgg catagaggga gagagtgtga acttggcctt ttgtggaaca 55560
gaggaggctc gggcagaggt ggtgatagtg cagcccattc attctgagat gaaacttcca 55620
ctggtttccg taaaggcgtc ttggggaggg aagggaaggg gatggggacc tcccagtggt 55680
atcccctgct tgggcactga gggaaagcca cagtggctcg ggggaaaagg cagggacgtc 55740
ctctccccgc ctgcctctgt ccccagggag tctcgcctcc tgttcccacc tggggctagg 55800
gtgatagagg agaggagata gctcaacctg gcatttaggt ggtgtgggaa caggagaccc 55860
cagactttct tgttttgggg tctggggcag gcaaccaggc tccagggaca gtgagttgaa 55920
ggaagggtgg ctgggagacc ccttgacttg ctgccaagga gacagagctg gagctagggt 55980
ggccggtggt gtctgaggca ggtgcagaga gggagggagg gaaggggcct ttgactccaa 56040
cctccttttt ctgtaccgac tgcaggtggc agctgccctt tcaggagcca gtgggggaac 56100
ctgggtggct gggtggggac acctgcaagt cctccctaag ccagctacca ccctacactg 56160
ttggcctccc ttctccaact gtggggatgc tgctcaggcc ttttgtgaca tcacacctga 56220
gagtccctgg ggtccagtca ttgctgctgg gcacagcgag gtccaagctc aggtcgccct 56280
gccccctacc caccatgcca gatccagcat cgttgtgggc aaacaattat ctggatgatc 56340
tttatggggc ttaagcttgg gtgggagcag atggggcatg agctggggat ttggggatgg 56400
ggggaatcca cacccccacg tcctggacgt ttaaaaggcc ctctctggca ctgggccggg 56460
gcagaggcca gcagaaaagt gactggagtc cagggacatg atggatcagg aggagaagac 56520
ggaggaaggc tcaggcccct gtgccgaggt gagagggccc tgccccccacc ccaccccccag 56580
ctcaaggtct cagagcccat gattgacaag actagtttgt agggcaccta attaacgagt 56640
gagtctccta ggaccccctg acccagttgt ggctgtagaa aggggctggt gggcttgggg 56700
gtctgagtgc caggccccag ggcagagggc agggctctcc gtgtggaccc ctattgatgg 56760
gagatgctgg gacctggggg tagctcctgg gccatgtttc cctgattcgt gtcccagctc 56820
ccaggccaca ctcatcaggc cccaatctag gacggcggga cacgcatcgg agcctgtccc 56880
ttgaagcggt accacgtgaa gtggcactgc tggccagggc ccctggggcg ggggccggga 56940
ttgggaagga gactcatgtc tcattcagaa cagctctgca gagaggatcg gcggggacca 57000
tggtgagagc tgaggaagtg gggacggcag gccccggggt cagggtgtga gcaagctggc 57060
taggaagttt ggggaggggc ccccaagctg aagggccaac cagactgagc gagtctgtcc 57120
ccaggcgggc tccccagacc aggagggctt cttcaatctg ctgagccacg tgcagggcga 57180
ccggatggag ggacagcgct gttcactgca agccgggccg ggccagacca ccaagagccg 57240
tgagcatggg cacgggggtg ctgtccatgg ggcgtgaacg gggtgggagt gcagggcaag 57300
tggtcatctg gagggcctgg gggcacggga tgtgggaggt ggttgtgcac cctgaagcat 57360
ctgtgtgggg gtgaaggggt agggttgggg gcccccactc cggctgtgtc ctcccaagtc 57420
tgtgaacgtc cacgcagaga gcgaccccac ccccgagatg gacagcctca tggacatgct 57480
ggccagtacc cagggccgcc gcatggatga ccaacgtgtg acagtcagca cgctgcccgc 57540
ttccagcccg tggggtccaa ggtaggtgat gttctggcga tgtcgaggag aaacccgcca 57600
ggcagtgctc tccgatcctg ccctccaccc cagccaggag ggaacagggc ctgccccatc 57660
tctgtccatc cgctgccctg acttcagatg ggaggaccaa ggcccaggca gtggctagag 57720
gggcccaagg ttatacaggg gccatgctag tgtaagaccc atggctggaa cttgtggctc 57780
ctgcccccaa gtctgaaggt tctggggagg ccaaagggag aaaataggac cccttcctag 57840
gaaagtatcc cagggaggaa gtcacgtaag ctcacacata ggatatatac atctgtatac 57900
tcacatctgt tgacttcaca catacacgaa gcttgggttc tgatcaagat cccagcgagg 57960
gccccaagac ctgccacctc acactcaaat gccaccctaa atggcagata ttgagggtaa 58020
acatagacca gtgctcacaa tgaggtggga cacggtggct acctgcaccc tctctccatt 58080
gttcgccacc tgtggccggc actgcccttg agccctcccc ctggctgacc cctcttcatc 58140
cacaggacgg agcacagaaa cgagctggga ccctcagtcc ccaacccctg ctcacccctc 58200
aggacccgac cgctctcggc ttccgtcgga acagcagccc ccagcccccg acacaagccc 58260
cctgagggcc tgaggcatcc tgggtctcac tcggccccca aaaactgata aaagaataaa 58320
acacttaaat gaataacaag gaactgagta tatgtatatt tcatcagggg aggggctagg 58380
actcccactt ggaggcctca ggagttctgc tgggcgtcgc gaaggagctt ctcctcccgc 58440
cgcttccgta acctctcttt gaattcctct atctcttgaa gctaggggtg gagaagcggg 58500
tgggacagga aggggggagg ggcacacacc tcagagccgg gacccccccc ccccgcccac 58560
ctctcccacc accctgcccc agaccacggc ttcagggttc agtgtcttca ctggaagccc 58620
cctgccaatt acaaaggggt ccgcgtggga tccgcttcac tcttccagga gaaggcaata 58680
aggaaaccat ctactcctct gctctcggtt ccttactcat ggctgagagt aaaatgtttc 58740
tttttgagac aaagtctcac tctattgccc aggctggagt gcagtggcgt gatcttgggc 58800
tcactgcaac ctccacctcc tgggttcaag tgattcttct ccctcagcct cccaagcagc 58860
tggaattata ggcgcctgcc accatgcctg gctaagtttt gtatttctgt agacatgggg 58920
tttcgccatg ttggccaggc tggttttgaa ctcctgacct caagtgatct acccacctca 58980
gcctcccatg ccctgggatt acaagcatga gccactgcgc ctggcctaaa attttcatct 59040
aaaacccatc ccggatacaa gaatccagcc tcctccatcc ctctggcagg aagaagagat 59100

```
cacttacctt ctcaggtggc cacagctccc tctgtaagga aaagtcacaa atgggacacg  59160
agccaaaggc ctccagagcc ccacatcagg gcagggtcgg cttatgggag gcagacatta  59220
gtccccagca gactgctgcc ccacaccctc tcccacccct ggaatgaacc ctcaaacact  59280
cctcttatgc ccaccttgcg ctgtatgaca tcgtcctcaa accactcggc ctgattggaa  59340
acccagaaca tagccacagg gaaagtgagg tagattatca tctggaatgg cagagggtgg  59400
gtgaggtgag ctccccccaa gcaatgtgca gaggctcctc agagcctggg ggacccatcc  59460
tactgcagag tccagaagcg cctcgttacg gccgacccaa gaatcccaga actcccacca  59520
agggtacaga aacctcgcac cctaaaacct aactcctata atccaggagg cctcattcct  59580
gaaagttccc tctgagctgg agtcttcctc tcaaacacag acagacacac agacgcccca  59640
gctacaatca aaagcatctc ctcgagacct cattacccat ccccacttaa gatcccggga  59700
gcacccccaa acccaggagg cgtcactctt caactccact tctcgaagtc taggaatctc  59760
cctgtcatag acacccaccc accacgagcc cgagagctcc ccagggatct taagtcttcc  59820
ttctttagag cccccttctc agctcacccc tctctgaggt ccttcctcgg accagccctc  59880
tcacagcccc caaaatcaga agcacaaatc cgagaacccc cccagcccag cgtcccctct  59940
cctggatttc caaccagaaa ggtcctctca aatcttaaga gctttctcct tggagctccc  60000
tcttcctttg aagtccccc atttccaacc tcatcttcag atccaggaag atcccctgcc  60060
cagcctccca acccactcct gtgtccactg acccgaaata tctccagctt cacccccatc  60120
tcgtttctcc cggtcaacaa agccagttcc gcccaaagcc gaccctccag caagacagaa  60180
gctcactggt gttttgcacg ctccattgct gaagctgatt ggccaatgtg tatcctcatg  60240
gcgcatcttc tggcgcctct attctgcttc cggtcgctgg cgtcgtcgaa aagaagtcaa  60300
taacgtgggc ctgtccgtca aaaatgattt aaccaataga aaacgggtct ggctcggagg  60360
ggcgggccgt cagtggtaga cgtcataagc gcgcgactct ctcctgtacc tgggcatcca  60420
gaaaaatggt ggtgatggcg cgactctcgc ggcccgagcg gccggacctt gtcttcgtga  60480
gtccacagag gagccggggg tggcctgcgt tggggcattg ggacctggac gccgcagggg  60540
atcgaggctg ggtcggcaag gagatttagg ccgaaactgc caggccaagg tctgggaacc  60600
ctaatgggcc agagaccgga tcgtcatgtc cgcaccgaac tgtccaggag taaaaatatg  60660
gtgttgtatc ttcgggtctg agtagaaaac cactgtcgaa gggaagcgtc tagcctcccg  60720
aaccaggggc ggaaatgggg gcgtgcaggg aatgggagag gaggaagatc gcataactga  60780
accttgagag gtgaagatcg gtgtctgaag taaaggcttg cttacgaggc cagggttctg  60840
gtttctggga tgaaggcttg gttttctgga tagcggtctc taggcctgga ctgcagcatg  60900
acagtttctg ggtggtggc caggctagaa gaaccctggt gatgtggagc ttgtcaggcg  60960
atggccagtg aaatacttac tctctggagt agaggcgtga catcttcacc agattcttgg  61020
tgtgcagagt taaaggcttg gcttctggtg tataactcct cctgtgagat aaaggcctag  61080
cttttaattt ctggggcaga gttgagctag acgctggcta gtgggatcct gggggcgggg  61140
ctagtggctt ggaatctgga cctgagagcc ctggtggctg ggtaaagat ctggtcatct  61200
gggcctgggg tggagatggg tcagatggtg acagtgggag tctgaggggc aaaggcctgg  61260
tgtctgggaa gaggcacgtt ttgaagaagt ggggtctggt gtccaggact ggcatctggg  61320
ccagggcctt ggtatctaag gagtctgacc atctggggca gaaagcgagt ggtgatgcgg  61380
actcattcct ggcccagagc cctaatgact gagaagtctg atgatttggg ttcgattttg  61440
ggtagttgaa ttctgagggg taaaggtctg ggccactgtc ttggtgtcgg gcatctggtt  61500
```

-continued

```
tggtgcctgg gcatctggtg acctgacttc cttggtgggt ggtgggatct aggtaaaagt  61560
ccggagtttg gacctgagcc ccagcagtgg gatggtgctg cacacaggct ctgagggtag  61620
gcctctcttc ttcccattcc ctggccctgg caggaggaag aggacctccc ctatgaggag  61680
gaaatcatgc ggaaccaatt ctctgtcaaa tgctggcttc gctacatcga gttcaaacag  61740
ggcgccccga agcccaggct caatcagcta tacgagcggg cactcaagct gctgccctgc  61800
aggtgggaat ggctccagct gccctgccca ccagccccca ccccacctgg tccagttata  61860
acaaaactgc caagtgggtc ccgggtcccg ggtgattgct tcgtgtttca tcactgacct  61920
gtacatccct tgatgggtca gcacaccttc tctgatgtcc cagtctgtcc ctgtcattgc  61980
tgagacatgt cacccctccc acacccctte ttcccacatt tgccaactgg ggcagggcaa  62040
atggttctgg gggtgtccat aaagctgacc gatcagcatc tgtcccctcc tattccccag  62100
ctacaaactc tggtaccgat acctgaaggc gcgtcgggca caggtgaagc atcgctgtgt  62160
gaccgaccct gcctatgaag atgtcaacaa ctgtcatgag agggcctttg tgttcatgca  62220
caaggtttgg ggctcggcga ggggatgaat cgggaagtgg agctcagtcc atggtggtgg  62280
gtggggcggg gacaggggct gggctcagca tgttagggat gggggcttgg attcctgttg  62340
cttctttgca tgggaagttg ggctggactc agtcctggag ctgggggttt ctgggtcccg  62400
ccgcatttat gtggtggccc caggtgtggc tcagccacag gacatcgagt gtctgtggcc  62460
aggccatgga gtccgtggct tagccccagc cgcctctccc cacaccccca gatgcctcgt  62520
ctgtggctag attactgcca gttcctcatg gaccaggggc gcgtcacaca cacccgccgc  62580
accttcgacc gtgccctccg ggcactgccc atcacgcagc actctcgaat ttggcccctg  62640
tatctgcgct tcctgcgctc acacccactg cctgagacag ctgtgcgagg ctatcggcgc  62700
ttcctcaagg tgagcctagc aggtgcgctg gttccccagg ttagtttcca gaaacggcct  62760
cactgtgaca ctagctccgt gtaggatgtc acccagcaga cgggatgtgg gaagaggctc  62820
ctggagatgc atgtgttttg ttgttgtccg tgattcatgt ctttattttc caaatagttt  62880
gttcacactg gtttcacatt aggcatagcg atgggtgctg aggacagtgt gactaagaca  62940
ctccctgcct gcacggagct tttagtctaa ctaggaagac agatgcatat gagctgatgg  63000
catgaactag agtaaaacca cagccatgaa gagggccagg aataagggtg gggagaagca  63060
ggcagggtgg agagtggaag caccagccgg gcgggagtgg ggcatggttt gctcaaactt  63120
aaagtatctg ttttatgacg tttggattct aagctggacc agtcaggact gaggctggac  63180
ccgtggggcc caggctggac actatagtca aggctggacc catgggatca aggctgaccc  63240
aaaggggcca aggctagacc agtcaggact gaggctggac tagtggagcc aaggctggac  63300
ccattgtggg ttgggggtca attctaaccc aaaaggacca aggctggacc attggggctg  63360
agactggacc accgcagtca aggctgtgcc cttgcgggtc aaggctaacc caaaaagtcc  63420
acagctggtc tagtcaggac tgaggctgga ccagtggagc caaggcagga cccacagggg  63480
gttgagccta acccagtggg gccaaggcta gaccagtagg aaccgggctg gaccagtggg  63540
gctgaggctg gtttgacagg gcttgctttt gcccaagaca ctcataaatg ggtggggggg  63600
gacgccccga agccactgaa tcgggaggtg ggcgtagccc tgccacccca ctgactgcct  63660
gaggggtggc tcggtcccca gctgagtcct gagagtgcag aggagtacat tgagtacctc  63720
aagtcaagtg accggctgga tgaggccgcc cagcgcctgg ccaccgtggt gaacgacgag  63780
cgtttcgtgt ctaaggccgg caagtccaac taccaggtgg gcctgccggg agccggcaac  63840
tgggtgggag ggccaccccc tccatgactg agcctgagac tctcccccac tgccccatgc  63900
```

-continued

```
cctgcagctg tggcacgagc tgtgcgacct catctcccag aatccggaca aggtacagtc  63960
cctcaatgtg gacgccatca tccgcggggg cctcacccgc ttcaccgacc agctgggcaa  64020
gctctggtgt tctctcgccg actactacat ccgcagcggc catttcgaga aggtgcatgc  64080
tggcacacgg ggctctgggt tcggggcggg gtctccctcc gacactcggg gacacatgtt  64140
gacacatgca cagacagaaa acatgccatt tatggctggg tgtggtggct cacacctgtc  64200
atcccagcac tttgggaggc cgaggcggta ggatcacttg aggtcagcag ttcaagacca  64260
gcctggccaa catggtgaaa ccccatcact actaaaaata caaaaattag tcagacatgg  64320
tggtgcgcgc ctgtaatccc agctactcgg gaggctgagg caggagaatc gcttgaactt  64380
gggaggtgga ggttgccgtg agctgcgatc gcgccacgga agtccagcct gggtggcaga  64440
gcgagactcc atctcaaaaa aaaaaaaaaa aaaaaaaagt gccatttttg acagacatgc  64500
atatccctgc acacgattac tatcctgctg agggtggggg agcactcctg cccgcaagca  64560
cgtcagcctt tggagttcag ccacattttg cgttcagggt ttcaccctct tggctctgcg  64620
gcctttgccc caactaaggg tggtttgttc tttcatttgt aaaaatcagg gtgacagttt  64680
actgccttgt caccaatcag                                              64700
```